(12) United States Patent
Tsui et al.

(10) Patent No.: US 10,011,660 B2
(45) Date of Patent: Jul. 3, 2018

(54) MOLECULES WITH REDUCED EFFECTOR FUNCTION AND EXTENDED HALF-LIVES, COMPOSITIONS, AND USES THEREOF

(71) Applicant: MedImmune, LLC, Gaithersburg, MD (US)

(72) Inventors: Ping Tsui, Gaithersburg, MD (US); Martin Borrok, II, Gaithersburg, MD (US); William Dall'Acqua, Gaithersburg, MD (US)

(73) Assignee: MedImmune, LLC, Gaithersburg, MD (US)

( * ) Notice: Subject to any disclaimer, the term of this patent is extended or adjusted under 35 U.S.C. 154(b) by 486 days.

(21) Appl. No.: 14/397,958

(22) PCT Filed: Apr. 17, 2013

(86) PCT No.: PCT/US2013/036872
§ 371 (c)(1),
(2) Date: Oct. 30, 2014

(87) PCT Pub. No.: WO2013/165690
PCT Pub. Date: Nov. 7, 2013

(65) Prior Publication Data
US 2015/0125444 A1    May 7, 2015

Related U.S. Application Data

(60) Provisional application No. 61/640,327, filed on Apr. 30, 2012.

(51) Int. Cl.
*C07K 16/00*      (2006.01)
*A61K 39/395*     (2006.01)
*C07K 16/28*      (2006.01)
*C07K 16/10*      (2006.01)
*C07K 16/18*      (2006.01)

(52) U.S. Cl.
CPC .... *C07K 16/2887* (2013.01); *A61K 39/39591* (2013.01); *C07K 16/1027* (2013.01); *C07K 16/18* (2013.01); *C07K 16/2866* (2013.01); *C07K 2317/52* (2013.01); *C07K 2317/524* (2013.01); *C07K 2317/71* (2013.01); *C07K 2317/94* (2013.01)

(58) Field of Classification Search
None
See application file for complete search history.

(56) References Cited

U.S. PATENT DOCUMENTS

| 5,624,821 | A | 4/1997 | Winter et al. |
| 6,410,008 | B1* | 6/2002 | Strom .............. A61K 38/2026 424/85.2 |
| 6,737,056 | B1* | 5/2004 | Presta .............. C07K 16/28 424/133.1 |
| 7,083,784 | B2 | 1/2006 | Dall'Acqua et al. |
| 2007/0009523 | A1 | 1/2007 | Presta |
| 2009/0042291 | A1* | 2/2009 | Chu .............. C07K 16/2803 435/375 |
| 2010/0233173 | A1* | 9/2010 | Wu .............. C07K 16/468 424/136.1 |

FOREIGN PATENT DOCUMENTS

| WO | WO2009/003019 A1 | 12/2008 |
| WO | WO2011/005481 A1 | 1/2011 |
| WO | WO2011/044368 A1 | 4/2011 |

OTHER PUBLICATIONS

Xu. Cellular Immunology 2000, 200:16-26.*
Thommesen et al, "Lysine 322 in the human IgG3 CH2 domain is crucial for antibody dependent complement activation", Molecular Immunology, vol. 37, No. 16, 2001, pp. 955-1004.
Dall'Acqua et al, Properties of human IgG1s engineered for enhanced binding to the neonatal Fc receptor (FcRn), Journal of Biological Chemistry, American Society for Biochemistry and Molecular Biology, vol. 281, No. 33, 2006, pp. 23514-23524.
Kuo et al, "Neonatoal Fc receptor and IgG-based therapeutics", mAbs, Landes Bioscience, US, vol. 3, No. 5, 2011, pp. 422-430.
Presta et al, "Molecular engineering and design of therapeutic antibodies," Current Opinion in Immunology, Elsevier, vol. 20, No. 4, 2008, pp. 460-470.
International Preliminary Report on Patentability for International Application No. PCT/US2013/036872, US Patent Office dated Nov. 4, 2014.
Written Opinion for International Application No. PCT/US2013/036872, US Patent Office dated Oct. 11, 2013.
International Search Report for International Application No. PCT/US2013/036872, US Patent Office dated Oct. 11, 2013.
European Search Report, for EP Application No. EP13784604.4, dated Nov. 11, 2015.
Supplementary European Search Report, for EP Application No. EP13784604.4, dated Oct. 23, 2015.

\* cited by examiner

*Primary Examiner* — Chun W Dahle

(57) ABSTRACT

Provided are polypeptides comprising a variant IgG Fc domain, wherein the polypeptides exhibit reduced or ablated effector functions (e.g., ADCC and/or CDC) and increased stability and plasma half-life compared to a parent polypeptide. Also provided are compositions, methods of treatment, and methods to diminish Fc-induced effector function in a parent polypeptide.

47 Claims, 9 Drawing Sheets

| EU | 118 | 119 | 120 | 121 | 122 | 123 | 124 | 125 | 126 | 127 | 128 | 129 | 130 | 131 | 132 | 133 | 134 | 135 | 136 | 137 |
|---|---|---|---|---|---|---|---|---|---|---|---|---|---|---|---|---|---|---|---|---|
| IgG1 | A | S | T | K | G | P | S | V | F | P | L | A | P | S | S | K | S | T | S | G |
| IgG2 | A | S | T | K | G | P | S | V | F | P | L | A | P | C | S | R | S | T | S | E |
| IgG3 | A | S | T | K | G | P | S | V | F | P | L | A | P | C | S | R | S | T | S | G |
| IgG4 | A | S | T | K | G | P | S | V | F | P | L | A | P | C | S | R | S | T | S | E |

| EU | 138 | 139 | 140 | 141 | 142 | 143 | 144 | 145 | 146 | 147 | 148 | 149 | 150 | 151 | 152 | 153 | 154 | 155 | 156 | 157 |
|---|---|---|---|---|---|---|---|---|---|---|---|---|---|---|---|---|---|---|---|---|
| IgG1 | G | T | A | A | L | G | C | L | V | K | D | Y | F | P | E | P | V | T | V | S |
| IgG2 | S | T | A | A | L | G | C | L | V | K | D | Y | F | P | E | P | V | T | V | S |
| IgG3 | G | T | A | A | L | G | C | L | V | K | D | Y | F | P | E | P | V | T | V | S |
| IgG4 | S | T | A | A | L | G | C | L | V | K | D | Y | F | P | E | P | V | T | V | S |

| EU | 158 | 159 | 160 | 161 | 162 | 163 | 164 | 165 | 166 | 167 | 168 | 169 | 170 | 171 | 172 | 173 | 174 | 175 | 176 | 177 |
|---|---|---|---|---|---|---|---|---|---|---|---|---|---|---|---|---|---|---|---|---|
| IgG1 | W | N | S | G | A | L | T | S | G | V | H | T | F | P | A | V | L | Q | S | S |
| IgG2 | W | N | S | G | A | L | T | S | G | V | H | T | F | P | A | V | L | Q | S | S |
| IgG3 | W | N | S | G | A | L | T | S | G | V | H | T | F | P | A | V | L | Q | S* | S |
| IgG4 | W | N | S | G | A | L | T | S | G | V | H | T | F | P | A | V | L | Q | S | S |

| EU | 178 | 179 | 180 | 181 | 182 | 183 | 184 | 185 | 186 | 187 | 188 | 189 | 190 | 191 | 192 | 193 | 194 | 195 | 196 | 197 |
|---|---|---|---|---|---|---|---|---|---|---|---|---|---|---|---|---|---|---|---|---|
| IgG1 | G | L | Y | S | L | S | S | V | V | T | V | P | S | S | S | L | G | T | Q | T |
| IgG2 | G | L | Y | S | L | S | S | V | V | T | V | P* | S | S | N* | F* | G | T | Q | T |
| IgG3 | G | L | Y | S | L | S | S | V | V | T | V | P | S | S | S* | L* | G | T | Q | T |
| IgG4 | G | L | Y | S | L | S | S | V | V | T | V | P | S | S | S | L | G | T | K | T |

*site of known allelic variation

| EU   | 198 | 199 | 200 | 201 | 202 | 203 | 204 | 205 | 206 | 207 | 208 | 209 | 210 | 211 | 212 | 213 | 214 | 215 | 216 | 217 |
|------|-----|-----|-----|-----|-----|-----|-----|-----|-----|-----|-----|-----|-----|-----|-----|-----|-----|-----|-----|-----|
| IgG1 | Y   | I   | C   | N   | V   | N   | H   | K   | P   | S   | N   | T   | K   | V   | D   | K   | K*  | V   | E   | P   |
| IgG2 | Y   | T   | C   | N   | V   | D   | H   | K   | P   | S   | N   | T   | K   | V   | D   | K   | T   | V   | E   | R   |
| IgG3 | Y   | T   | C   | N   | V   | N   | H   | K   | P   | S   | N   | T   | K   | V   | D   | K   | R   | V   | E   | L   |
| IgG4 | Y   | T   | C   | N   | V   | D   | H   | K   | P   | S   | N   | T   | K   | V   | D   | K   | R   | V   | E   | S   |

| EU   | 218 | 219 | 220 | 221 | 222 | 223 | 224 | 225 | 226 | 227 | 228 |
|------|-----|-----|-----|-----|-----|-----|-----|-----|-----|-----|-----|
| IgG1 | K   | S   | C   | D   | K   | T   | H   | T   | C   | P   | P   |
| IgG2 | K   |     | C   | C   | V   |     | E   |     | C   | P   | P   |
| IgG3 | K   | T   | P   | L   | G   | D   | T   | T   | H   | T   | C   |
| IgG4 | K   | Y   | G   |     |     |     |     |     | P   | P   | S   |

| EU   |   |   |   |   |   |   |   |   |   |   |   |
|------|---|---|---|---|---|---|---|---|---|---|---|
| IgG1 |   |   |   |   |   |   |   |   |   |   |   |
| IgG2 |   |   |   |   |   |   |   |   |   |   |   |
| IgG3 | D | T | P | P | P | C | P | R | C | P | P |
| IgG4 |   |   |   |   |   |   |   |   |   |   |   |

| EU   |   |   |   |   |   |   |   |   |   |   |   |
|------|---|---|---|---|---|---|---|---|---|---|---|
| IgG1 |   |   |   |   |   |   |   |   |   |   |   |
| IgG2 |   |   |   |   |   |   |   |   |   |   |   |
| IgG3 | C | P | R | C | P | E | P | K | S | C | D |
| IgG4 |   |   |   |   |   |   |   |   |   |   |   |

| EU   |   |   |   |   |   | 229 | 230 |
|------|---|---|---|---|---|-----|-----|
| IgG1 |   |   |   |   |   | C   | P   |
| IgG2 |   |   |   |   |   | C   | P   |
| IgG3 | T | P | P | C | R | C   | P   |
| IgG4 |   |   |   |   |   | C   | P   |

*site of known allelic variation

FIG. 7

*site of known allelic variation

| EU | 341 | 342 | 343 | 344 | 345 | 346 | 347 | 348 | 349 | 350 | 351 | 352 | 353 | 354 | 355 | 356 | 357 | 358 | 359 | 360 | 361 | 362 |
|---|---|---|---|---|---|---|---|---|---|---|---|---|---|---|---|---|---|---|---|---|---|---|
| IgG1 | G | Q | P | R | E | P | Q | V | Y | T | L | P | P | S | R | D* | E | L* | T | K | N | Q |
| IgG2 | G | Q | P | R | E | P | Q | V | Y | T | L | P | P | S | R | E | E | M | T | K | N | Q |
| IgG3 | G | Q | P | R | E | P | Q | V | Y | T | L | P | P | S | R | E | E | M | T | K | N | Q |
| IgG4 | G | Q | P | R | E | P | Q | V | Y | T | L | P | P | S | Q | E | E | M | T | K | N | Q |

| EU | 363 | 364 | 365 | 366 | 367 | 368 | 369 | 370 | 371 | 372 | 373 | 374 | 375 | 376 | 377 | 378 | 379 | 380 | 381 | 382 | 383 | 384 |
|---|---|---|---|---|---|---|---|---|---|---|---|---|---|---|---|---|---|---|---|---|---|---|
| IgG1 | V | S | L | T | C | L | V | K | G | F | Y | P | S | D | — | A | V | E | W | E | S | N |
| IgG2 | V | S | L | T | C | L | V | K | G | F | Y | P | S | D | — | S* | V | E | W | E | S | N |
| IgG3 | V | S | L | T | C | L | V | K | G | F | Y | P | S | D | — | A | V* | E | W | E | S | S* |
| IgG4 | V | S | L | T | C | L | V | K | G | F | Y | P | S | D | — | A | V | E | W | E | S | N |

| EU | 385 | 386 | 387 | 388 | 389 | 390 | 391 | 392 | 393 | 394 | 395 | 396 | 397 | 398 | 399 | 400 | 401 | 402 | 403 | 404 | 405 | 406 |
|---|---|---|---|---|---|---|---|---|---|---|---|---|---|---|---|---|---|---|---|---|---|---|
| IgG1 | G | Q | P | E | N | N | Y | K | T | T | P | P | V | L | D | S | D | G | S | F | F | L |
| IgG2 | G | Q | P | E | N | N | Y | K | T | T | P | P | M | L | D | S | D | G | S | F | F | L |
| IgG3 | G | Q | P | E | N | N* | Y | N | T | T | P | P | M* | L | D | S | D | G | S | F | F | L |
| IgG4 | G | Q | P | E | N | N | Y | K | T | T | P | P | V | L | D | S | D | G | S | F | F | L |

| EU | 407 | 408 | 409 | 410 | 411 | 412 | 413 | 414 | 415 | 416 | 417 | 418 | 419 | 420 | 421 | 422 | 423 | 424 | 425 | 426 | 427 | 428 |
|---|---|---|---|---|---|---|---|---|---|---|---|---|---|---|---|---|---|---|---|---|---|---|
| IgG1 | Y | S | K | L | T | V | D | K | S | R | W | Q | Q | G | N | V | F | S | C | S | V | M |
| IgG2 | Y | S | K | L | T | V | D | K | S | R | W | Q | Q | G | N | V | F | S | C | S | V | M |
| IgG3 | Y | S | K* | L | T | V | D | K | S | R | W | Q | Q* | G | N | I* | F | S | C | S | V | M |
| IgG4 | Y | S | R* | L | T | V | D | K | S | R | W | Q | E | G | N | V | F | S | C | S | V | M |

| EU | 429 | 430 | 431 | 432 | 433 | 434 | 435 | 436 | 437 | 438 | 439 | 440 | 441 | 442 | 443 | 444 | 445 | 446 | 447 |
|---|---|---|---|---|---|---|---|---|---|---|---|---|---|---|---|---|---|---|---|
| IgG1 | H | E | A | L | H | N | H | Y | T | Q | K | S | L | S | L | S | P | G | K |
| IgG2 | H | E | A | L | H | N | H | Y | T | Q | K | S | L | S | L | S | P | G | K |
| IgG3 | H | E | A | L | H | N | R* | F* | T | Q | K | S | L | S | L | S | P | G | K |
| IgG4 | H | E | A | L | H | N | H | Y | T | Q | K | S | L | S | L | G | L | G | K |

*site of known allelic variation

FIG. 8

MOLECULES WITH REDUCED EFFECTOR FUNCTION AND EXTENDED HALF-LIVES, COMPOSITIONS, AND USES THEREOF

CROSS-REFERENCE TO RELATED APPLICATIONS

This application is a U.S. National Stage application of International Application No. PCT/US2013/36872, filed on Apr. 17, 2013, said International Application No. PCT/US2013/36872 claims benefit under 35 U.S.C. § 119(e) of the U.S. Provisional Application No. 61/640,327, filed Apr. 30, 2012. Each of the above listed applications is incorporated by reference herein in its entirety for all purposes.

REFERENCE TO THE SEQUENCE LISTING

This application incorporates by reference a Sequence Listing submitted with this application as text file entitled "AEFC_120WO1_SL.txt" created on Apr. 5, 2013 and have a size of 96 kilobytes

FIELD

The present disclosure relates to molecules, in particular polypeptides, including but not limited to immunoglobulins (e.g., antibodies), comprising a variant IgG Fc domain comprising mutations that result in reduced effector function and extended half-life while maintaining favorable stability. The disclosure also comprises nucleic acids encoding such polypeptides, expression vectors, host cells, and methods of making and using them, including therapeutic and diagnostic compositions, formulations, and kits.

BACKGROUND ART

Antibodies are made up of two distinct regions, referred to as the variable (Fv) and constant (Fc) regions. The Fc region of an antibody interacts with a number of ligands, such as Fc receptors and C1q, imparting an array of functional capabilities referred to as effector functions. Fc receptors mediate communication between antibodies and the cellular arm of the immune system (Raghavan et al., Annu. Rev. Cell. Dev. Biol. 12:181-220 (1996); Ravetch et al., Annu. Rev. Immunol. 19:275-290, (2001)).

The formation of the Fc/FcγR complex typically resulting in signaling events within these cells and subsequent immune responses such as release of inflammation mediators, B cell activation, endocytosis, phagocytosis, and cytotoxic attack. The cell-mediated reaction wherein nonspecific cytotoxic cells that express FcγRs recognize an antibody bound on a target cell and subsequently cause lysis of the target cell is referred to as antibody dependent cell-mediated cytotoxicity (ADCC) (Ghetie et al., Annu. Rev. Immunol. 18:739-766 (2000); Ravetch et al., Annu. Rev. Immunol. 19:275-290 (2001)).

Human FcγRs are divided into three distinct classes: FcγRI (CD64), FcγRII (CD32) and FcγRIII (CD16). IgG molecules exhibit differential isotype specificity for FcγRs. IgG3 molecules bind strongly to all FcγR isoforms. IgG1, the most prevalent isoform in the blood binds to all FcγRs albeit with a lower affinity for the FcγRIIA/β isoforms. IgG4 is an intermediate binder to FcγRI and a weak binder to FcγRIIB. Finally, IgG2 binds only weakly to one allelic form of FcγRIIA (FcγRIIA-H131) (Siberil et al., J. Immunol. Lett. 106:111-118 (2006)). A short continuous stretch of amino acid residues (234-238) of the N-terminus part of the CH2 region as being directly involved in the binding to all FcγRs. Residues 268, 297, 327 and 329 can also impact binding to a subset of FcγRs, and multiple residues located in the CH2 and CH3 regions also contribute to FcγR binding (Canfield et al., J. Exp. Med. 173:1483-91 (1991), Chappel et al., Proc. Natl. Acad. Sci. USA 888:9036-40 (1991), Gergely et al. FASEB J. 4:3275-83 (1990)).

An overlapping site on the Fc region of the molecule controls the activation of a cell independent cytotoxic function mediated by complement. Accordingly, Fc binding to complement protein C1q mediates a process called complement dependent cytotoxicity (CDC) (see Ward et al., Ther. Immunol. 2:77-94 (1995)).

In certain instances it is advantageous to decrease or eliminate effector function. In these cases the use of antibodies or Fc domain-containing fragments that poorly recruit complement or effector cells is beneficial (see, e.g., Wu et al., Cell Immunol. 200:16-26 (2000); Shields et al., J. Biol. Chem. 276:6591-6604 (2001); U.S. Pat. No. 6,194,551; U.S. Pat. No. 5,885,573; PCT publication WO 04/029207; and U.S. Publ. No. 2011/0059078).

Although certain subclasses of human immunoglobulins poorly recruit complement or effector cells, for example IgG2 and IgG4, there are no known naturally occurring immunoglobulins that lack all effector functions. Thus, an alternate approach is to engineer or mutate residues in the Fc region that are responsible for effector function. See, e.g., PCT publications WO2006076594, WO199958572, WO2006047350, and WO2006053301; U.S. Pat. Pub. No. 2006-0134709; U.S. Pat. Nos. 5,624,821, 6,194,551, and 5,885,573; Armour et al., Eur. J. Immunol. 29:2613-2624 (1999); Reddy et al., J. Immunol. 164:1925-1933 (2000); Xu et al., Cell Immunol. 200:16-26 (2000); Shields et al., J. Biol. Chem. 276:6591-6604 (2001).

A consideration for the reduction or elimination of effector function is that other important antibody properties not be perturbed. Thus, Fc variants should be engineered to only ablate binding to FcγRs and/or C1q, while maintaining antibody stability, solubility, and structural integrity, as well as the ability to interact with other important Fc ligands such as FcRn and proteins A and G.

BRIEF SUMMARY

The present disclosure is directed to recombinant polypeptides comprising a variant Fc domain with amino acid substitutions resulting in desired properties, e.g., reduced effector function, and improved plasma half-life, while maintaining stability, e.g., thermal stability. In some aspects, the polypeptide of the disclosure comprises a variant IgG Fc domain, wherein the variant IgG Fc domain comprises (a) a Phenylalanine (F) amino acid at position 234; (b) an Alanine (A), Asparagine (N), Phenylalanine (F), Glutamine (Q), or Valine (V) amino acid at position 235; and, (c) an Alanine (A), Aspartic acid (D), Glutamic acid (E), Histidine (H), Asparagine (N), or Glutamine (Q) amino acid at position 322; or, an Alanine (A) or Glycine (G) amino acid at position 331, wherein the amino acid numbering is according to the EU index as in Kabat.

In other aspects, the polypeptide comprises a Phenylalanine (F) amino acid at position 234; a Glutamine (Q) amino acid at position 235; and a Glutamine (Q) amino acid at position 322, wherein the amino acid numbering is according to the EU index as in Kabat. In some aspects, the polypeptide comprises a Phenylalanine (F) amino acid at position 234; a Glutamine (Q) amino acid at position 235; and a Glycine (G) amino acid at position 331, wherein the amino acid numbering is according to the EU index as in Kabat. In some aspects, the polypeptide comprises a Phenylalanine (F) amino acid at position 234; an Alanine (A) amino acid at position 235; and a Glutamine (Q) amino acid at position 322, wherein the amino acid numbering is according to the EU index as in Kabat.

In some aspects, the polypeptide further comprises (a) a Tyrosine (Y) amino acid at position 252, or a Serine (S) amino acid at position 252, or a Tryptophan (W) amino acid at position 252 or a Threonine (T) amino acid at position 252; and/or (b) a Threonine (T) amino acid at position 254; and/or (c) a Glutamic acid (E) amino acid at position 256, or a Serine (S) amino acid at position 256, or a Arginine (R) amino acid at position 256, or a Glutamine (Q) amino acid at position 256, or an Aspartate (D) amino acid at position 256, wherein the amino acid numbering is according to the EU index as in Kabat.

In other aspects, the polypeptide further comprises (a) a Tyrosine (Y) amino acid at position 252; and/or (b) a Threonine (T) amino acid at position 254; and/or (c) a Glutamic acid (E) amino acid at position 256, wherein the amino acid numbering is according to the EU index as in Kabat. In other aspects, the polypeptide comprises (a) a Tyrosine (Y) amino acid at position 252, or a Serine (S) amino acid at position 252, or a Tryptophan (W) amino acid at position 252 or a Threonine (T) amino acid at position 252; and (b) a Threonine (T) amino acid at position 254, wherein the amino acid numbering is according to the EU index as in Kabat. In some aspects, the polypeptide comprises (a) a Threonine (T) amino acid at position 254; and (b) a Glutamic acid (E) amino acid at position 256, or a Serine (S) amino acid at position 256, or a Arginine (R) amino acid at position 256, or a Glutamine (Q) amino acid at position 256, or an Aspartate (D) amino acid at position 256, wherein the amino acid numbering is according to the EU index as in Kabat.

In some aspects, the polypeptide further comprises (a) a Tyrosine (Y) amino acid at position 252, or a Serine (S) amino acid at position 252, or a Tryptophan (W) amino acid at position 252 or a Threonine (T) amino acid at position 252; and (b) a Glutamic acid (E) amino acid at position 256, or a Serine (S) amino acid at position 256, or a Arginine (R) amino acid at position 256, or a Glutamine (Q) amino acid at position 256, or an Aspartate (D) amino acid at position 256, wherein the amino acid numbering is according to the EU index as in Kabat.

In some aspects, the polypeptide further comprises (a) a Tyrosine (Y) amino acid at position 252, and a Threonine (T) amino acid at position 254; or, (b) a Threonine (T) amino acid at position 254 and a Glutamic acid (E) amino acid at position 256; or, (c) a Tyrosine (Y) amino acid at position 252 and a Glutamic acid (E) amino acid at position 256, wherein the amino acid numbering is according to the EU index as in Kabat. In some aspects, the polypeptide comprises a Tyrosine (Y) amino acid at position 252, a Threonine (T) amino acid at position 254, and, a Glutamic acid (E) amino acid at position 256, wherein the amino acid numbering is according to the EU index as in Kabat.

In one aspect the polypeptide comprises (a) a Phenylalanine (F) amino acid at position 234; (b) a Glutamine (Q) amino acid at position 235; (c) a Glutamine (Q) amino acid at position 322; (d) a Tyrosine (Y) amino acid at position 252; (e) a Threonine (T) amino acid at position 254; and, (f) a Glutamic acid (E) amino acid at position 256, wherein the amino acid numbering is according to the EU index as in Kabat. In one aspect, the polypeptide comprises (a) a Phenylalanine (F) amino acid at position 234; (b) a Glutamine (Q) amino acid at position 235; (c) a Glycine (G) amino acid at position 331; (d) a Tyrosine (Y) amino acid at position 252; (e) a Threonine (T) amino acid at position 254; and, (f) a Glutamic acid (E) amino acid at position 256, wherein the amino acid numbering is according to the EU index as in Kabat. In another aspect, the polypeptide comprises (a) a Phenylalanine (F) amino acid at position 234; (b) an Alanine (A) amino acid at position 235; (c) a Glutamine (Q) amino acid at position 322; (d) a Tyrosine (Y) amino acid at position 252; (e) a Threonine (T) amino acid at position 254; and, (f) a Glutamic acid (E) amino acid at position 256, wherein the amino acid numbering is according to the EU index as in Kabat.

In some aspects, the polypeptide has an improved pharmacokinetic (PK) property when compared to the same polypeptide comprising a wild-type Fc domain. In some aspects, the PK property is half-life. In certain aspects, the polypeptide has improved FcRn binding when compared to the same polypeptide comprising a wild-type Fc domain. In some aspects, the IgG Fc domain is non-human. In other aspects, the IgG Fc domain is human. In specific aspects, the non-human IgG Fc domain is from rodent, donkey, sheep, rabbit, goat, guinea pig, camel, horse or chicken.

In some aspects, the IgG Fc domain is selected from the group consisting of human immunoglobulin G class 1 ($IgG_1$) Fc domain, human immunoglobulin G class 2 ($IgG_2$) Fc domain, human immunoglobulin G class 3 ($IgG_3$) Fc domain, and human immunoglobulin G class 4 ($IgG_4$) Fc domain. In some aspects, the polypeptide further comprises an antigen binding domain. In some aspects, the antigen-binding domain is derived from a monoclonal antibody or an antigen-binding fragment thereof. In some aspects, the antigen-binding domain is derived from a human antibody, a humanized antibody, or a chimeric antibody. In some aspects, the antigen-binding domain comprises (a) a single chain antibody; (b) a diabody; (c) a polypeptide chain of an antibody; (d) an F(ab')$_2$ fragment; or, (e) and F(ab) fragment.

In some aspects, the polypeptide has reduced Fc-mediated effector function when compared to the same polypeptide comprising a wild-type Fc domain. In some aspects, the effector function is antibody-dependent cell-mediated cytotoxicity (ADCC). In other aspects, the effector function is complement-dependent cytotoxicity (CDC). In some aspects, the polypeptide has lower affinity for an Fc gamma receptor (FcγR) when compared to the same polypeptide comprising a wild-type Fc domain. In some aspects, the FcγR is a human FcγR. In some aspects, the FcγR is selected from the group consisting of FcγRI, FcγRII, and FcγRIII. In some aspects, the FcγRI is FcγRIα. In other aspects, the FcγRII is FcγRIIa or FcγRIIb. In yet other aspects, the FcγRIII is FcγRIII (158V) or FcγRIII (158F).

In some aspects, the polypeptide binds with improved affinity to FcRn when compared to the same polypeptide comprising a wild-type Fc domain. In some aspects, the polypeptide has a higher affinity for FcRn at pH 6.0 than at pH 7.4. In some aspects, the polypeptide binds with reduced affinity to C1q when compared to the same polypeptide comprising a wild-type Fc domain.

In some aspects, the polypeptide displays an increase in thermal stability when compared to the same polypeptide comprising a FES-YTE IgG Fc domain. In some aspects, the thermal stability is measured by Differential Scanning calorimetry (DSC). In certain aspects, the increase in thermal stability is at least 4° C. I some aspects, thermal stability is measured by Differential Scanning Fluorimetry (DSF). In specific aspects, the DSF fluorescent probe is Sypro Orange. In some aspects, the increase in thermal stability increases is at least 5° C.

In some aspects, the polypeptide displays an increase in apparent solubility as measured using a polyethylene glycol (PEG) precipitation assay when compared to the same polypeptide comprising a FES-YTE IgG Fc domain. In some aspects, the polypeptide displays an increase in stability as measured using an accelerated stability assay when compared to the same polypeptide comprising a FES-YTE IgG Fc domain. In some aspects, the accelerated stability assay comprises (i) incubation of the polypeptide for an extended time period, and (ii) incubation at high temperature. In some aspects, the accelerated stability assay is performed by incubation at a high concentration. In some aspects, the extended time period is at least one month. In certain aspects, the high concentration is at least 25 mg/ml. In certain aspects, the high temperature is at least 40° C. In some aspects, the accelerated stability assay is performed using High Performance Size Exclusion Chromatography (HPSEC) or Dynamic Light Scattering (DLS).

The present disclosure also provides an isolated nucleic acid comprising a sequence encoding the polypeptide of the disclosure. Also provided are compositions, expression vectors, and host cells which comprise a nucleic acid comprising a sequence encoding the polypeptide of the disclosure. The host cell can comprise an isolated nucleic acid comprising a sequence encoding the polypeptide of the disclosure, a composition comprising a nucleic acid comprising a sequence encoding the polypeptide of the disclosure, or an expression vectors comprising a nucleic acid comprising a sequence encoding the polypeptide of the disclosure.

The present disclosure also provides a method of making a polypeptide of the disclosure comprising (a) culturing host cells comprising a nucleic acid comprising a sequence encoding the polypeptide of the disclosure; and, (b) isolating the polypeptide. The present disclosure also provides a composition comprising a polypeptide of the disclosure and a carrier.

The present disclosure also provides a diagnostic reagent comprising a polypeptide of the disclosure. In some aspects, the polypeptide is labeled. The present disclosure also provides a conjugate comprising a polypeptide of the disclosure and a therapeutic moiety. The present disclosure also provides a kit comprising (a) a polypeptide of the disclosure, (b) an isolated nucleic acid comprising a sequence encoding the polypeptide of the disclosure, (c) a composition, expression vector, or host cell which comprises a nucleic acid comprising a sequence encoding the polypeptide of the disclosure, (d) a composition comprising a polypeptide of the disclosure and a carrier, (e) a diagnostic reagent comprising a polypeptide of the disclosure, which in some aspects it can be labeled, or (f) a conjugate comprising a polypeptide of the disclosure and a therapeutic moiety.

The present disclosure also provides a method of treating a mammal, comprising administering to a mammal in need of treatment an effective amount of (a) a polypeptide of the disclosure, (b) an isolated nucleic acid comprising a sequence encoding the polypeptide of the disclosure, (c) a composition, expression vector, or host cell which comprises a nucleic acid comprising a sequence encoding the polypeptide of the disclosure, (d) a composition comprising a polypeptide of the disclosure and a carrier, (e) a diagnostic reagent comprising a polypeptide of the disclosure, which in some aspects it can be labeled, or (f) a conjugate comprising a polypeptide of the disclosure and a therapeutic moiety.

The present disclosure also provides a method to diminish Fc-induced effector function in a parent polypeptide comprising an Fc domain comprising (a) substituting the amino acid at position 234 in the Fc domain with Phenylalanine (F); (b) substituting the amino acid at position 235 in the Fc domain with Alanine (A), Asparagine (N), Phenylalanine (F), Glutamine (Q), or Valine (V); and, (c) substituting the amino acid at position 322 of the Fc domain with Alanine (A), Aspartic acid (D), Glutamic acid (E), Histidine (H), Asparagine (N), or Glutamine (Q); or substituting the amino acid at position 331 of the Fc domain with Alanine (A) or Glycine (G), wherein the amino acid numbering of the Fc domain is according to the EU index as in Kabat. In some aspects of this method, the Fc domain of the parent polypeptide comprises (a) a Tyrosine (Y) amino acid at position 252, or a Serine (S) amino acid at position 252, or a Tryptophan (W) amino acid at position 252 or a Threonine (T) amino acid at position 252; and/or (b) a Threonine (T) amino acid at position 254; and/or (c) a Glutamic acid (E) amino acid at position 256, or a Serine (S) amino acid at position 256, or an Arginine (R) amino acid at position 256, or a Glutamine (Q) amino acid at position 256, or an Aspartate (D) amino acid at position 256, wherein the amino acid numbering of the Fc domain is according to the EU index as in Kabat. In other aspects of this method, the Fc domain of the parent polypeptide comprises (a) a Tyrosine (Y) at position 252; and/or (b) a Threonine (T) at position 254; and/or, (c) a Glutamic acid (E) at position 256; wherein the amino acid numbering of the Fc domain is according to the EU index as in Kabat.

Also provided is a method to diminish Fc-induced effector function and increase the half-life of a parent polypeptide comprising an Fc domain, the method comprising (a) substituting the amino acid at position 234 in the Fc domain with Phenylalanine (F); (b) substituting the amino acid at position 235 in the Fc domain with Alanine (A), Asparagine (N), Phenylalanine (F), Glutamine (Q), or Valine (V); and, (c) substituting the amino acid at position 322 of the Fc domain with Alanine (A), Aspartic acid (D), Glutamic acid (E), Histidine (H), Asparagine (N), or Glutamine (Q); or substituting the amino acid at position 331 of the Fc domain with Alanine (A) or Glycine (G); and (d) substituting the amino acid at position 252 with Tyrosine (Y) or Serine (S) or Tryptophan (W) or Threonine (T); wherein the amino acid numbering of the Fc domain is according to the EU index as in Kabat. In some aspects of the method, the amino acid at position 252 is substituted with Tyrosine (Y), wherein the amino acid numbering is according to the EU index as in Kabat. In some aspects of this method, (a) the amino acid at position 254 can be substituted with Threonine (T); and, (b) the amino acid at position 256 can be substituted with Glutamic acid (E) or Serine (S), or Arginine (R), or Glutamine (Q), wherein the amino acid numbering of the Fc domain is according to the EU index as in Kabat. In other aspects of this method, the amino acid at position 256 is substituted with Glutamic acid (E), wherein the amino acid numbering is according to the EU index as in Kabat. In some aspects of this method, the amino acid at position 234 is substituted with Phenylalanine (F); the amino acid at position 235 is substituted with Glutamine (Q); and the amino acid at position 322 is substituted with Glutamine (Q), wherein the amino acid numbering is according to the EU index as in Kabat. In some aspects, the amino acid at position 234 substituted with Phenylalanine (F); the amino acid at position 235 is substituted with Glutamine (Q); and the amino acid at position 331 is substituted with Glycine (G), wherein the amino acid numbering is according to the EU index as in Kabat. In some aspects of this method, the amino acid at position 234 is substituted with Phenylalanine (F); the amino acid at position 235 is substituted with Alanine (A); and the amino acid at position 322 is substituted with Glutamine (Q), wherein the amino acid numbering is according to the EU index as in Kabat. In other aspects of this method, the effector function is antibody-dependent cell-mediated cytotoxicity (ADCC). In some aspects of this method, the effector function is complement-dependent cytotoxicity (CDC). In other aspects of this method, the polypeptide displays an increase in thermal stability when compared to the same polypeptide comprising a FES-YTE IgG Fc domain. In some aspects of this method, thermal stability is measured by Differential Scanning calorimetry (DSC). In some aspects of the method, the increase in thermal stability is at least 4° C. In certain aspects of this method, thermal stability is measured by Differential Scanning Fluorimetry (DSF) using a DSF fluorescent probe. In some aspects of this method, the DSF fluorescent probe is Sypro Orange. In some aspects of this method, the increase in thermal stability is at least 5° C. In other aspects of this method, the polypeptide displays an increase in apparent solubility as measured using a polyethylene glycol (PEG) precipitation assay when compared to the same polypeptide comprising a FES-YTE IgG Fc domain. In other aspects of this method, the polypeptide displays an increase in stability as measured using an accelerated stability assay when compared to the same polypeptide comprising a FES-YTE IgG Fc domain. In some aspects of this method, the accelerated stability assay comprises: (i) incubation of the polypeptide for an extended time period, and (ii) incubation at high temperature. In some aspects of the method, the accelerated stability assay is performed by incubation at a high concentration. In some aspects of this method, the extended time period is at least one month. In some aspects of this method, the high concentration is at least 25 mg/ml. In certain aspects of this method, the high temperature is at least 40° C.

BRIEF DESCRIPTION OF THE DRAWINGS/FIGURES

Figure 3:
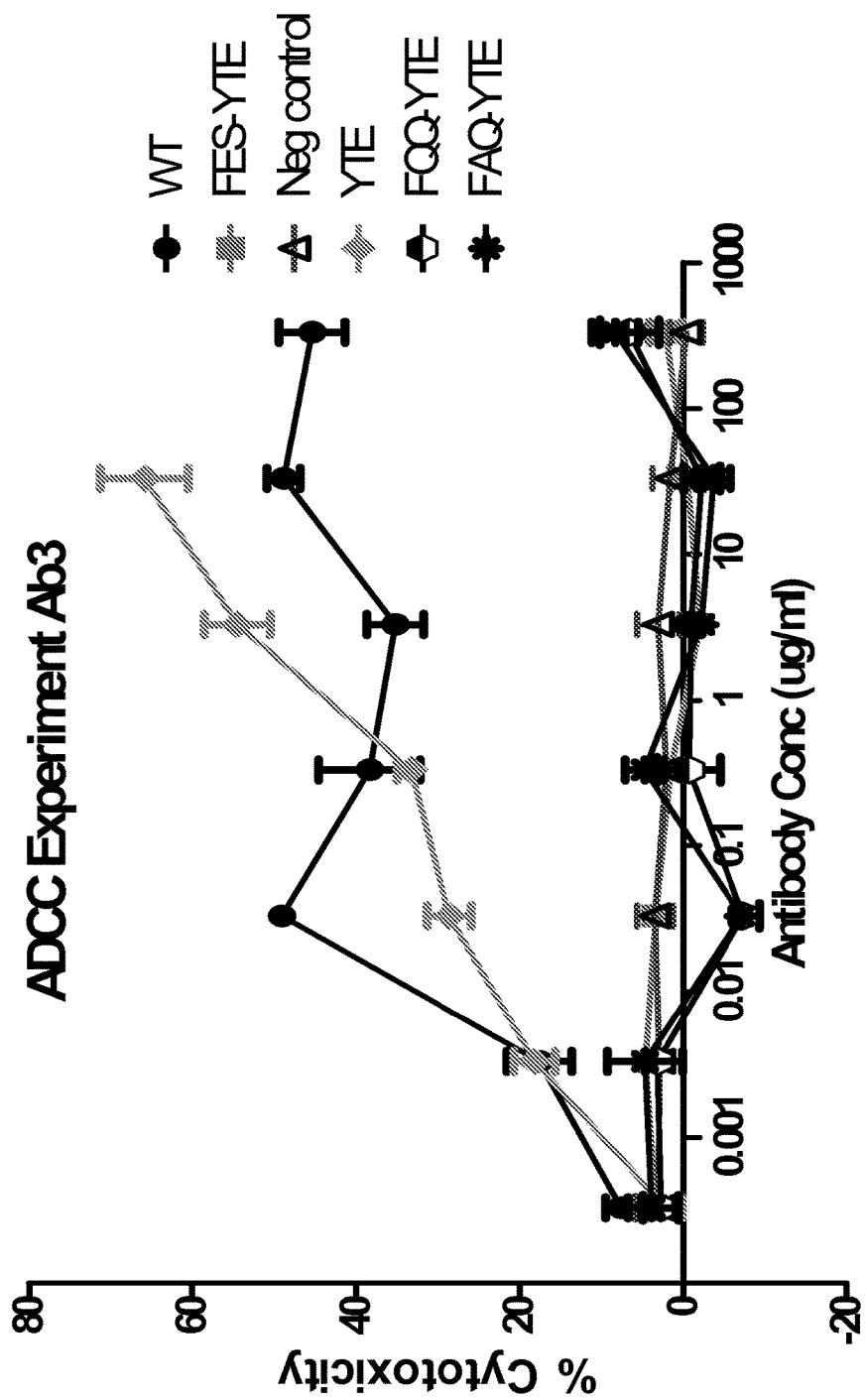

FIG. 3 shows ADCC as measured in cytotoxicity assays. The antibody samples corresponded to Ab3 antibodies comprising wild-type (WT) Fc domains, and to Ab3 antibodies comprising FQQ-YTE, FAQ-YTE, YTE, or FES-YTE variant Fc domains. A negative control was also used.

Figure 4:
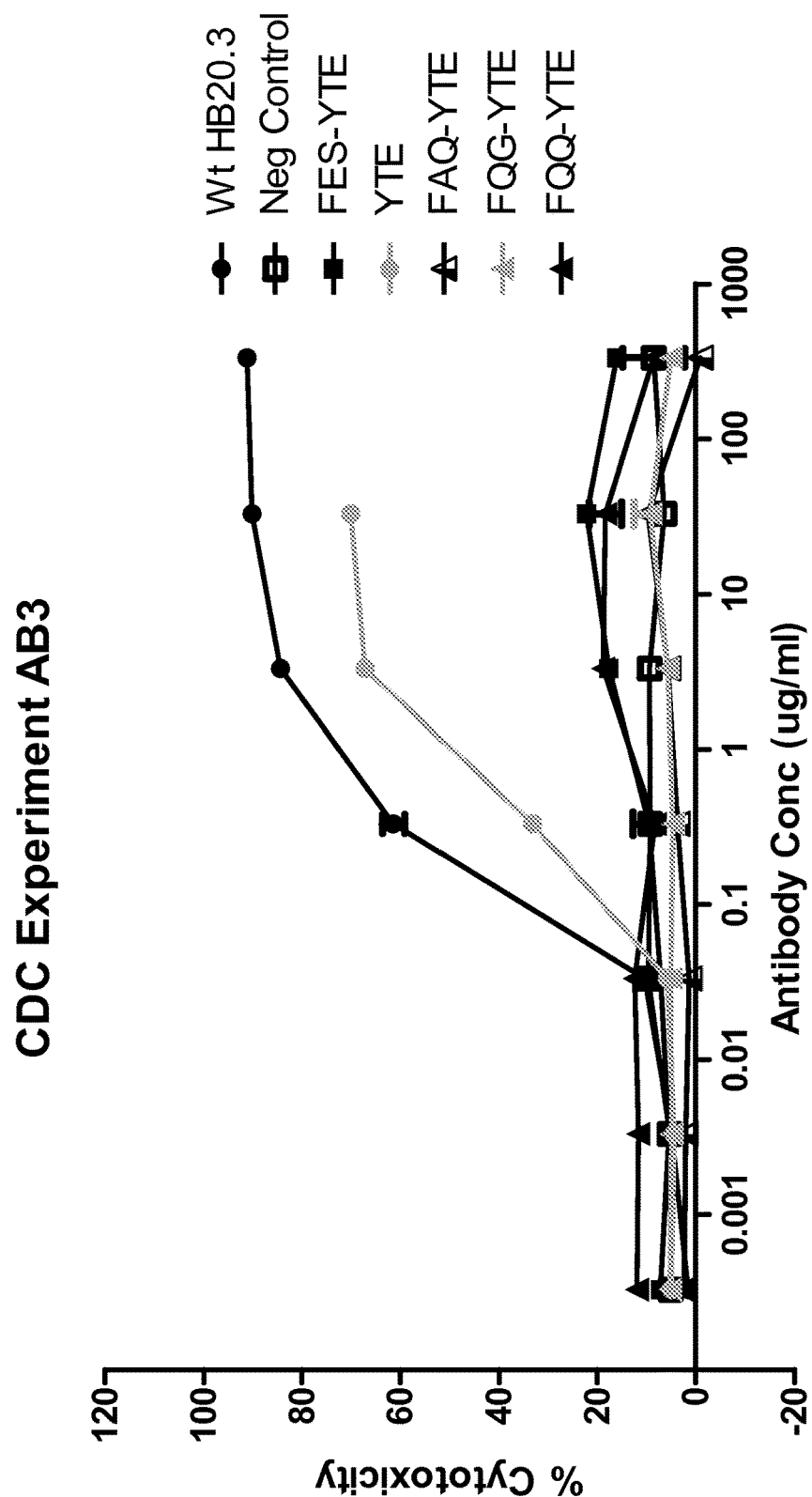

FIG. 4 shows CDC as measured in cytotoxicity assays. The antibody samples corresponded to Ab3 antibodies comprising wild-type (WT) Fc domains, and to Ab3 antibodies comprising FQQ-YTE, FQG-YTE, FAQ-YTE, YTE, or FES-YTE variant Fc domains. A negative control was also used.

Figure 5:
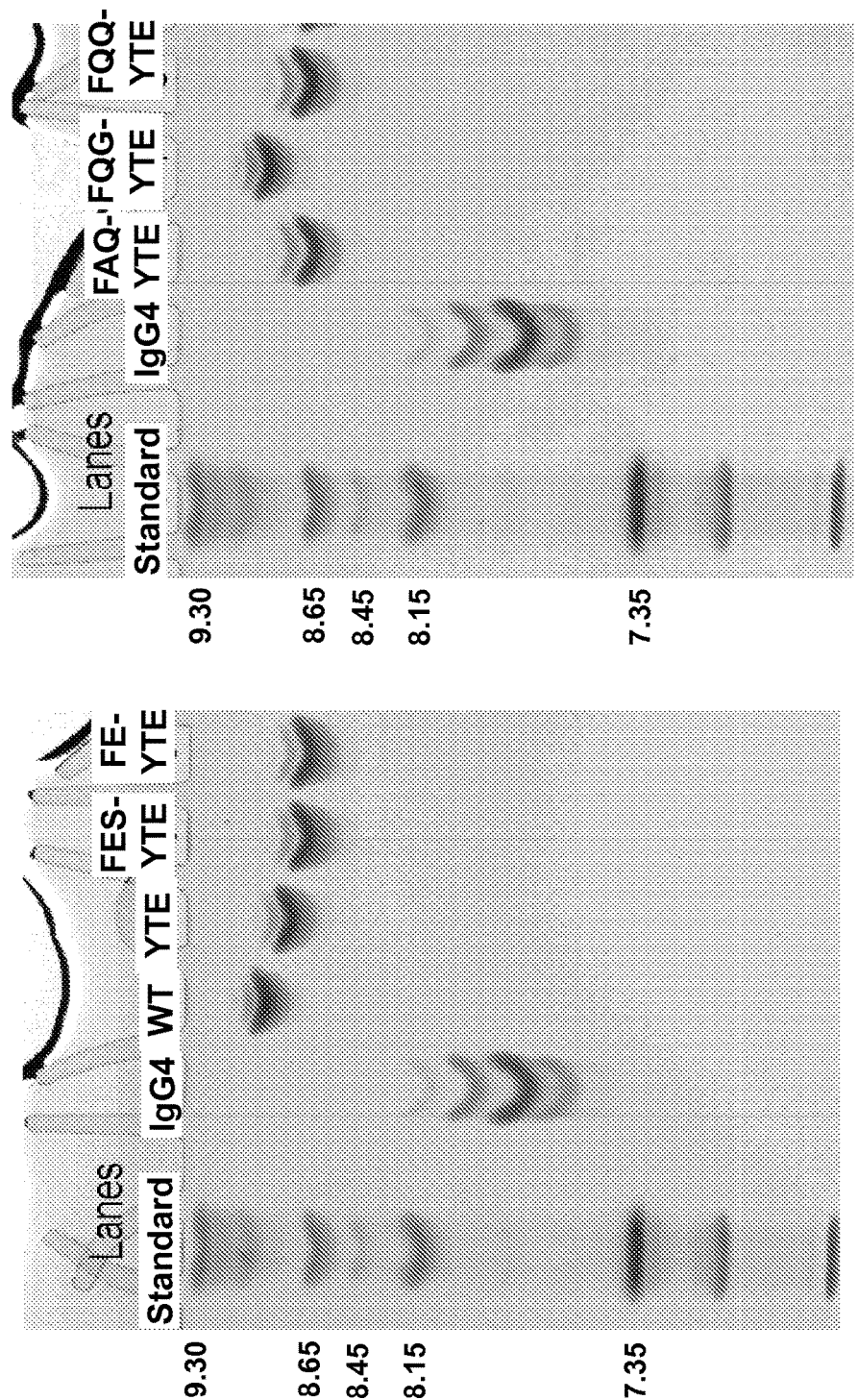

FIG. 5 shows isoelectric focusing (IEF) gels. The antibody samples corresponded to Ab4 antibodies comprising wild-type (WT) Fc domains, and to AM antibodies comprising YTE, FES-YTE, FE-YTE, FAQ-YTE, FQG-YTE, or FQQ-YTE variant Fc domains. An IgG4 control was also included.

FIG. 6A-B shows amino acid sequences and numbering for the CH1 and hinge regions. FIG. 6A shows EU positions 118 to 230; FIG. 6B shows EU positions 231 to 340.

Figure 7:
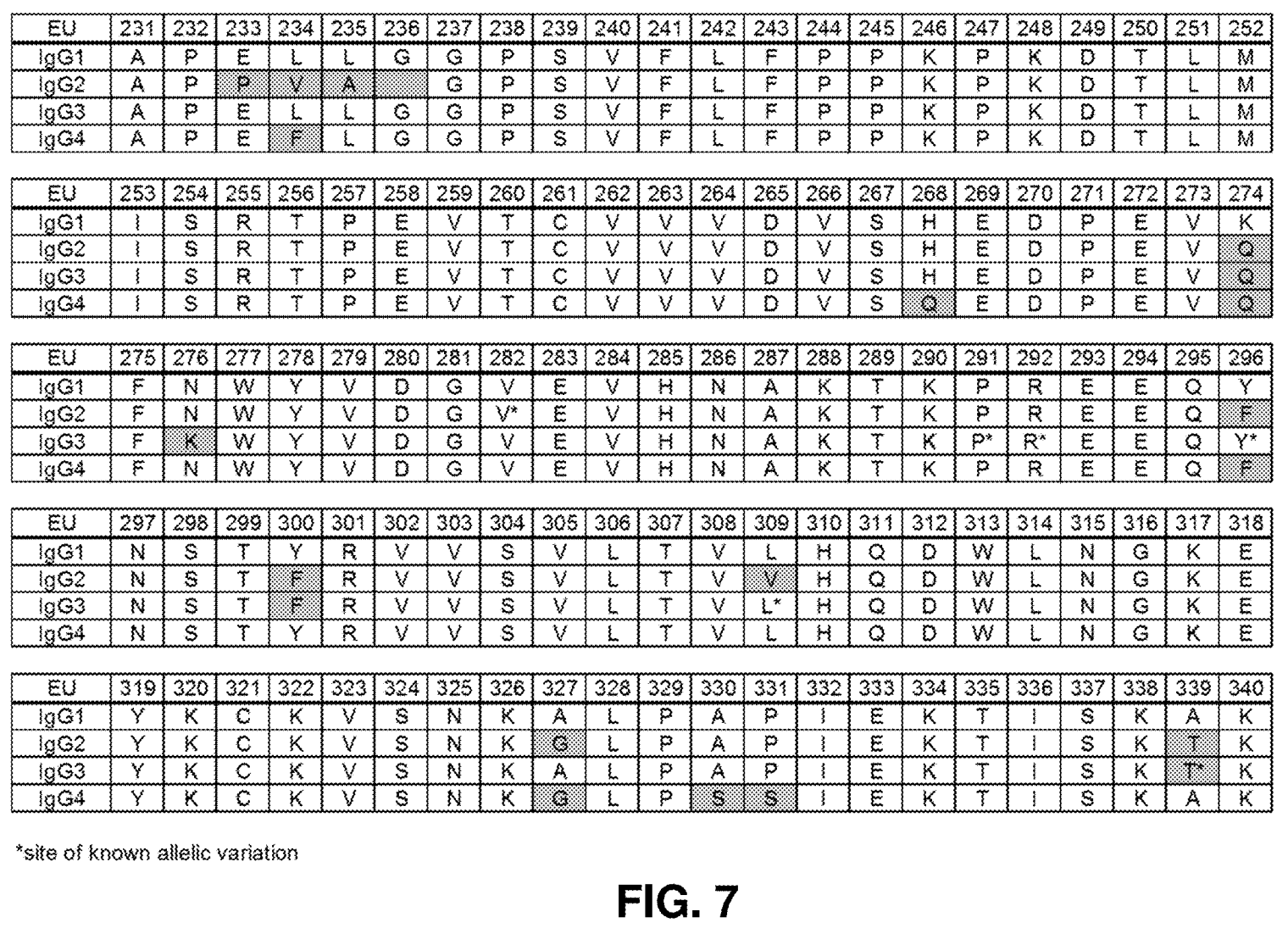

FIG. 7 shows amino acid sequences and numbering for the CH2 and hinge regions region (EU positions 231 to 340).

FIG. 8 shows amino acid sequence and numbering for the CH3 region (EU position 341 to 447).

DETAILED DESCRIPTION

The present disclosure is directed to recombinant polypeptides comprising a variant Fc domain with amino acid substitutions resulting in desired properties, e.g., reduced effector function, and improved plasma half-life, while maintaining stability, e.g., thermal stability. The present disclosure relates in particular to polypeptides, more particularly immunoglobulins, comprising an IgG Fc domain (e.g., a human IgG Fc domain), or a fragment thereof that binds to FcRn (preferably an Fc or hinge-Fc domain) that contains one or more amino acid modifications relative to a wild type IgG, and wherein such modifications reduce or ablate effector function.

In some aspects, the present disclosure particularly relates to the modification of human or humanized IgGs and other bioactive molecules containing FcRn-binding portions of human IgG Fc domains, which have particular use in therapy, prophylaxis and diagnosis. In some aspects, the polypeptides comprise an IgG Fc domain, or fragment thereof that binds to FcRn (preferably an Fc or hinge-Fc domain) comprising modifications ablating effector function, as well as modifications that increase the plasma half life of the polypeptide.

Definitions

It is to be noted that the term "a" or "an" entity refers to one or more of that entity; for example, "a polypeptide sequence," is understood to represent one or more polypeptide sequences. As such, the terms "a" (or "an"), "one or more," and "at least one" can be used interchangeably herein. Furthermore, "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects, which can be had by reference to the specification as a whole. Accordingly, the terms defined immediately below are more fully defined by reference to the specification in its entirety.

It is understood that wherever aspects are described herein with the language "comprising," otherwise analogous aspects described in terms of "consisting of" and/or "consisting essentially of" are also provided.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter codes.

As used herein, the term "polypeptide" refers to a molecule composed of monomers (amino acids) linearly linked by amide bonds (also known as peptide bonds). The term "polypeptide" refers to any chain or chains of two or more amino acids, and does not refer to a specific length of the product. As used herein the term "protein" is intended to encompass a molecule comprised of one or more polypeptides, which can in some instances be associated by bonds other than amide bonds. On the other hand, a protein can also be a single polypeptide chain. In this latter instance the single polypeptide chain can in some instances comprise two or more polypeptide subunits fused together to form a protein. The terms "polypeptide" and "protein" also refer to the products of post-expression modifications, including without limitation glycosylation, acetylation, phosphorylation, amidation, derivatization by known protecting/blocking groups, proteolytic cleavage, or modification by non-naturally occurring amino acids. A polypeptide or protein can be derived from a natural biological source or produced by recombinant technology, but is not necessarily translated from a designated nucleic acid sequence. It can be generated in any manner, including by chemical synthesis.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cells or compositions include those which have been purified to a degree that they are no longer in a form in which they are found in nature. In some aspects, an antibody, polynucleotide, vector, cell, or composition which is isolated is substantially pure.

A "recombinant" polypeptide or protein refers to a polypeptide or protein produced via recombinant DNA technology. Recombinantly produced polypeptides and proteins expressed in host cells are considered isolated for the purpose of the present disclosure, as are native or recombinant polypeptides which have been separated, fractionated, or partially or substantially purified by any suitable technique.

Also included in the present disclosure are fragments, variants, or derivatives of polypeptides, and any combination thereof. The term "fragment" when referring to polypeptides and proteins of the present disclosure include any polypeptides or proteins which retain at least some of the properties of the reference polypeptide or protein. Fragments of polypeptides include proteolytic fragments, as well as deletion fragments.

The term "variant" as used herein refers to a polypeptide sequence that differs from that of a parent polypeptide sequence by virtue of at least one amino acid modification. The parent polypeptide can be a naturally occurring polypeptide, i.e., a "wild-type" ("WT") polypeptide, or can be a modified version of a wild-type polypeptide. The term variant polypeptide can refer to the polypeptide itself, a composition comprising the polypeptide, or the amino sequence that encodes it. Preferably, the variant polypeptide (e.g., a polypeptide comprising a variant IgG Fc domain) has at least one amino acid modification compared to the parent polypeptide, e.g., from about one to about ten amino acid modifications, and preferably from about one to about six amino acid modifications compared to the parent polypeptide. The variant polypeptide sequence herein will generally possess at least about 90% sequence identity with a parent polypeptide sequence, and most generally at least about 95% sequence identity.

Variants of polypeptides or proteins of the present disclosure include fragments as described above, and also polypeptides or proteins with altered amino acid sequences due to amino acid substitutions, deletions, or insertions. Variants can be naturally or non-naturally occurring. Non-naturally occurring variants can be produced using art-known mutagenesis techniques. Variant polypeptides can comprise conservative or non-conservative amino acid substitutions, deletions or additions.

The term "derivatives" as applied to polypeptides or proteins refers to polypeptides or proteins which have been altered so as to exhibit additional features not found on the native polypeptide or protein. An example of a "derivative" of a variant Fc domain is a fusion or a conjugate with a second polypeptide or another molecule (e.g., a polymer such as PEG, a chromophore, or a fluorophore) or atom (e.g., a radioisotope).

The terms "polynucleotide" or "nucleotide" as used herein are intended to encompass a singular nucleic acid as well as plural nucleic acids, and refers to an isolated nucleic acid molecule or construct, e.g., messenger RNA (mRNA) or plasmid DNA (pDNA). In certain aspects, a polynucleotide comprises a conventional phosphodiester bond or a non-conventional bond (e.g., an amide bond, such as found in peptide nucleic acids (PNA)).

The term "nucleic acid" refers to any one or more nucleic acid segments, e.g., DNA or RNA fragments, present in a polynucleotide. When applied to a nucleic acid or polynucleotide, the term "isolated" refers to a nucleic acid molecule, DNA or RNA, which has been removed from its native environment, for example, a recombinant polynucleotide encoding an polypeptide comprising a variant Fc domain contained in a vector is considered isolated for the purposes of the present disclosure. Further examples of an isolated polynucleotide include recombinant polynucleotides maintained in heterologous host cells or purified (partially or substantially) from other polynucleotides in a solution. Isolated RNA molecules include in vivo or in vitro RNA transcripts of polynucleotides of the present disclosure. Isolated polynucleotides or nucleic acids according to the present disclosure further include such molecules produced synthetically. In addition, a polynucleotide or a nucleic acid can include regulatory elements such as promoters, enhancers, ribosome binding sites, or transcription termination signals.

As used herein, the term "host cell" refers to a cell or a population of cells harboring or capable of harboring a recombinant nucleic acid. Host cells can be a prokaryotic cells (e.g., *E. coli*), or alternatively, the host cells can be eukaryotic, for example, fungal cells (e.g., yeast cells such as *Saccharomyces cerivisiae, Pichia pastoris,* or *Schizosaccharomyces pombe*), and various animal cells, such as insect cells (e.g., Sf-9) or mammalian cells (e.g., HEK293F, CHO, COS-7, NIH-3T3).

The present disclosure also encompasses polypeptides comprising a variant IgG Fc domain comprising one or more conservative amino acid substitutions. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another aspect, a string of amino acids can be conservatively replaced with a structurally similar string that differs in order and/or composition of side chain family members.

The term "percent sequence identity" between two polynucleotide or polypeptide sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence.

The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences can be accomplished using readily available software both for online use and for download. Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

One skilled in the art will appreciate that the generation of a sequence alignment for the calculation of a percent sequence identity is not limited to binary sequence-sequence comparisons exclusively driven by primary sequence data. Sequence alignments can be derived from multiple sequence alignments. One suitable program to generate multiple sequence alignments is ClustalW2, available from www.clustal.org. Another suitable program is MUSCLE, available from www.drive5.com/muscle/. ClustalW2 and MUSCLE are alternatively available, e.g., from the EBI.

It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculate percent sequence identity can be curated either automatically or manually.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof, based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc. The terms "antibody" or "immunoglobulin," as used interchangeably herein, include whole antibodies and any antigen binding fragment or single chains thereof.

The term "IgG" as used herein refers to a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, and IgG3.

The term "antigen binding fragment" refers to a portion of an intact antibody and refers to the antigenic determining variable regions of an intact antibody. It is known in the art that the antigen binding function of an antibody can be performed by fragments of a full-length antibody. Examples of antibody fragments include, but are not limited to Fab, Fab', F(ab')2, and Fv fragments, linear antibodies, single chain antibodies, and multispecific antibodies formed from antibody fragments.

The term "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of ways including, but not limited to, by hybridoma, phage selection, recombinant expression, and transgenic animals.

The term "human antibody" refers to an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides. The term "humanized antibody" refers to an antibody derived from a non-human (e.g., murine) immunoglobulin, which has been engineered to contain minimal non-human (e.g., murine) sequences.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc) with the desired specificity, affinity, and capability while the constant regions are homologous to the sequences in antibodies derived from another (usually human) to avoid eliciting an immune response in that species.

The term "EU index as in Kabat" refers to the numbering system of the human IgG1 EU antibody described in Kabat et al., Sequences of Immunological Interest, 5th Ed. Public Health Service, National Institutes of Health, Bethesda, Md. (1991). All amino acid positions referenced in the present application refer to EU index positions. For example, both "L234" and "EU L234" refer to the amino acid leucine at position 234 according to the EU index as set forth in Kabat.

The terms "Fc domain" and "IgG Fc domain" as used herein refer to the portion of an immunoglobulin, e.g., an IgG molecule, that correlates to a crystallizable fragment obtained by papain digestion of an IgG molecule. The Fc region comprises the C-terminal half of two heavy chains of an IgG molecule that are linked by disulfide bonds. It has no antigen binding activity but contains the carbohydrate moiety and binding sites for complement and Fc receptors, including the FcRn receptor (see below). For example, an Fc domain contains the entire second constant domain CH2 (residues at EU positions 231-340 of IgG1, see, e.g., FIG. 7) and the third constant domain CH3 (residues at EU positions 341-447 of human IgG1, see, e.g., FIG. 8).

Fc can refer to this region in isolation, or this region in the context of an antibody, antibody fragment, or Fc fusion protein. Polymorphisms have been observed at a number of positions in Fc domains, including but not limited to EU positions 270, 272, 312, 315, 356, and 358, and thus slight differences between the sequences presented in the instant application and sequences known in the art can exist. Thus, a "wild type IgG Fc domain" or "WT IgG Fc domain" refers to any naturally occurring IgG Fc region (i.e., any allele). Myriad Fc mutants, Fc fragments, Fc variants, and Fc derivatives are described, e.g., in U.S. Pat. Nos. 5,624,821; 5,885,573; 5,677,425; 6,165,745; 6,277,375; 5,869,046; 6,121,022; 5,624,821; 5,648,260; 6,528,624; 6,194,551; 6,737,056; 7,122,637; 7,183,387; 7,332,581; 7,335,742; 7,371,826; 6,821,505; 6,180,377; 7,317,091; 7,355,008; U.S. Patent publication 2004/0002587; and PCT Publication Nos. WO 99/058572, WO 2011/069164 and WO 2012/006635.

The sequences of the heavy chains of human IgG1, IgG2, IgG3 and IgG4 can be found in a number of sequence databases, for example, at the Uniprot database (www.uniprot.org) under accession numbers P01857 (IGHG1_HUMAN), P01859 (IGHG2_HUMAN), P01860 (IGHG3_HUMAN), and P01861 (IGHG1_HUMAN), respectively. FIGS. 6-8 present the amino acid sequences and numbering for the IgG heavy chains from human IgG1 (SEQ ID NO:1), IgG2 (SEQ ID NO:2), IgG3 (SEQ ID NO:3) and IgG4 (SEQ ID NO:4) according to the EU index as set forth in Kabat. Residues which differ among IgG subclasses are shaded and sites of known allelic variation are indicated by an asterisk (*).

The terms "variant IgG Fc domain" and "IgG Fc variant domain" as used herein refers to an IgG Fc domain comprising one or more amino acid substitutions, deletions, insertions or modifications introduced at any position within the Fc domain. In certain aspects a variant IgG Fc domain comprises one or more amino acid substitutions resulting in decreased or ablated binding affinity for an FcγR and/or C1q as compared to the wild type Fc domain not comprising the one or more amino acid substitutions. Fc binding interactions are essential for a variety of effector functions and downstream signaling events including, but not limited to, antibody dependent cell-mediated cytotoxicity (ADCC) and complement dependent cytotoxicity (CDC). Accordingly, in certain aspects, a polypeptide comprising a variant IgG Fc domain (e.g., an antibody, fusion protein or conjugate) can exhibit altered binding affinity for at least one or more Fc ligands (e.g., FcγRs) relative to a corresponding polypeptide having the same amino acid sequence but not comprising the one or more amino acid substitution, deletion, insertion or modification such as, for example, an unmodified Fc region containing naturally occurring amino acid residues at the corresponding position in the Fc region.

The terms "YTE" or "YTE mutant" refer to a set of mutations in an IgG1 Fc domain that results in an increase in the binding to human FcRn and improves the serum half-life of the antibody having the mutation. A YTE mutant comprises a combination of three "YTE mutations": M252Y, S254T, and T256E, wherein the numbering is according to the EU index as in Kabat, introduced into the heavy chain of an IgG. See U.S. Pat. No. 7,658,921, which is incorporated by reference herein. The YTE mutant has been shown to increase the serum half-life of antibodies compared to wild-type versions of the same antibody. See, e.g., Dall'Acqua et al., J. Biol. Chem. 281:23514-24 (2006) and U.S. Pat. No. 7,083,784, which are hereby incorporated by reference in their entireties. A "Y" mutant comprises only the M256Y mutations similarly a "YT" mutation comprises only the M252Y and S254T and a "YE" mutation comprises only the M252Y and T256E. It is specifically contemplated that other mutations may be present at EU positions 252 and/or 256. In certain aspects, the mutation at EU position 252 may be M252F, M252S, M252W or M252T and/or the mutation at EU position 256 may be T256S, T256R, T256Q or T256D.

The terms "FES" or "FES mutant" refer to a set of mutations in an IgG Fc domain that result in ablation of effector function, namely elimination of the Fc domain's ability to mediate antibody-dependent cell-mediate cytotoxicity and complement-mediated cytotoxicity. In certain aspects, a FES mutant can comprise a combination of three "FES mutations": L234F, L235E, and P331S, where the numbering is according to the EU index as in Kabat. These mutations cause a profound decrease Fc domain binding to human FcγRI (CD64), FcγRIIA (CD32A), FcγRIII (CD16) and C1q. See, e.g., US 2011/0059078 and Oganesyan et al. Acta Crystallographica D 64:700-704 (2008), which are hereby incorporated by reference in their entireties. An "FE" mutant comprises only the L234F and L235E mutations.

The term "FES-YTE IgG Fc domain" refers to a wild type IgG Fc domain comprising the three "FES" mutations (L234F/L235E/P331S) and the three "YTE" mutations (M252Y/S254T/T256E), where all the numbering is according to the EU index as in Kabat. As demonstrated herein, when FES and YTE mutations are combined (e.g., in a "FES-YTE" Fc domain), there is a considerable reduction in protein stability when compared to the corresponding polypeptide without such set of mutations (see, Example 1 below).

The term "Fc fusion" as used herein refers to a protein in which one or more polypeptides or small molecules are operably linked to an Fc domain or a variant or derivative thereof. An Fc fusion combines the Fc region of an immunoglobulin with a fusion partner, which in general can be any protein or small molecule. The role of the non-Fc part of an Fc fusion, i.e., the fusion partner, can be to mediate target binding, and thus it can be functionally analogous to the variable regions of an antibody.

The term "parent" polypeptide as used herein refers to a polypeptide (e.g., a parent Fc domain, or a polypeptide comprising an Fc domain such as antibody or Fc fusion) that is subsequently modified to generate a variant (e.g., a variant Fc domain, or a variant polypeptide comprising an Fc domain such as a variant antibody or a variant Fc fusion). The parent polypeptide can be a naturally occurring polypeptide (e.g., a wild type Fc domain), or a variant or engineered version of a naturally occurring polypeptide (e.g., a YTE Fc domain and/or a FES-YTE Fc domain). The term parent polypeptide can refer to the polypeptide itself, compositions that comprise the parent polypeptide, or the amino acid sequence that encodes it. Accordingly, by "parent Fc domain" as used herein is meant a Fc domain that is modified to generate a variant, and by "parent antibody" as used herein is meant an antibody that is modified to generate a variant antibody comprising an IgG variant Fc domain.

The term "IgG Fc variant domain containing polypeptide" as used herein refers to a polypeptide comprising a variant IgG Fc domain as defined above.

An "Fc variant" comprises an Fc domain and can exist alone or in the context of an antibody, Fc fusion, isolated Fc, Fc fragment, or other polypeptide. Fc variants can refer to the Fc polypeptide itself, compositions comprising the Fc variant polypeptide, or the amino acid sequence that encodes it. The variant IgG Fc domains described herein are defined according to the amino acid modifications that compose them. For all amino acid positions discussed herein, numbering is always according to the EU index as in Kabat. Thus, for example, M252Y is an Fc variant with the methionine (M) at EU position 252 substituted with tyrosine (Y) relative to the parent Fc domain. Likewise, e.g., M252Y/S254T/T256E defines a variant Fc variant with substitutions at EU positions 252 (M to Y), 254 (S to T), and 256 (T to E) relative to the parent Fc domain. A variant can also be designated according to its final amino acid composition in the mutated EU amino acid positions. For example, the M252Y/S254T/T256E mutant can be referred to as YTE. It is noted that the order in which substitutions are provided is arbitrary, that is to say that, for example, M252Y/S254T/T256E is the same Fc variant as T256E/S254T/M252Y.

The terms "Fc gamma receptor" or "FcγR" as used herein refer to any member of the family of proteins that bind the IgG antibody Fc region and are encoded by the FcγR genes. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2), as well as any undiscovered human FcγRs or FcγR isoforms or allotypes. An FcγR can be from any organism, including but not limited to humans, mice, rats, rabbits, and monkeys. Mouse FcγRs include but are not limited to FcγRI (CD64), FcγRII (CD32), FcγRIII (CD16), and FcγRIII-2 (CD16-2), as well as any undiscovered mouse FcγRs or FcγR isoforms or allotypes.

The term "FcRn" or "FcRn receptor" as used herein refers to an Fc receptor ("n" indicates neonatal) which is known to be involved in transfer of maternal IgGs to a fetus through the human or primate placenta, or yolk sac (rabbits) and to a neonate from the colostrum through the small intestine. It is also known that FcRn is involved in the maintenance of constant serum IgG levels by binding the IgG molecules and recycling them into the serum. The binding of FcRn to IgG molecules is pH-dependent with optimum binding at pH 6.0 and weak binding at pH>7.0. Whereas the binding of IgGs to FcγR receptors can trigger effector function (e.g., ADCC), binding to FcRn in a pH dependent manner can prolong the half-life on IgG antibodies in the serum. Effector function can be undesirable for a molecule with a prolonged half-life in serum.

The term "effector function" as used herein refers to a biochemical event that results from the interaction of an Fc domain with an Fc receptor or ligand. Effector functions include but are not limited to ADCC, ADCP, and CDC. By "effector cell" as used herein is meant a cell of the immune system that expresses or one or more Fc receptors and mediates one or more effector functions. Effector cells include but are not limited to monocytes, macrophages, neutrophils, dendritic cells, eosinophils, mast cells, platelets, B cells, large granular lymphocytes, Langerhans' cells, natural killer (NK) cells, and γδ T cells, and can be from any organism included but not limited to humans, mice, rats, rabbits, and monkeys.

The terms "antibody-dependent cell-mediated cytotoxicity" or "ADCC" refer to a form of cytotoxicity in which a polypeptide comprising an Fc domain, e.g., an antibody, bound onto Fc receptors (FcRs) present on certain cytotoxic cells (e.g., primarily NK cells, neutrophils, and macrophages) and enables these cytotoxic effector cells to bind specifically to an antigen-bearing "target cell" and subsequently kill the target cell with cytotoxins. (Hogarth et al., Nature review Drug Discovery 2012, 11:313) It is contemplated that, in addition to antibodies and fragments thereof, other polypeptides comprising Fc domains, e.g., Fc fusion proteins and Fc conjugate proteins, having the capacity to bind specifically to an antigen-bearing target cell will be able to effect cell-mediated cytotoxicity.

For simplicity, the cell-mediated cytotoxicity resulting from the activity of a polypeptide comprising an Fc domain is also referred to herein as ADCC activity. The ability of any particular polypeptide of the present disclosure to mediate lysis of the target cell by ADCC can be assayed. To assess ADCC activity, a polypeptide of interest (e.g., an antibody) is added to target cells in combination with immune effector cells, resulting in cytolysis of the target cell. Cytolysis is generally detected by the release of label (e.g., radioactive substrates, fluorescent dyes or natural intracellular proteins) from the lysed cells. Useful effector cells for such assays include peripheral blood mononuclear cells (PBMC) and Natural Killer (NK) cells. Specific examples of in vitro ADCC assays are described in Bruggemann et al., *J. Exp. Med.* 166:1351 (1987); Wilkinson et al., *J. Immunol. Methods* 258:183 (2001); Patel et al., *J. Immunol. Methods* 184:29 (1995). Alternatively, or additionally, ADCC activity of the antibody of interest can be assessed in vivo, e.g., in an animal model such as that disclosed in Clynes et al., *Proc. Natl. Acad. Sci. USA* 95:652 (1998).

The term "CDC" as used herein refers to complement dependent cytotoxicity, i.e., a biochemical event of targeted cell destruction mediated by the complement system.

The terms "half-life" or "in vivo half-life" as used herein refer to the biological half-life of a particular type of polypeptide of the present disclosure in the circulation of a given animal and is represented by a time required for half the quantity administered in the animal to be cleared from the circulation and/or other tissues in the animal.

The term "subject" as used herein refers to any animal (e.g., a mammal), including, but not limited to humans, non-human primates, rodents, and the like, which is to be the recipient of a particular treatment. The terms "subject" and "patient" are used interchangeably herein in reference to a human subject.

The term "pharmaceutical composition" as used herein refers to a preparation which is in such form as to permit the biological activity of the active ingredient to be effective, and which contains no additional components which are unacceptably toxic to a subject to which the composition would be administered. Such composition can be sterile.

An "effective amount" of a polypeptide, e.g., an antibody, as disclosed herein is an amount sufficient to carry out a specifically stated purpose. An "effective amount" can be determined empirically and in a routine manner, in relation to the stated purpose. The term "therapeutically effective amount" as used herein refers to an amount of a polypeptide, e.g., an antibody, or other drug effective to "treat" a disease or disorder in a subject or mammal.

The term "label" when used herein refers to a detectable compound or composition which is conjugated directly or indirectly to a polypeptide, e.g., an antibody, so as to generate a "labeled" polypeptide. The label can be detectable by itself (e.g., radioisotope labels or fluorescent labels) or, in the case of an enzymatic label, can catalyze chemical alteration of a substrate compound or composition which is detectable.

Terms such as "treating" or "treatment" or "to treat" or "alleviating" or "to alleviate" refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented.

The term "vector" means a construct, which is capable of delivering, and in some aspects, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

Variant IgG Fc Domains

In some aspects, variant IgG Fc domains are provided which comprise mutations that confer extended serum half-life and greatly diminish or completely abolish effector function. These variant IgG Fc domains can be introduced, e.g., to existing therapeutic antibodies to favorably alter pharmacokinetic parameters (as well as enable less frequent dosing) while lessening undesirable adverse ADCC and CDC activity.

The YTE set of mutations (corresponding to the EU M252Y, EU S254T, and EU T256E substitutions) (Dall'Acqua et al., J. Immunol. 169:5171-80 2002; Dall'Acqua et al., J. Biol. Chem. 281:23514-24 (2006)) located in the CH2 region of the Fc domain has been shown to enhance antibody serum half-life in cynomolgous monkeys by improving binding to the recycling receptor FcRn at pH 6. The FES triple mutation (corresponding to the EU L234F, EU L235E, and EU P331S set of substitutions) also located in the CH2 region of the Fc domain can abrogate FCγR and C1q binding resulting in an antibody unable to elicit ADCC or CDC (Oganesyan et al., Acta Crystallogr. D 64:700-704 (2008)). As demonstrated herein, combining these mutations in a variant Fc domain, e.g., a variant Fc domain in an antibody result in an Fc domain having reduced thermal stability compared to a wild type parent molecule, e.g., a wild type IgG1 Fc.

As demonstrated herein, specific IgG Fc domain amino acid substitutions at EU positions 234, 235, and 322 or 331 (e.g., L234F/L235Q/K322Q or L234F/L235Q/P331G) greatly reduce or eliminate ADCC and CDC. When these specific IgG Fc domain amino acid substitutions at EU positions 234, 235, and 322 or 331 are combined with YTE mutations, the resulting variant Ig Fc domains show ADCC and CDC properties equivalent to those of the FES-YTE mutants but also display greatly improved thermal stability characteristics.

Accordingly, in some aspects a polypeptide is provided which comprises a variant IgG Fc domain (e.g., a variant of a human IgG domain or a FcRn binding fragment thereof) comprising:

(i) a phenylalanine (F) amino acid at EU position 234,
(ii) an alanine (A), asparagine (N), phenylalanine (F), a glutamine (Q) or a valine (V) amino acid at EU position 235, and
(iii) an alanine (A), aspartic acid (D), glutamic acid (E), histidine (H), asparagine (N), or glutamine (Q) amino acid at EU position 322, or—in the alternative—an alanine (A) or glycine (G) amino acid at EU position 331.

In one aspect, a polypeptide is provided which comprises a variant IgG Fc domain which comprises a phenylalanine (F) amino acid at EU position 234, a glutamine (Q) amino acid at EU position 235, and a glutamine (Q) amino acid at EU position 322. Hereinafter, this variant IgG Fc domain and set of amino acid substitutions will be referred to as "FQQ."

In another aspect, a polypeptide is provided which comprises a variant IgG Fc domain, which comprises a phenylalanine (F) amino acid at EU position 234, a glutamine (Q) amino acid at EU position 235 and a glycine (G) amino acid at EU position 331. Hereinafter, this variant IgG Fc domain and set of amino acid substitutions will be referred to as "FQG."

In yet another aspect, a polypeptide is provided which comprises a variant IgG Fc domain, which comprises a phenylalanine (F) amino acid at EU position 234, an alanine (A) amino acid at EU position 235, and a glutamine (Q) amino acid at EU position 322. Hereinafter, this variant IgG Fc domain and set of amino acid substitutions will be referred to as "FAQ."

In certain aspects, a polypeptide is provided which comprises a variant IgG Fc domain, which comprises three of the amino acid substitutions disclosed above at EU positions 234, 235, and 322 or 331, and further comprises one or more amino acid substitutions at any one of EU positions 252, 254, or 256. Thus, in one aspect, a polypeptide is provided which comprises a variant IgG Fc domain (e.g., a FQQ, FQG or FAQ variant IgG Fc domain) which further comprises a tyrosine (Y) amino acid at EU position 252, or a phenylalanine (F) amino acid at EU position 252, or a serine (S) amino acid at EU position 252, or a tryptophan (W) amino acid at EU position 252 or a threonine (T) amino acid at EU position 252. In a particular aspect, a polypeptide is provided which comprises a variant IgG Fc domain (e.g., a FQQ, FQG or FAQ variant IgG Fc domain) which further comprises a tyrosine (Y) amino acid at EU position 252.

In another aspect, a polypeptide is provided which comprises a variant IgG Fc domain (e.g., a FQQ, FQG or FAQ variant IgG Fc domain) which further comprises a threonine (T) amino acid at EU position 254. In another aspect, a polypeptide is provided which comprises a variant IgG Fc domain (e.g., a FQQ, FQG or FAQ variant IgG Fc domain) which further comprises a glutamic acid (E) amino acid at EU position 256, or a serine (S) amino acid at EU position 256, or a arginine (R) amino acid at EU position 256, or a glutamine (Q) amino acid at EU position 256, or an aspartate (D) amino acid at EU position 256. In a particular aspect, a polypeptide is provided which comprises a variant IgG Fc domain (e.g., a FQQ, FQG or FAQ variant IgG Fc domain) which further comprises a glutamic acid (E) amino acid at EU position 256.

In certain aspects, a polypeptide is provided which comprises three of the amino acids substitutions disclosed above at EU positions 234, 235, and 322 or 331, and further comprises substitutions at two positions selected from the group consisting of EU positions 252, 254, and 256. Accordingly, in one aspect, a polypeptide is provided which comprises a variant IgG Fc domain (e.g., a FQQ, FQG or FAQ variant IgG Fc domain) further comprising a tyrosine (Y) amino acid at EU position 252 and a threonine (T) amino acid at EU position 254.

In another aspect, a polypeptide is provided which comprises a variant IgG Fc domain (e.g., a FQQ, FQG or FAQ variant IgG Fc domain) further comprising a threonine (T) amino acid at EU position 254 and a glutamic acid (E) amino acid at EU position 256. In yet another aspect, a polypeptide is provided which comprises a variant IgG Fc domain (e.g., a FQQ, FQG or FAQ variant IgG Fc domain) further comprising a tyrosine (Y) amino acid at EU position 252 and a glutamic acid (E) amino acid at EU position 256.

In certain aspects, a polypeptide is provided which comprises a variant IgG Fc domain with three of the amino acids disclosed above at EU positions 234, 235, and 322 or 331 (e.g., a FQQ, FQG or FAQ variant IgG Fc domain), wherein the variant IgG Fc domain further comprises a tyrosine (Y) amino acid at EU position 252, a threonine (T) amino acid at EU position 254, and a glutamic acid (E) amino acid at EU position 256.

In some aspects, a polypeptide is provided which comprises a variant IgG Fc domain comprising a phenylalanine (F) amino acid at EU position 234, a glutamine (Q) amino acid at EU position 235, a glutamine (Q) amino acid at EU position 322, a tyrosine (Y) amino acid at EU position 252, a threonine (T) amino acid at EU position 254, and a glutamic acid (E) amino acid at EU position 256.

In another aspect, a polypeptide is provided which comprises a variant IgG Fc domain comprising a phenylalanine (F) at EU position 234, a glutamine amino (Q) amino acid at EU position 235, a glycine (G) amino acid at EU position 331, a tyrosine (Y) amino acid at EU position 252, a threonine (T) amino acid at EU position 254, and a glutamic acid (E) amino acid at EU position 256. In yet another aspect, a polypeptide is provided which comprises a variant IgG Fc domain comprising a phenylalanine (F) at EU position 234, an alanine (A) at EU position 235, a glutamine (Q) amino acid at EU position 322, a tyrosine (Y) amino acid at EU position 252, a threonine (T) amino acid at EU position 254, and a glutamic acid (E) amino acid at EU position 256. Thus, the present disclosure encompasses, but it is not limited to, a polypeptide comprising a variant IgG Fc domain with FQQ and YTE mutations, a polypeptide comprising a variant IgG Fc domain with FQG and YTE mutations, and a polypeptide comprising a variant IgG Fc domain with FAQ and YTE mutations.

In some aspects, the parent polypeptide of the variant IgG Fc domain already contains one or more of the amino acids corresponding to the substitutions discussed above, e.g., the parent Fc polypeptide can contain a phenylaline (F) at EU position 234 as is found in IgG4. In such aspects, no modification of the amino acid or amino acids already containing one or more of the disclosed substitutions is required.

In some aspects, the variant IgG Fc domain is human. In some other aspects, the variant IgG Fc domain is non-human. Non-human IgG Fc domains can be, e.g., from rodents (e.g., rats or mice), donkey, sheep, rabbit, goat, guinea pig, camel, horse, or chicken. A human variant IgG Fc domain can be, e.g., a subclass $IgG_1$, $IgG_2$, $IgG_3$ or $IgG_4$ Fc domain. When the variant IgG Fc domain is a mouse IgG Fc domain, the domain can be, e.g., a subclass IgG1, IgG2a, IgG2b, or IgG3 domain.

In some aspects, a polypeptide is provided which comprises a variant IgG Fc domain comprising an amino acid sequence selected from the group consisting of SEQ ID NO:9 to SEQ ID NO:32. In some other aspects, a polypeptide is provided which comprises a variant IgG Fc domain consisting of an amino acid sequence selected from the group consisting of SEQ ID NO:9 to SEQ ID NO:32. Based on the teaching provided herein, it will be understood by one of skill in the art that the variant IgG Fc domains provided in SEQ ID NO:9 to SEQ ID NO:32 represent one particular allelic variation. Accordingly, in some aspects, a polypeptide is provided which comprises a different allelic variation of a variant IgG Fc domain as provided in SEQ ID NO:9 to SEQ ID NO:32. Sites of known allelic variation are provided in FIGS. 6-8.

In some aspects, a polypeptide is provided which comprises a variant IgG Fc domain comprising one of the amino acid sequences disclosed in TABLE 1 (SEQ ID NO:37 to SEQ ID NO: 40). In other aspects, a polypeptide is provided which comprises a variant IgG Fc domain consisting of one of the amino acid sequences disclosed in TABLE 1 (SEQ ID NO:37 to SEQ ID NO: 40). Based on the teaching provided herein, it will be understood by one of skill in the art that the variant IgG Fc domains provided in SEQ ID NO:37 to SEQ ID NO: 40 represent one particular allelic variation. Accordingly, in some aspects, a polypeptide is provided which comprises a different allelic variation of a variant IgG Fc domain as provided in SEQ ID NO:37 to SEQ ID NO: 40. Sites of known allelic variation are provided in FIGS. 6-8.

TABLE 1

Variant IgG Fc Domains.

| Site* | EU Position | Native Amino Acids |  |  |  | Amino Acid Substitution |
|---|---|---|---|---|---|---|
|  |  | IgG1 | IgG2 | IgG3 | IgG4 |  |
| $X_1$ | 234 | L | V | L | F | F |
| $X_2$ | 235 | L | A | L | L | A, N, F, Q, V |
| $X_3$ | 322 | K | K | K | K | A, D, E, H, N, Q |
| $X_4$ | 331 | P | P |  | S | A, G |
| $X_5$ | 252 | M | M | M | M | Y |
| $X_6$ | 254 | S | S | S | S | T |
| $X_7$ | 256 | T | T | T | T | E |

Variant IgG1 Fc Domains (SEQ ID NO: 37)
PAPE$X_1X_2$GGPSVFLFPPKPKDTL$X_5$I$X_6$R$X_7$PEVTCVVVDVSHEDPEVKF
NWYVDGVEVHNAKTKPREEQYNSTYRVVSVLTVLHQDWLNGKEYK$CX_3$VS
NKAL$PX_4$IEKTISKAKGQPREPQVYTLPPSRDELTKNQVSLTCLVKGFY
PSDIAVEWESNGQPENNYKTTPPVLDSDGSFFLYSKLTVDKSRWQQGNVF
SCSVMHEALHNHYTQKSLSLSPGK Variant IgG2 Fc Domains (SEQ ID NO: 38)
PAPP$X_1X_2$GPSVFLFPPKPKDTL$X_5$I$X_6$R$X_7$PEVTCVVVDVSHEDPEVQFN
WYVDGVEVHNAKTKPREEQFNSTFRVVSVLTVVHQDWLNGKEYK$CX_3$VSN
KGL$PX_4$IEKTISKTKGQPREPQVYTLPPSREEMTKNQVSLTCLVKGFYP
SDISVEWESNGQPENNYKTTPPMLDSDGSFFLYSKLTVDKSRWQQGNVFS
CSVMHEALHNHYTQKSLSLSPGK Variant IgG3 Fc Domains (SEQ ID NO: 39)
PAPE$X_1X_2$GGPSVFLFPPKPKDTL$X_5$I$X_6$R$X_7$PEVTCVVVDVSHEDPEVQF
KWYVDGVEVHNAKTKPREEQYNSTFRVVSVLTVLHQDWLNGKEYK$CX_3$VS
NKAL$PX_4$IEKTISKTKGQPREPQVYTLPPSREEMTKNQVSLTCLVKGFY
PSKIAVEWESSGQPENNYNTTPPMLDSDGSFFLYSKLTVDKSRWQQGNIF
SCSVMHEALHNRFTQKSLSLSPGK Variant IgG3 Fc Domains (SEQ ID NO: 40)
PAPE$X_1X_2$GGPSVFLFPPKPKDTL$X_5$I$X_6$R$X_7$PEVTCVVVDVSQEDPEVQF
NWYVDGVEVHNAKTKPREEQFNSTYRVVSVLTVLHQDWLNGKEYK$CX_3$VS
NKGL$PS$X_4$IEKTISKAKGQPREPQVYTLPPSQEEMTKNQVSLTCLVKGFY
PSDIAVEWESNGQPENNYKTTPPVLDSDGSFFLYSRLTVDKSRWQEGNVF
SCSVMHEALHNHYTQKSLSLSLGK

* Amino acids at sites 1 to 7 in the sequences of IgG1, IgG2, IgG3 and IgG4 (boxed positions) can be any native amino acid or amino acid substitution.

Increased Half-Life

In some aspects, a polypeptide comprising a variant IgG Fc domain as disclosed above has an improved pharmacokinetic (PK) property when compared to the same polypeptide comprising a wild-type IgG Fc domain. Examples of such improved PK properties are, e.g., improved binding to an FcRn receptor, or increase in half-life. A polypeptide comprising a variant IgG Fc domain as provided herein can have a half-life (e.g., serum half-life) in a mammal (e.g., a human) of greater than 5 days, greater than 10 days, greater than 15 days, greater than 20 days, greater than 25 days, greater than 30 days, greater than 35 days, greater than 40 days, greater than 45 days, greater than 2 months, greater than 3 months, greater than 4 months, or greater than 5 months.

The increased half-life of an IgG Fc variant domain containing polypeptide provided herein in a mammal results in a higher serum titer of the polypeptide (e.g., an antibody or an antibody fragment), and thus, can reduce the frequency of the administration of the polypeptide and/or reduce the concentration of polypeptide to be administered.

In specific aspects, an IgG Fc variant domain containing polypeptide comprising substitutions at one or more positions selected from the group consisting of EU positions 252, 254, and 256 (e.g., Y, YT, YE, YTE mutations), exhibits an increase in half-life as compared to a parent polypeptide comprising a wild type Fc domain. In other specific aspects, an IgG Fc variant domain containing polypeptide comprising substitutions at one or more positions selected from the group consisting of EU positions 252, 254, and 256 (e.g., Y, YT, YE, YTE mutations), further comprises FQQ, FQG or FAQ mutations, and can exhibit an increase in half-life as well as reduced Fc effector function as compared to a parent polypeptide comprising a wild type Fc domain.

In specific aspects, an IgG Fc variant domain containing polypeptide comprising substitutions at one or more positions selected from the group consisting of EU positions 252, 254, and 256 (e.g., Y, YT, YE, YTE mutations) has a higher affinity for FcRn at pH 6.0 than at pH 7.4 as compared to a parent polypeptide comprising a wild type Fc domain. In other specific aspects, an IgG Fc variant domain comprising substitutions at one or more positions selected from the group consisting of EU positions 252, 254, and 256 (e.g., Y, YT, YE, YTE mutations further comprises FQQ, FQG or FAQ mutations, and can exhibit a higher affinity for FcRn at pH 6.0 than at pH 7.4 and reduced Fc effector function as compared to a parent polypeptide comprising a wild type Fc domain.

Binding to Fc Receptors

An IgG Fc variant domain containing polypeptide provided herein (e.g., an antibody or fragments thereof comprising a variant IgG Fc domain), can further comprise the substitution of at least one amino acid residue located in the Fc region, where such substitution results in reduced or ablated affinity for at least one Fc ligand. As described above, a wild type Fc domain interacts with a number of ligands including but not limited to FcγR receptors (e.g., FcγRIIb, FcγRIIIa) and the complement protein C1q, and these interactions are essential for a variety of effector functions and downstream signaling events including, but not limited to, antibody dependent cell-mediated cytotoxicity (ADCC) and complement dependent cytotoxicity (CDC). Accordingly, in certain aspects, an IgG Fc variant domain containing polypeptide is provided which has reduced or ablated affinity for an Fc ligand responsible for facilitating effector function compared to a molecule having the same amino acid sequence as the disclosed molecule but not comprising the substitution of at least one amino acid residue to the Fc region.

In certain aspects, an IgG Fc variant domain containing polypeptide is provided, comprising one or more of the following properties: reduced or ablated effector function (ADCC and/or CDC), reduced or ablated binding to Fc receptors, or reduced or ablated cytotoxicity. In certain aspects, an IgG Fc variant domain containing polypeptide is provided which exhibits reduced affinity for FcγR receptors (e.g., FcγRIIb, FcγRIIIa) and/or the complement protein C1q. In some aspects, an IgG Fc variant domain containing polypeptide has an increased binding to FcRn receptors.

One skilled in the art will understand that an IgG Fc variant domain containing polypeptide can have altered (relative to an unmodified molecule) FcγR and/or C1q binding properties. Examples of binding properties include but are not limited to, binding specificity, equilibrium dissociation constant ($K_D$), dissociation and association rates ($k_{off}$ and $k_{on}$, respectively), binding affinity and/or avidity. It is known in the art that the equilibrium dissociation constant ($K_D$) is defined as $k_{off}/k_{on}$.

One skilled in the art can determine which kinetic parameter is most important for a given therapeutic or diagnostic application. For example, a modification that reduces binding to one or more positive regulators (e.g., FcγRIIIA) and/or enhanced binding to an inhibitory Fc receptor (e.g., FcγRIIB) would be suitable for reducing ADCC activity. Accordingly, the ratio of binding affinities (e.g., $K_D$) can indicate if the ADCC activity of an IgG Fc variant domain containing polypeptide is enhanced or decreased. Additionally, a modification that reduces binding to C1q would be suitable for reducing or eliminating CDC activity.

The affinities and binding properties of a polypeptide comprising a variant IgG Fc domain for its ligand, can be determined by a variety of in vitro assay methods (biochemical or immunological based assays) known in the art for determining Fc-FcγR interactions, i.e., specific binding of an Fc region to an FcγR including. Such methods include equilibrium methods (e.g., enzyme-linked immunoabsorbent assay (ELISA) or radioimmunoassay (RIA)), or kinetics (e.g., surface plasma resonance, such as BIACORE® analysis), and other methods such as indirect binding assays, competitive inhibition assays, fluorescence resonance energy transfer (FRET), gel electrophoresis and chromatography (e.g., gel filtration).

These and other methods can utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999).

In one aspect, an IgG Fc variant domain containing polypeptide is provides which exhibits reduced binding affinity for one or more Fc receptors including, but not limited to FcγRI (including isoforms FcγRIa, FcγRIb, and FcγRIc); FcγRII (including isoforms FcγRIIa, FcγRIIb, and FcγRIIc); and FcγRIII (including isoforms FcγRIIIa and FcγRIIIb) as compared to a parent polypeptide comprising a wild type Fc domain. In another aspect, the binding of an IgG Fc variant domain containing polypeptide to one or more Fc receptors as noted above is fully ablated.

In one aspect, an IgG Fc variant domain containing polypeptide is provided which exhibits a decreased affinity to FcγRI relative to a parent polypeptide comprising a wild type Fc domain. In another aspect, an IgG Fc variant domain containing polypeptide is provided which exhibits an affinity for FcγRI receptor that is at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold less than a parent polypeptide comprising a wild type Fc domain or is reduced to an undetectable level.

In another aspect, an IgG Fc variant domain containing polypeptide is provided which exhibits an affinity for FcγRI receptor that is at least 90%, at least 80%, at least 70%, at least 60%, at least 50%, at least 40%, at least 30%, at least 20%, at least 10%, or at least 5% less than a parent polypeptide comprising a wild type Fc domain. In some aspects, the FcγRI is isoform FcγRIa. In other aspects, the FcγRI is isoform FcγRIb. In yet another aspect, the FcγRI is isoform FcγRIc.

In one aspect, an IgG Fc variant domain containing polypeptide is provided which exhibits a decreased affinity to FcγRII relative to a parent polypeptide comprising a wild type Fc domain. In another aspect, an IgG Fc variant domain containing polypeptide is provided which exhibits an affinity for FcγRII receptor that is at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold less than a parent polypeptide comprising a wild type Fc domain.

In another aspect, an IgG Fc variant domain containing polypeptide is provided which exhibits an affinity for FcγRII receptor that is at least 90%, at least 80%, at least 70%, at least 60%, at least 50%, at least 40%, at least 30%, at least 20%, at least 10%, or at least 5% less than a parent polypeptide comprising a wild type Fc domain. In some aspects, the FcγRII is isoform FcγRIIa. In another aspect, the FcγRIIa isoform is allotype H131. In yet another aspect, the FcγRIIa isoform is allotype R131. In other aspects, the FcγRII is isoform FcγRIIb. In some aspects, the FcγRIIb isoform is FcγRIIb-1. In other aspects, the FcγRIIb isoform is FcγRIIb-2. In yet another aspect, the FcγRII is isoform FcγRIIc.

In one aspect, an IgG Fc variant domain containing polypeptide is provided which exhibits a decreased affinity to FcγRIII relative to a parent polypeptide comprising a wild type Fc domain. In another aspect, an IgG Fc variant domain containing polypeptide is provided which exhibits an affinity for FcγRIII receptor that is at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold less than a parent polypeptide comprising a wild type Fc domain.

In another aspect, an IgG Fc variant domain containing polypeptide is provided which exhibits an affinity for FcγRIII receptor that is at least 90%, at least 80%, at least 70%, at least 60%, at least 50%, at least 40%, at least 30%, at least 20%, at least 10%, or at least 5% less than a parent polypeptide comprising a wild type Fc domain. In some aspects, the FcγRIII is isoform FcγRIIIa. In other aspects, the FcγRIIIa is allotype 158V (F158V allelic variant). In other aspects, the FcγRIIIa is allotype 158F. In other aspects, the FcγRIII is isoform FcγRIIIb. In another aspect, the FcγRIIIb is allotype NA1. In other aspects, the FcγRIIIb is allotype NA2.

An IgG Fc variant domain containing polypeptide provided herein (e.g., an antibody or fragments thereof comprising a variant IgG Fc domain), can further comprise the substitution of at least one amino acid residue located in the Fc region, where such substitution results in increased affinity for FcRn. As described above, pH-dependent interaction of a wild type Fc domain with FcRn prolongs half-life. In one aspect, an IgG Fc variant domain containing polypeptide is provided which exhibits an increased affinity to FcRn relative to a parent polypeptide comprising a wild type Fc domain. In another aspect, an IgG Fc variant domain containing polypeptide is provided which exhibits an affinity for FcRn receptors that is at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold higher than a parent polypeptide comprising a wild type Fc domain. In another aspect, an IgG Fc variant domain containing polypeptide is provided which exhibits an affinity for FcRn receptors that is at least 90%, at least 80%, at least 70%, at least 60%, at least 50%, at least 40%, at least 30%, at least 20%, at least 10%, or at least 5% higher than a parent polypeptide comprising a wild type Fc domain. In particular aspects, an IgG Fc variant domain containing polypeptide is provided which exhibits a higher affinity for FcRn at pH 6.0 than at pH 7.4.

In one aspect, an IgG Fc variant domain containing polypeptide is provided which exhibits an affinity for FcγR receptors that is between about 100 nM to about 100 μM, or about 100 nM to about 10 μM, or about 100 nM to about 1 μM, or about 1 nM to about 100 μM, or about 10 nM to about 100 μM, or about 1 μM to about 100 μM, or about 10 μM to about 100 μM. In certain aspects, an IgG Fc variant domain containing polypeptide is provided which exhibits an affinity for FcγR receptors that is greater than 1 μM, greater than 5 μM, greater than 10 μM, greater than 25 μM, greater than 50 μM, or greater than 100 μM. In another aspect, an IgG Fc variant domain containing polypeptide is provided which exhibits an affinity for FcγR receptors that is less than 100 μM, less than 50 μM, less than 10 μM, less than 5 μM, less than 2.5 μM, less than 1 μM, or less than 100 nM, or less than 10 nM.

In specific aspects, a polypeptide comprising a FQQ, FQG or FAQ variant IgG Fc domain is provided which exhibits a decreased affinity to FcγR as compared to a parent polypeptide comprising a wild type IgG Fc domain. In other specific aspects, a polypeptide comprising a FQQ, FQG or FAQ variant IgG Fc domain further comprising substitutions at one or more positions selected from the group consisting of EU positions 252, 254, and 256 (e.g., Y, YT, YE, YTE mutations) is provided which exhibits a decreased affinity to FcγR as compared to a parent polypeptide comprising a wild type IgG Fc domain.

In specific aspects, a polypeptide comprising a FQQ, FQG or FAQ variant IgG Fc domain is provided which exhibits fully ablated binding to FcγR as compared to a parent polypeptide comprising a wild type IgG Fc domain. In other specific aspects, a polypeptide comprising a FQQ, FQG or FAQ variant IgG Fc domain further comprising substitutions at one or more positions selected from the group consisting of EU positions 252, 254, and 256 (e.g., Y, YT, YE, YTE mutations) is provided, which exhibits fully ablated binding to FcγR as compared to a parent polypeptide comprising a wild type IgG Fc domain.

In specific aspects, a polypeptide comprising a FQQ, FQG or FAQ variant IgG Fc domain is provided which exhibits an increased affinity to FcRn as compared to a parent polypeptide comprising a wild type Fc domain. In other specific aspects, a polypeptide comprising a FQQ, FQG or FAQ variant IgG Fc domain further comprising substitutions at one or more positions selected from the group consisting of EU positions 252, 254, and 256 (e.g., Y, YT, YE, YTE mutations) is provided, which exhibits an increased affinity to FcRn as compared to a parent polypeptide comprising a wild type Fc domain.

Binding to C1q

The complement activation pathway is initiated by the binding of the first component of the complement system (C1q) to a molecule, e.g., an IgG Fc variant domain containing polypeptide, complexed with a cognate antigen. To assess complement activation, a CDC assay, e.g., as described in Gazzano-Santoro et al., J. Immunol. Methods, 202:163 (1996), can be performed.

In one aspect, an IgG Fc variant domain containing polypeptide is provided which exhibits a decreased affinity to C1q relative to a parent polypeptide comprising a wild type IgG Fc domain. In another aspect, an IgG Fc variant domain containing polypeptide is provided which exhibits affinities for C1q receptor that are at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold less than a parent polypeptide comprising a wild type IgG Fc domain.

In another aspect, an IgG Fc variant domain containing polypeptide is provided which exhibits an affinity for C1q that is at least 90%, at least 80%, at least 70%, at least 60%, at least 50%, at least 40%, at least 30%, at least 20%, at least 10%, or at least 5% less than a parent polypeptide comprising a wild type IgG Fc domain.

In another aspect, an IgG Fc variant domain containing polypeptide is provided which exhibits an affinity for C1q that is between about 100 nM to about 100 μM, or about 100 nM to about 10 μM, or about 100 nM to about 1 μM, or about 1 nM to about 100 μM, or about 10 nM to about 100 μM, or about 1 μM to about 100 μM, or about 10 μM to about 100 μM. In certain aspects, an IgG Fc variant domain containing polypeptide is provided which exhibits an affinity for C1q that is greater than 1 μM, greater than 5 μM, greater than 10 μM, greater than 25 μM, greater than 50 μM, or greater than 100 μM.

In specific aspects, a polypeptide comprising a FQQ, FQG or FAQ variant IgG Fc domain is provided, which exhibits a decreased affinity to C1q as compared to a parent polypeptide comprising a wild type IgG Fc domain. In other specific aspects, a polypeptide comprising a FQQ, FQG or FAQ variant IgG Fc domain further comprising substitutions at one or more positions selected from the group consisting of EU positions 252, 254, and 256 (e.g., Y, YT, YE, YTE mutations) is provided, which, exhibits a decreased affinity to C1q as compared to a parent polypeptide comprising a wild type IgG Fc domain.

In specific aspects, a polypeptide comprising a FQQ, FQG or FAQ variant IgG Fc domain is provided which exhibits fully ablated binding to C1q as compared to a parent polypeptide comprising a wild type IgG Fc domain. In other specific aspects, a polypeptide comprising a FQQ, FQG or FAQ variant IgG Fc domain further comprising substitutions at one or more positions selected from the group consisting of EU positions 252, 254, and 256 (e.g., Y, YT, YE, YTE mutations) is provided, which exhibits fully ablated binding to C1q as compared to a parent polypeptide comprising a wild type IgG Fc domain.

Reduced ADCC Activity

In one aspect, an IgG Fc variant domain containing polypeptide is provided which exhibits a decreased ADCC activity as compared to a parent polypeptide comprising a wild type IgG Fc domain. In another aspect, an IgG Fc variant domain containing polypeptide is provided which exhibits an ADCC activity that is at least 2 fold, or at least 3 fold, or at least 5 fold or at least 10 fold or at least 50 fold or at least 100 fold less than that of a parent polypeptide comprising a wild type IgG Fc domain, or has no detectable ADCC activity at a concentration of 300 μg/ml. In still another aspect, an IgG Fc variant domain containing polypeptide is provided which exhibits an ADCC activity that is reduced by at least 10%, or at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% relative to a parent polypeptide comprising a wild type IgG Fc domain. In certain aspects, an IgG Fc variant domain containing polypeptide is provided which has no detectable ADCC activity.

In specific aspects, the reduction or ablation of ADCC activity can be attributed to the reduced affinity that an IgG Fc variant domain containing polypeptide provided herein exhibits for Fc ligands and/or receptors.

In specific aspects, a polypeptide comprising a FQQ, FQG or FAQ variant IgG Fc domain is provided which exhibits reduction or ablation of ADCC activity as compared to a parent polypeptide comprising a wild type IgG Fc domain. In other specific aspects, a polypeptide comprising a FQQ, FQG or FAQ variant IgG Fc domain further comprising substitutions at one or more positions selected from the group consisting of EU positions 252, 254, and 256 (e.g., Y, YT, YE, YTE mutations) is provided, which exhibits reduction or ablation of ADCC activity as compared to a parent polypeptide comprising a wild type IgG Fc domain.

It is contemplated that an IgG variant domain containing polypeptide provided herein can be characterized by in vitro functional assays for determining one or more FcγR mediated effector cell functions. In certain aspects, an IgG Fc variant domain containing polypeptide is provided which has similar binding properties and effector cell functions in in vivo models as those in in vitro based assays. However, the present disclosure does not exclude an IgG Fc variant domain containing polypeptide that does not exhibit the desired phenotype in in vitro based assays but do exhibit the desired phenotype in vivo.

Reduced CDC Activity

In one aspect, an IgG Fc variant domain containing polypeptide is provided which exhibits decreased CDC activity as compared to a parent polypeptide comprising a wild type IgG Fc domain. In another aspect, an IgG Fc variant domain containing polypeptide is provided which exhibits CDC activity that is at least 2 fold, or at least 3 fold, or at least 5 fold or at least 10 fold or at least 50 fold or at least 100 fold less than that of a parent polypeptide comprising a wild type IgG Fc domain. In still another aspect, an IgG Fc variant domain containing polypeptide is provided which exhibits CDC activity that is reduced by at least 10%, or at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% relative to a parent polypeptide comprising a wild type IgG Fc domain, or has no detectable CDC activity at a concentration of 300 µg/ml. In certain aspects, an IgG Fc variant domain containing polypeptide is provided which exhibits no detectable CDC activity. In specific aspects, the reduction and/or ablation of CDC activity can be attributed to the reduced affinity that an IgG Fc variant domain containing polypeptide exhibits for Fc ligands and/or receptors.

In specific aspects, a polypeptide comprising a FQQ, FQG or FAQ variant IgG Fc domain is provided which, exhibits decreased or fully ablated CDC activity as compared to a parent polypeptide comprising a wild type IgG Fc domain. In other specific aspects, a polypeptide comprising a FQQ, FQG or FAQ variant IgG Fc domain further comprising substitutions at one or more positions selected from the group consisting of EU positions 252, 254, and 256 (e.g., Y, YT, YE, YTE mutations) is provided, which exhibits decreased or fully ablated CDC activity as compared to a parent polypeptide comprising a wild type IgG Fc domain.

Reduced Toxicity

While effector functions (.e.g., ADCC and CDC) can be an important mechanism contributing to the clinical efficacy it is understood in the art that biological therapies can have adverse toxicity issues associated with the complex nature of directing the immune system to recognize and attack unwanted cells and/or targets. Furthermore, when the recognition and/or the targeting for attack do not take place where the treatment is required, consequences such as adverse toxicity can occur. Thus, depending on the desired mechanism of action, effector functions of a given therapeutic molecule can be modulated to reduce related toxicities.

In one aspect, an IgG Fc variant domain containing polypeptide is provided which exhibits reduced toxicity as compared to a parent polypeptide comprising a wild type IgG Fc domain. In another aspect, an IgG Fc variant domain containing polypeptide is provided which exhibits a toxicity that is at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold less than that of a parent polypeptide comprising a wild type IgG Fc domain. In another aspect, an IgG Fc variant domain containing polypeptide is provided which exhibits a toxicity that are reduced by at least 10%, or at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% relative to a parent polypeptide comprising a wild type IgG Fc domain.

In specific aspects, a polypeptide comprising a FQQ, FQG or FAQ variant IgG Fc domain is provided, which exhibits reduced toxicity as compared to a parent polypeptide comprising a wild type IgG Fc domain. In other specific aspects, a polypeptide comprising a FQQ, FQG or FAQ variant IgG Fc domain further comprising substitutions at one or more positions selected from the group consisting of EU positions 252, 254, and 256 (e.g., Y, YT, YE, YTE mutations) is provided, which exhibits reduced toxicity as compared to a parent polypeptide comprising a wild type IgG Fc domain.

Increased Stability

In another aspect, an IgG Fc variant domain containing polypeptide is provided which possesses increased stability, e.g., thermal stability, when compared to the same polypeptide comprising a FES-YTE variant IgG Fc domain. In some aspects, a polypeptide comprising a FQQ, FQG or FAQ variant IgG Fc domain further comprising substitutions at one or more positions selected from the group consisting of EU positions 252, 254, and 256 (e.g., Y, YT, YE, YTE mutations) is provided, which possesses increased stability, e.g., thermal stability, when compared to the same polypeptides comprising a FES-YTE variant IgG Fc domain. In specific aspects, a polypeptide comprising a FQQ, FQG or FAQ variant IgG Fc domain further comprising YTE mutations is provided, which possesses increased stability, e.g., thermal stability, when compared to the same polypeptides comprising a FES-YTE variant IgG Fc domain.

As used herein, the term "stability" refers to an art-recognized measure of the maintenance of one or more physical properties of a polypeptide in response to an environmental condition (e.g., an elevated or lowered temperature). In certain aspects, the physical property can be the maintenance of the covalent structure of the polypeptide (e.g., the absence of proteolytic cleavage, unwanted oxidation or deamidation). In other aspects, the physical property can also be the presence of the polypeptide in a properly folded state (e.g., the absence of soluble or insoluble aggregates or precipitates). In one aspect, the stability of the polypeptide is measured by assaying a biophysical property of the polypeptide, for example thermal stability, pH unfolding profile, stable removal of glycosylation, solubility, biochemical function (e.g., ability to bind to another protein), % fragmentation, purity loss, etc., and/or combinations thereof. In another aspect, biochemical function is demonstrated by the binding affinity of the interaction.

In one aspect, a measure of protein stability is thermal stability, i.e., resistance to thermal challenge. Stability can be measured using methods known in the art, such as, HPLC (high performance liquid chromatography), SEC (size exclusion chromatography), DLS (dynamic light scattering), etc. Methods to measure thermal stability include, but are not limited to differential scanning calorimetry (DSC), differential scanning fluorimetry (DSF), circular dichroism (CD), and thermal challenge assay.

In some aspects, an IgG Fc variant domain containing polypeptide is provided which exhibits increased thermal stability when compared to the same polypeptides comprising a FES-YTE variant IgG Fc domain, as measured by DSC. In some aspects, an IgG Fc variant domain containing polypeptide is provided which exhibits an increase in thermal stability as measured by DSC of at least 1° C., at least 2° C., at least 3° C., at least 4° C., at least 5° C., at least 6° C., at least 7° C., at least 8° C., at least 9° C. or at least 10° C. when compared to the same polypeptide comprising a FES-YTE variant IgG Fc domain. In other aspects, an IgG Fc variant domain containing polypeptide is provided which exhibits an increase in thermal stability as measured by DSC of about 1° C., about 2° C., about 3° C., about 4° C., about 5° C., about 6° C., about 7° C., about 8° C., about 9° C. or about 10° C. when compared to the same polypeptide comprising a FES-YTE variant IgG Fc domain.

In some aspects, a polypeptide comprising a FQQ, FQG or FAQ variant IgG Fc domain further comprising substitutions at one or more positions selected from the group consisting of EU positions 252, 254, and 256 (e.g., Y, YT, YE, YTE mutations) is provided, which exhibits an increase in thermal stability as measured by DSC when compared to the same polypeptides comprising a FES-YTE variant IgG Fc domain. In specific aspects, a polypeptide comprising a FQQ, FQG or FAQ variant IgG Fc domain further comprising YTE mutations is provided, which exhibits an increase in thermal stability as measured by DSC when compared to a parent polypeptide comprising a FES-YTE variant IgG Fc domain.

In some aspects, an IgG Fc variant domain containing polypeptide is provided which exhibits increased thermal stability when compared to the same polypeptide comprising a FES-YTE variant IgG Fc domain, as measured by DSF. In some aspects, thermal stability is measured using DSF and the SYPRO® Orange DSF fluorescent probe. One of skill in the art would understand that fluorescent probes other than SYPRO® Orange, such as Nile Red, SYPRO® Red, dapoxyl sulfonic acid, bis-anilinonaphtalene sulfonic acid (bis-ANS), 1-anilinonaphtalene-8-sulfonic acid (1,8-ANS), or CPM among others, can be used to measure protein stability by DSF (see, e.g., Niesen et al., Nature Protocols 2:2212-21 (2007)).

In some aspects, an IgG Fc variant domain containing polypeptide is provided which exhibits an increase in thermal stability as measured by DSF using SYPRO® Orange of at least 1° C., at least 2° C., at least 3° C., at least 4° C., at least 5° C., at least 6° C., at least 7° C., at least 8° C., at least 9° C. or at least 10° C. when compared to the same polypeptide comprising a FES-YTE variant IgG Fc domain.

In other aspects, an IgG Fc variant domain containing polypeptide is provided which exhibits an increase in thermal stability as measured by DSF using SYPRO® Orange of about 1° C., about 2° C., about 3° C., about 4° C., about 5° C., about 6° C., about 7° C., about 8° C., about 9° C. or about 10° C. when compared to the same polypeptide comprising a FES-YTE variant IgG Fc domain.

In some aspects, a polypeptide comprising a FQQ, FQG or FAQ variant IgG Fc domain further comprising substitutions at one or more positions selected from the group consisting of EU positions 252, 254, and 256 (e.g., Y, YT, YE, YTE mutations) is provided, which exhibits an increase in thermal stability as measured by DSF using SYPRO® Orange when compared to the same polypeptides comprising a FES-YTE variant IgG Fc domain. In specific aspects, a polypeptide comprising a FQQ, FQG or FAQ variant IgG Fc domain further comprising YTE mutations is provided, which exhibits an increase in thermal stability as measured by DSF using SYPRO® Orange when compared to a parent polypeptide comprising a FES-YTE variant IgG Fc domain.

In some aspects, an IgG Fc variant domain containing polypeptide is provided which exhibits increased apparent solubility when compared to the same polypeptides comprising a FES-YTE IgG Fc domain, as measured by using a polyethylene glycol (PEG) precipitation assay. See, e.g., Middaugh et al., J. Biol. Chem. 254:367-370 (1979); Shire et al., eds., 2010, Current Trends in Monoclonal Antibody Development and Manufacturing, Springer; Gibson et al., J. Pharm. Sci. 100:1009-21 (2011). In some aspects, a polypeptide comprising a FQQ, FQG or FAQ variant IgG Fc domain further comprising substitutions at one or more positions selected from the group consisting of EU positions 252, 254, and 256 (e.g., Y, YT, YE, YTE mutations) is provided, which exhibits increased apparent solubility as measured by using a polyethylene glycol (PEG) precipitation assay when compared to the same polypeptides comprising a FES-YTE variant IgG Fc domain. In specific aspects, a polypeptide comprising a FQQ, FQG or FAQ variant IgG Fc domain further comprising YTE mutations is provided, which exhibits increased apparent solubility as measured by using a polyethylene glycol (PEG) precipitation assay when compared to a parent polypeptide comprising a FES-YTE variant IgG Fc domain.

Biopharmaceutical products in storage change as they age, but they are considered to be stable as long as their characteristics remain within the manufacturer's specifications. The number of days that the product remains stable at the recommended storage conditions is referred to as the shelf life. The experimental protocols commonly used for data collection that serve as the basis to estimate a product shelf life are referrer to as stability assays. Shelf life is generally estimated according to types of stability testing: real-time stability assays and accelerated stability assays. In accelerated stability assays, a product is stored at elevated stress conditions, e.g., temperature, humidity, and pH. See, e.g., Tydeman & Kirkwood, J. Biol. Stand. 12:195-206 (1984); Some et al., J. Pharm. Sci. 90:1759-66 (2001); FDA. Guidelines for submitting documentations for the stability of human drugs and biologics. Rockville (MD), 1987.

In some aspects, an IgG Fc variant domain containing polypeptide is provided which exhibits an increase in stability as measured using an accelerated stability assay when compared to the same polypeptide comprising a FES-YTE variant IgG Fc domain. In some aspects, a polypeptide comprising a FQQ, FQG or FAQ variant IgG Fc domain further comprising substitutions at one or more positions selected from the group consisting of EU positions 252, 254, and 256 (e.g., Y, YT, YE, YTE mutations) is provided, which exhibits an increase in stability as measured using an accelerated stability assay when compared to the same polypeptides comprising a FES-YTE variant IgG Fc domain. In specific aspects, a polypeptide comprising a FQQ, FQG or FAQ variant IgG Fc domain further comprising YTE mutations is presented, which exhibits an increase in stability as measured using an accelerated stability assay when compared to the same polypeptide comprising a FES-YTE variant IgG Fc domain.

In some aspects, the accelerated stability assay comprises incubation of an IgG Fc variant domain containing polypeptide for an extended period of time and/or incubation at high temperature. In other aspects, the accelerated stability assay is performed by incubation of an IgG Fc variant domain containing polypeptide at a high concentration. In some aspects, the measurements in the accelerated stability assay are performed using High Performance Size Exclusion Chromatography (HPSEC). In other aspects, the measurements in the accelerated stability assay are performed using Dynamic Light Scattering (DSL). A person of ordinary skill in the art would appreciate that polypeptide aggregation can be measured by a variety of methods known in the art.

In some aspects, the extended period of time in the accelerated stability assay is at least one week, at least two weeks, at least three weeks, at least four weeks, at least one month, at least two months, at least three months, or at least four months. In other aspects, the extended period of time in the accelerated stability assay is about one week, about two weeks, about three weeks, about four weeks, about one month, about two months, about three months, or about four months.

In some aspects, the concentration of IgG Fc variant domain containing polypeptide used in the accelerated stability assay is at least 10 mg/ml, at least 15 mg/ml, at least 20 mg/ml, at least 25 mg/ml, at least 30 mg/ml, at least 35 mg/ml, at least 40 mg/ml, at least 45 mg/ml, or at least 50 mg/ml. In some aspects, the concentration of IgG Fc variant domain containing polypeptide used in the accelerated stability assay is about 10 mg/ml, about 15 mg/ml, about 20 mg/ml, about 25 mg/ml, about 30 mg/ml, about 35 mg/ml, about 40 mg/ml, about 45 mg/ml, or about 50 mg/ml.

In some aspects, the temperature used in the accelerated stability assay is at least 30° C., at least 35° C., at least 40° C., at least 45° C., at least 50° C., at least 55° C., or at least 60° C. In some aspects, the high temperature used in the accelerated stability assay is about 30° C., about 35° C., about 40° C., about 45° C., about 50° C., about 55° C., or about 60° C.

Methods

In some aspects, a method to diminish Fc-induced effector function (e.g., ADCC and/or CDC) in an IgG Fc variant domain containing polypeptide is presented, which comprises (a) substituting the amino acid at EU position 234 in the Fc domain with phenylalanine (F); (b) substituting the amino acid at EU position 235 in the Fc domain with alanine (A), asparagine (N), phenylalanine (F), glutamine (Q), or valine (V); and, (c) substituting the amino acid at EU position 322 of the Fc domain with alanine (A), aspartic acid (D), glutamic acid (E), histidine (H), asparagine (N), or glutamine (Q); or substituting the amino acid at EU position 331 of the Fc domain with alanine (A) or glycine (G). In some aspects, the Fc domain of the parent polypeptide comprises a tyrosine (Y) at EU position 252; and/or a threonine (T) at EU position 254; and/or, a glutamic acid (E) at position EU 256. In some specific aspects, the Fc domain of the parent polypeptide comprises a tyrosine (Y) at EU position 252, a threonine (T) at EU position 254, and a glutamic acid (E) at EU position 256, i.e., the Fc domain of the parent polypeptide is a YTE variant IgG Fc domain.

In some aspects, a method to diminish Fc-induced effector function (e.g., ADCC and/or CDC) and increase the half-life of a parent polypeptide comprising an IgG Fc domain is presented, which comprises (a) substituting the amino acid at EU position 234 in the Fc domain with phenylalanine (F); (b) substituting the amino acid at EU position 235 in the Fc domain with alanine (A), asparagine (N), phenylalanine (F), glutamine (Q), or valine (V); and, (c) substituting the amino acid at EU position 322 of the Fc domain with alanine (A), aspartic acid (D), glutamic acid (E), histidine (H), asparagine (N), or glutamine (Q); or substituting the amino acid at EU position 331 of the Fc domain with alanine (A) or glycine (G); and (d) substituting the amino acid at EU position 252 with tyrosine (Y). In some aspects, the method further comprises substituting the amino acid at EU position 254 with threonine (T); and, substituting the amino acid at EU position 256 with glutamic acid (E).

In some aspects, the method to diminish Fc-induced effector function (e.g., ADCC and/or CDC) and the method to diminish Fc-induced effector function (e.g., ADCC and/or CDC) and increase the half-life described above comprise the substitution of the amino acid at EU position 234 in the Fc domain with phenylalanine (F); the substitution of the amino acid at EU position 235 in the Fc domain with glutamine (Q); and the substitution of the amino acid at EU position 322 in the Fc domain with glutamine (Q).

In some aspects, the method to diminish Fc-induced effector function (e.g., ADCC and/or CDC) and the method to diminish Fc-induced effector function (e.g., ADCC and/or CDC) and increase the half-life described above comprise the substitution of the amino acid at EU position 234 of the Fc domain with phenylalanine (F); the substitution of the amino acid at EU position 235 of the Fc domain with glutamine (Q); and the substitution of the amino acid at EU position 331 of the Fc domain with glycine (G).

In some aspects, the method to diminish Fc-induced effector function (e.g., ADCC and/or CDC) and the method to diminish Fc-induced effector function (e.g., ADCC and/or CDC) and increase the half-life described above comprise the substitution of the amino acid at EU position 234 of the Fc domain with phenylalanine (F); the substitution of the amino acid at EU position 235 of the Fc domain with alanine (A); and the substitution of the amino acid at EU position 322 of the Fc domain with glutamine (Q).

Antibodies and Fragments Thereof

In some aspects, an IgG Fc variant domain containing polypeptide comprises an antigen binding domain. In some specific aspects, the antigen-binding domain can be an antibody, e.g., a monoclonal antibody, or an antigen-binding fragment thereof. The antigen-binding domain can be a full length antibody, e.g., a human antibody, a humanized antibody, or a chimeric antibody, or a fragment thereof. In some aspects, the antigen-binding domain comprises, e.g., a single chain antibody; a diabody; a polypeptide chain of an antibody; an F(ab')2 fragment; or, and F(ab) fragment.

The term "antibody variant" refers to a polypeptide containing a variant IgG Fc domain provided herein, wherein the polypeptide is an antibody. Antibody variants include monoclonal antibodies, multispecific antibodies, human antibodies, humanized antibodies, camelized antibodies, chimeric antibodies, anti-idiotypic (anti-Id) antibodies, and Fc domain-containing fragments of any of the above. In some aspects, antibody variants include immunoglobulin molecules and immunologically active fragments of immunoglobulin molecules, i.e., molecules that contain an antigen binding site, wherein these fragments can be fused or conjugated to another immunoglobulin domain comprising a variant IgG Fc domain provided herein. In one aspect, the antibody variants are of the human IgG1, IgG2, IgG3 or IgG4 isotype.

Antibody variants and fragments thereof comprising a variant IgG Fc domain provided herein can be from any animal origin including birds and mammals (e.g., human, a rodent such as mouse or rat, donkey, sheep, rabbit, goat, guinea pig, camel, horse, or chicken). In a specific aspect, an antibody variant is provided which is a human or a humanized monoclonal antibody. As used herein, "human" antibodies include antibodies having the amino acid sequence of a human immunoglobulin and also include antibodies isolated from human immunoglobulin libraries or from mice that express antibodies from human genes.

An antibody variant can be monospecific, bispecific, trispecific or have greater specificity (multispecific antibodies). Multispecific antibody variants can specifically bind to different epitopes of desired target molecule or can specifically bind to both the target molecule as well as a heterologous epitope, such as a heterologous polypeptide or solid support material. See, e.g., International Publication Nos. WO 94/04690; WO 93/17715; WO 92/08802; WO 91/00360; and WO 92/05793; Tutt et al., J. Immunol. 147:60-69 (1991); U.S. Pat. Nos. 4,474,893, 4,714,681, 4,925,648, 5,573,920, and 5,601,819; and Kostelny et al., J. Immunol. 148:1547 (1992)). Methods for making bispecific or multispecific antibodies are known in the art.

Methods of Producing Antibodies Comprising Variant IgG Fc Domains

Antibody variants or fragments thereof can be produced by any method known in the art for the synthesis of antibodies, in particular, by chemical synthesis or by recombinant expression techniques.

Monoclonal antibody variants can be prepared using a wide variety of techniques known in the art including the use of hybridoma, recombinant, and phage display technologies, or a combination thereof. For example, monoclonal antibody variants can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981). Methods for producing and screening for specific antibodies using hybridoma technology are routine and known in the art.

Antibody variants can be generated by numerous methods well known to one skilled in the art. Non-limiting examples include, isolating antibody coding regions (e.g., from hybridomas) and introducing one or more Fc domain amino acid substitutions into the isolated antibody coding region. Alternatively, the variable regions can be subcloned into a vector encoding a variant IgG Fc domain provided herein.

Antibody variant fragments which recognize specific epitopes can be generated by any technique known to those of skill in the art. For some uses, including in vivo use of antibody variants in humans and in vitro detection assays, it can be advantageous to use human or chimeric antibody variants. Completely human antibodies are particularly desirable for therapeutic treatment of human subjects. Human antibodies or fragments thereof comprising a variant IgG Fc domain provided herein can be made by a variety of methods known in the art. See, e.g., U.S. Pat. Nos. 4,444,887 and 4,716,111; and International Publication Nos. WO 98/46645, WO 98/50433, WO 98/24893, WO98/16654, WO 96/34096, WO 96/33735, and WO 91/10741.

A chimeric antibody variant or fragment thereof comprising a variant IgG Fc domain provided herein can also be made by a variety of methods known in the art. See, e.g., Morrison, Science 229:1202 (1985); Oi et al., BioTechniques 4:214 (1986); Gillies et al., J. Immunol. Methods 125:191-202(1989); and U.S. Pat. Nos. 5,807,715, 4,816, 567, 4,816,397, and 6,311,415. In certain instances, a humanized antibody variant or fragment thereof can comprise a variant IgG Fc domain provided herein. Humanized antibody variants can be produced using variety of techniques known in the art, including but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, Molecular Immunology 28:489-498 (1991); Studnicka et al., Protein Engineering 7:805-814 (1994); and Roguska et al., Proc. Natl. Acad. Sci. USA 91:969-973 (1994)), chain shuffling (U.S. Pat. No. 5,565,332), and techniques disclosed in, e.g., U.S. Pat. Nos. 6,407,213 and 5,766,886, International Publication No. WO 9317105, Tan et al., J. Immunol. 169:1119-25 (2002), Caldas et al., Protein Eng. 13:353-60 (2000), Morea et al., Methods 20:267-79 (2000), Baca et al., J. Biol. Chem. 272:10678-84 (1997), Roguska et al., Protein Eng. 9:895-904 (1996), Couto et al., Cancer Res. 55(23 Supp):5973s-5977s (1995), Couto et al., Cancer Res. 55:1717-22 (1995), Sandhu, Gene 150:409-10 (1994), and Pedersen et al., J. Mol. Biol. 235:959-73 (1994).

Human antibody variants can also be produced using transgenic mice which are incapable of expressing functional endogenous immunoglobulins, but which can express human immunoglobulin genes. For example, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen or immunogenic fragments thereof.

Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful antibodies. For an overview of this technology for producing human antibodies, see Lonberg and Huszar, Int. Res. Immunol. 13:65-93 (1995). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661, 016, 5,545,806, 5,814,318, and 5,939,598.

Polynucleotides

A polynucleotide is provided which encodes an IgG Fc variant domain containing polypeptide. Also provided is a polynucleotide that hybridizes under high stringency, intermediate, or lower stringency hybridization conditions to a polynucleotide that encodes an IgG Fc variant domain containing polypeptide.

In some aspects, a polynucleotide sequence encoding an IgG Fc variant domain containing polypeptide can be produced from a parent polynucleotide sequence obtained from a suitable source. Once the polynucleotide sequence has been obtained, the polynucleotide sequence can be manipulated using methods known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate an IgG Fc variant domain containing polypeptide having a different amino acid sequence, for example to create amino acid substitutions, deletions, and/or insertions.

In other aspects, a polynucleotide sequence encoding an IgG Fc variant domain containing polypeptide can be assembled from chemically synthesized oligonucleotides (e.g., as described in Kutmejer et al. BioTechniques 17:242 (1994)), which, briefly, involves the synthesis of overlapping oligonucleotides containing portions of the encoding sequence, annealing and ligating of those oligonucleotides, and then amplification of the ligated oligonucleotides by PCR.

Specific Antigens and Fusion Partners

Virtually any molecule can be targeted by a binding-molecule, e.g., an antibody, fusion protein, or conjugate comprising a variant IgG Fc domain. In additional, virtually any molecule can be incorporated into a fusion protein or a conjugate comprising a variant IgG Fc domain provided herein.

These specific targeted molecules and/or fusion partners include, but are not limited to, the following list of proteins, as well as subunits, domains, motifs and epitopes belonging to the following list of proteins: renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VII, factor VIIIC, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors such as, for example, EGFR, VEGFR; interferons such as alpha interferon (α-IFN), beta interferon (β-IFN) and gamma interferon (γ-IFN); protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor; platelet-derived growth factor (PDGF); fibroblast growth factor such as AFGF and PFGF; epidermal growth factor (EGF); transforming growth factor (TGF) such as TGF-alpha and TGF-beta, including TGF-1, TGF-2, TGF-3, TGF-4, or TGF-5; insulin-like growth factor-I and -II (IGF-I and IGF-II); des (1-3)-IGF-I (brain IGF-I), insulin-like growth factor binding proteins; CD proteins such as CD2, CD3, CD4, CD 8, CD11a, CD14, CD18, CD19, CD20, CD22, CD23, CD25, CD33, CD34, CD40, CD40L, CD52, CD63, CD64, CD80 and CD147; erythropoietin; osteoinductive factors; immunotoxins; a bone morphogenetic protein (BMP); an interferon such as interferon-alpha, -beta, and -gamma; colony stimulating factors (CSFs), such as M-CSF, GM-CSF, and G-CSF; interleukins (ILs), e.g., IL-1 to IL-13; TNFα, superoxide dismutase; T-cell receptors; surface membrane proteins; decay accelerating factor; viral antigen such as, for example, a portion of the AIDS envelope, e.g., gp120; transport proteins; homing receptors; addressins; regulatory proteins; cell adhesion molecules such as LFA-1, Mac 1, p150.95, VLA-4, ICAM-1, ICAM-3 and VCAM, a4/p7 integrin, and (Xv/p3 integrin including either a or subunits thereof, integrin alpha subunits such as CD49a, CD49b, CD49c, CD49d, CD49e, CD49f, alpha7, alpha8, alpha9, alphaD, CD11a, CD11b, CD51, CD11c, CD41, alphaIIb, alphaIELb; integrin beta subunits such as, CD29, CD 18, CD61, CD104, beta5, beta6, beta7 and beta8; Integrin subunit combinations including but not limited to, αVβ3, αVβ5 and α4β7; a member of an apoptosis pathway; IgE; blood group antigens; flk2/flt3 receptor; obesity (OB) receptor; mp1 receptor; CTLA-4; protein C; an Eph receptor such as EphA2, EphA4, EphB2, etc.; a Human Leukocyte Antigen (HLA) such as HLA-DR; complement proteins such as complement receptor CR1, C1Rq and other complement factors such as C3, and C5; a glycoprotein receptor such as GpIbα, GPIIb/IIIa and CD200; and fragments of any of the above-listed polypeptides.

In some aspects, an IgG Fc variant domain containing polypeptide (e.g., an antibody variant, fusion protein, or conjugate) can specifically bind cancer antigens including, but not limited to, ALK receptor (pleiotrophin receptor), pleiotrophin, KS 1/4 pan-carcinoma antigen; ovarian carcinoma antigen (CA125); prostatic acid phosphate; prostate specific antigen (PSA); melanoma-associated antigen p97; melanoma antigen gp75; high molecular weight melanoma antigen (HMW-MAA); prostate specific membrane antigen; carcinoembryonic antigen (CEA); polymorphic epithelial mucin antigen; human milk fat globule antigen; colorectal tumor-associated antigens such as: CEA, TAG-72, CO17-1A, GICA 19-9, CTA-1 and LEA; Burkitt's lymphoma antigen-38.13; CD19; human B-lymphoma antigen-CD20; CD33; melanoma specific antigens such as ganglioside GD2, ganglioside GD3, ganglioside GM2 and ganglioside GM3; tumor-specific transplantation type cell-surface antigen (TSTA); virally-induced tumor antigens including T-antigen, DNA tumor viruses and Envelope antigens of RNA tumor viruses; oncofetal antigen-alpha-fetoprotein such as CEA of colon, 5T4 oncofetal trophoblast glycoprotein and bladder tumor oncofetal antigen; differentiation antigen such as human lung carcinoma antigens L6 and L20; antigens of fibrosarcoma; human leukemia T cell antigen-Gp37; neoglycoprotein; sphingolipids; breast cancer antigens such as EGFR (Epidermal growth factor receptor); NY-BR-16; NY-BR-16 and HER2 antigen (p185HER2); polymorphic epithelial mucin (PEM); malignant human lymphocyte antigen-APO-1; differentiation antigen such as I antigen found in fetal erythrocytes; primary endoderm I antigen found in adult erythrocytes; preimplantation embryos; I(Ma) found in gastric adenocarcinomas; M18, M39 found in breast epithelium; SSEA-1 found in myeloid cells; VEP8; VEP9; Myl; Va4-D5; D156-22 found in colorectal cancer; TRA-1-85 (blood group H); SCP-1 found in testis and ovarian cancer; C14 found in colonic adenocarcinoma; F3 found in lung adenocarcinoma; AH6 found in gastric cancer; Y hapten; Ley found in embryonal carcinoma cells; TL5 (blood group A); EGF receptor found in A431 cells; E1 series (blood group B) found in pancreatic cancer; FC10.2 found in embryonal carcinoma cells; gastric adenocarcinoma antigen; CO-514 (blood group Lea) found in Adenocarcinoma; NS-10 found in adenocarcinomas; CO-43 (blood group Leb); G49 found in EGF receptor of A431 cells; MH2 (blood group ALeb/Ley) found in colonic adenocarcinoma; 19.9 found in colon cancer; gastric cancer mucins; T5A7 found in myeloid cells; R24 found in melanoma; 4.2, GD3, D1.1, OFA-1, GM2, OFA-2, GD2, and M1:22:25:8 found in embryonal carcinoma cells and SSEA-3 and SSEA-4 found in 4 to 8-cell stage embryos; Cutaneous Tcell Lymphoma antigen; MART-1 antigen; Sialy Tn (STn) antigen; Colon cancer antigen NY-CO-45; Lung cancer antigen NY-LU-12 valiant A; Adenocarcinoma antigen ART1; Paraneoplastic associated brain-testis-cancer antigen (onconeuronal antigen MA2; paraneoplastic neuronal antigen); Neuro-oncological ventral antigen 2 (NOVA2); Hepatocellular carcinoma antigen gene 520; Tumor-Associated Antigen CO-029; Tumor-associated antigens MAGE-C1 (cancer/testis antigen CT7), MAGE-B1 (MAGE-XP antigen), MAGE-B2 (DAM6), MAGE-2, MAGE-4-a, MAGE-4-b and MAGE-X2; Cancer-Testis Antigen (NY-EOS-1) and fragments of any of the above-listed polypeptides.

In further aspects, an IgG Fc variant domain containing polypeptide (e.g., an antibody variant, fusion protein, or conjugate) can specifically bind infectious agent (e.g., bacteria, virus). Infectious bacteria include, but are not limited to, gram negative and gram positive bacteria. Gram positive bacteria include, but are not limited to Pasteurella species, Staphylococci species, and Streptococcus species. Gram negative bacteria include, but are not limited to, Escherichia coli, Pseudomonas species, and Salmonella species. Specific examples of infectious bacteria include but are not limited to: Helicobacter pylori, Borrelia burgdorferi, Legionella pneumophila, Mycobacteria species (e.g., M. tuberculosis, M. avium, M. intracellulare, M. kansasii, M. gordonae), Staphylococcus aureus, Pseudomonas aeruginosa, Neisseria gonorrhoeae, Neisseria meningitidis, Listeria monocytogenes, Streptococcus pyogenes (Group A Streptococcus), Streptococcus agalactiae (Group B Streptococcus), Streptococcus (viridans group), Streptococcus faecalis, Streptococcus bovis, Streptococcus (anaerobic species), Streptococcus pneumoniae, pathogenic Campylobacter sp., Enterococcus sp., Haemophilus influenzae, Bacillus anthracis, Corynebacterium diphtheriae, Corynebacterium sp., Erysipelothrix rhusiopathiae, Clostridium perfringens, Clostridium tetani, Enterobacter aerogenes, Klebsiella pneumoniae, Pasteurella multocida, Bacteroides sp., Fusobacterium nucleatum, Streptobacillus moniliformis, Treponema pallidum, Treponema pertenue, Leptospira, Rickettsia, and Actinomyces israelii. Viruses include, but are not limited to, enteroviruses, rotaviruses, adenovirus, hepatitis virus. Specific examples of viruses that have been found in humans include but are not limited to: Retroviridae (e.g., human immunodeficiency viruses (HIV); Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arenaviridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papillomaviruses, polyoma viruses); Adenoviridae (most adenoviruses); Herpesviridae (herpes simplex virus (HSV) 1 and 2, varicella zoster virus, cytomegalovirus (CMV)); Poxviridae (variola viruses, vaccinia viruses, pox viruses); Iridoviridae (e.g., African swine fever virus); and unclassified viruses (e.g., the etiological agents of spongiform encephalopathies, the agent of delta hepatitis, the agents of non-A, non-B hepatitis; Norwalk and related viruses, and astroviruses).

Conjugates and Derivatives

In some aspects, a variant IgG Fc domain provided herein can be conjugated or fused to one or more moieties, including but not limited to, peptides, polypeptides, proteins, fusion proteins, nucleic acid molecules, small molecules, mimetic agents, synthetic drugs, inorganic molecules, and organic molecules.

In some aspects, an IgG Fc variant domain containing polypeptide includes derivatives that are modified, e.g., by covalent attachment of any type of molecule to the polypeptide or chemical or enzymatic modification. For example, derivatives include polypeptides that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to, specific chemical cleavage, acetylation, formylation, etc. Additionally, the derivative can contain one or more non-classical amino acids.

An IgG Fc variant domain containing polypeptide can be attached to a polymer molecule such as high molecular weight polyethyleneglycol (PEG). PEG can be attached to a polypeptide with or without a multifunctional linker either through site-specific conjugation of the PEG to the N- or C-terminus of the polypeptide or via epsilon-amino groups present on lysine residues. Linear or branched polymer derivatization that results in minimal loss of biological activity can be used.

Conjugates are provided which comprise an IgG Fc variant domain containing polypeptide chemically conjugated (including both covalent and non-covalent conjugations) to a heterologous protein or polypeptide (or fragment thereof, to a polypeptide of at least 10, at least 20, at least 30, at least 40, at least 50, at least 60, at least 70, at least 80, at least 90 or at least 100 amino acids). The conjugation does not necessarily need to be direct, but can occur through a linker. Such linker molecules are commonly known in the art and described in Denardo et al. Clin Cancer Res 4:2483 (1998); Peterson et al. Bioconjug. Chem. 10:553 (1999); Zimmerman et al. Nucl. Med. Biol. 26:943 (1999); Garnett, Adv. Drug Deliv. Rev. 53:171 (2002).

Compositions comprising heterologous proteins, peptides or polypeptides conjugated to an IgG Fc variant domain containing polypeptide are also provided. Methods for fusing or conjugating polypeptides to antibody portions are well known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International publication Nos. WO 96/04388 and WO 91/06570; Ashkenazi et al. Proc. Natl. Acad. Sci. USA 88:10535-39 (1991,); Zheng et al. J. Immunol. 154:5590-5600 (1995); and Vil et al. Proc. Natl. Acad. Sci. USA 89:11337-41 (1992).

In some aspects, an IgG Fc variant domain containing polypeptide is conjugated to a diagnostic or detectable agent. Such conjugates can be useful for monitoring or prognosing the development or progression of an inflammatory disorder as part of a clinical testing procedure, such as determining the efficacy of a particular therapy. Such diagnosis and detection can be accomplished by coupling an IgG Fc variant domain containing polypeptide to detectable substances.

In some aspects, an IgG Fc variant domain containing polypeptide is conjugated to a therapeutic agent. An IgG Fc variant domain containing polypeptide can be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells.

In some aspects, an IgG Fc variant domain containing polypeptide can be conjugated to a therapeutic agent or drug moiety that modifies a given biological response. Therapeutic agents or drug moieties are not to be construed as limited to classical chemical therapeutic agents. For example, the drug moiety can be a protein or polypeptide possessing a desired biological activity. Such proteins can include, for example, a toxin, a cytocine, or a growth factor.

Moreover, an IgG Fc variant domain containing polypeptide can be conjugated to a therapeutic moiety such as a radioactive materials or macrocyclic chelators useful for conjugating radiometal ions (see above for examples of radioactive materials).

An antibody comprising a variant IgG Fc domain described herein, i.e., an antibody variant, can be conjugated to a therapeutic moiety. Techniques for conjugating therapeutic moieties to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56. (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al. Immunol. Rev. 62:119-58 (1982). Alternatively, antibody variant can be conjugated to a second antibody to form an antibody heteroconjugate as described by Segal in U.S. Pat. No. 4,676,980.

In some aspects, an IgG Fc variant domain containing polypeptide comprises one or more engineered glycoforms, i.e., a carbohydrate composition that is covalently attached to the polypeptide. Engineered glycoforms can be useful for a variety of purposes, including but not limited to reducing effector function. Engineered glycoforms can be generated by any method known to one skilled in the art, for example by using engineered or variant expression strains, by co-expression with one or more enzymes, for example DI N-acetylglucosaminyltransferase III (GnTI11), by expressing an IgG Fc variant domain containing polypeptide in various organisms or cell lines from various organisms, or by modifying carbohydrate(s) after an IgG Fc variant domain containing polypeptide has been expressed. Methods for generating engineered glycoforms are known in the art, and include but are not limited to those described in Umana et al., Nat. Biotechnol. 17:176-180 (1999); Davies et al., Biotechnol. Bioeng. 74:288-294 (2001); Shields et al., J. Biol. Chem. 277:26733-26740 (2002); Shinkawa et al., J. Biol. Chem. 278:3466-3473 (2003); Okazaki et al., J. Mol. Biol. 336:1239-49 (2004); U.S. Pat. No. 6,602,684; US Publication No. 2009/0004179, International Publication Nos. WO 00/61739, WO 01/292246, WO 02/311140, WO 02/30954, and WO 07/005786.

Fusion Proteins

An Fc fusion protein combines an Fc domain of an immunoglobulin or fragment thereof, with a fusion partner, which in general can be any protein, polypeptide, peptide, or small molecule. The role of the non-Fc part of the Fc fusion protein, i.e., the fusion partner, is often but not always to mediate target binding, and thus is functionally analogous to the variable regions of an antibody. Accordingly, a fusion protein, i.e., an IgG Fc variant domain containing polypeptide and a fusion partner that specifically binds to a molecule (e.g., a cell surface receptor, chemokine, etc) is provided.

In some aspects, a fusion protein can comprise a peptide, polypeptide, protein scaffold, scFv, dsFv, diabody, Tandab, or an antibody mimetic fused to an IgG Fc variant domain containing polypeptide. In some aspects, a fusion protein can comprises a linker region connecting a peptide, polypeptide, protein scaffold, scFv, dsFv, diabody, Tandab, or an antibody mimetic to an IgG Fc variant domain containing polypeptide. The use of naturally occurring as well as artificial peptide linkers to connect polypeptides into novel linked fusion polypeptides is well known in the literature (Hallewell et al., J. Biol. Chem. 264, 5260-5268 (1989); Alfthan et al., Protein Eng. 8, 725-731 (1995); Robinson & Sauer, Biochemistry 35, 109-116 (1996); Khandekar et al., J. Biol. Chem. 272, 32190-32197 (1997); Fares et al. (1998), Endocrinology 139, 2459-2464; Smallshaw et al. (1999), Protein Eng. 12, 623-630; U.S. Pat. No. 5,856,456).

In some aspects, a fusion protein can combine a variant IgG Fc domain with a fusion partner which in general can be an protein, including, but not limited to, a ligand, an enzyme, the ligand portion of a receptor, an adhesion protein, or some other protein or domain. See, e.g., Chamow et al., Trends Biotechnol. 14:52-60 (1996); Ashkenazi et al., Curr. Opin. Immunol. 9:195-200 (1997); Heidaran et al., FASEB J. 9:140-5 (1995).

In one aspect, a fusion protein can comprise a variant IgG Fc domain fused to a moiety that specifically binds to a target molecule, wherein the target molecule is, for example, a ligand, a receptor or a fragment thereof. A fusion protein can comprise a variant IgG Fc domain comprising the amino acid substitutions described supra, e.g., FQQ, FAQ, or FQG Fc domain mutations and can further comprise substitutions at one or more positions selected from the group consisting of EU positions 252, 254, and 256, e.g., Y, YT, YE, YTE Fc domain mutations.

In a specific aspect, a fusion protein comprises a variant IgG Fc domain comprising a phenylalanine (F) at EU position 234, a glutamine (Q) at EU position 235 and a glutamine (Q) at EU position 322. In some aspects, a fusion protein comprising a FQQ variant IgG Fc domain further comprises a tyrosine (Y) at EU position 252, a threonine (T) at EU position 254, and a glutamic acid (E) at EU position 256.

In another aspect, a fusion protein comprises a variant IgG Fc domain comprising a phenylalanine (F) at EU position 234, a glutamine (Q) at EU position 235, and a glycine (G) at EU position 331. In some aspects, a fusion protein comprising a FQG variant IgG Fc domain further comprises a tyrosine (Y) at EU position 252, a threonine (T) at EU position 254, and a glutamic acid (E) at EU position 256.

In yet another aspect, a fusion protein comprises a variant IgG Fc domain comprising a phenylalanine (F) at EU position 234, an alanine (A) at EU position 235, and a glutamine (Q) at EU position 322. In some aspects, a fusion protein comprising a FAQ variant IgG Fc domain further comprises a tyrosine (Y) at EU position 252, a threonine (T) at EU position 254, and a glutamic acid (E) at EU position 256.

In another aspect, a fusion protein comprises a bioactive molecule fused to a variant IgG Fc domain described herein. Bioactive molecules that can be fused to a variant IgG Fc domain described herein, but are not limited to, peptides, polypeptides, proteins, small molecules, mimetic agents, synthetic drugs, inorganic molecules, and organic molecules. In one aspect, a bioactive molecule is a polypeptide comprising at least 5, at least 10, at least 20, at least 30, at least 40, at least 50, at least 60, at least 70, at least 80, at least 90 or at least 100 contiguous amino acid residues, and is heterologous to the amino acid sequence of a variant IgG Fc domain described herein.

A fusion protein comprising a variant IgG Fc domain described herein can be fused to a marker sequence, such as but not limited to, a peptide, to facilitate purification. In some aspects, the marker amino acid sequence is a His6 tag, a "flag" tag, a hemagglutinin "HA" tag, or one of many others commercially available tags.

A variety of linkers can be used to covalent link an IgG Fc variant domain containing polypeptide to a fusion partner to generate a fusion protein. Alternatively, polypeptides, proteins and fusion proteins can be produced by standard recombinant DNA techniques or by protein synthetic techniques, e.g., by use of a peptide synthesizer.

Recombinant Polypeptide Expression

The recombinant expression of an IgG Fc variant domain containing polypeptide, derivative, analog or fragment thereof, e.g., an antibody variant or a fusion protein comprising a variant IgG Fc domain described herein, can be accomplished through the construction of an expression vector containing a polynucleotide that encodes the polypeptide. Once a polynucleotide encoding an IgG Fc variant domain containing polypeptide (e.g., an antibody variant or a fusion protein) has been obtained, the vector for the production of the polypeptide can be produced by recombinant DNA technology using techniques well known in the art.

Thus, methods for preparing a protein by expressing a polynucleotide containing a nucleotide sequence encoding an IgG Fc variant domain containing polypeptide (e.g., an antibody variant or a fusion protein) are described herein. Methods that are well known to those skilled in the art can be used to construct expression vectors containing coding sequences and appropriate transcriptional and translational control signals. These methods include, for example, in vitro recombinant DNA techniques, synthetic techniques, and in vivo genetic recombination. Thus, replicable vectors are provided which comprise a nucleotide sequence encoding an IgG Fc variant domain containing polypeptide, operably linked to a promoter.

The expression vector is transferred to a host cell by conventional techniques and the transfected cells are then cultured by conventional techniques to produce an IgG Fc variant domain containing polypeptide. Thus, host cells are provided which contain a polynucleotide encoding an IgG Fc variant domain containing polypeptide, operably linked to a heterologous promoter.

A variety of host-expression vector systems can be utilized to express an IgG Fc variant domain containing polypeptide (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express a polypeptide comprising a variant IgG Fc domain in situ. These include but are not limited to microorganisms such as bacteria (e.g., *E. coli* and *B. subtilis*) transformed with recombinant bacteriophage DNA, plasmid DNA or cosmid DNA expression vectors containing a sequence or sequences encoding an IgG Fc variant domain containing polypeptide; yeast (e.g., *Saccharomyces Pichia*) transformed with recombinant yeast expression vectors containing a sequence or sequences encoding an IgG Fc variant domain containing polypeptide; insect cell systems infected with recombinant virus expression vectors (e.g., baculovirus) containing a sequence or sequences encoding an IgG Fc variant domain containing polypeptide; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a sequence or sequences encoding an IgG Fc variant domain containing polypeptide; or mammalian cell systems (e.g., COS, CHO, BHK, 293, NS0, 3T3 cells) harboring recombinant expression constructs containing promoters derived from the genome of mammalian cells or from mammalian viruses.

A host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Eukaryotic host cells which possess the cellular machinery for proper processing of the primary transcript, glycosylation, and phosphorylation of the gene product can be used. Such mammalian host cells include but are not limited to CHO, VERY, BHK, HeLa, COS, MDCK, 293, 3T3, W138, BT483, Hs578T, HTB2, BT20 and T47D, NS0, CRL7O3O and HsS78Bst cells.

For long-term, high-yield production of recombinant proteins, stable expression is often preferred. For example, cell lines which stably express an IgG Fc variant domain containing polypeptide can be engineered using methods known in the art.

Once an IgG Fc variant domain containing polypeptide (e.g., an antibody variant or a fusion protein) has been produced by recombinant expression, it can be purified by any method known in the art for purification of a protein, for example, by chromatography (e.g., ion exchange, affinity, particularly by affinity for the specific antigen after Protein A, and sizing column chromatography), centrifugation, differential solubility, or by any other standard technique for the purification of proteins.

Characterization and Functional Assays

An IgG Fc variant domain containing polypeptide can be characterized in a variety of ways. In particular, an IgG Fc variant domain containing polypeptide can be assayed for the ability to specifically bind to a ligand, e.g., FcγRIIA, FcγRIIIA(158V), C1q. Such an assay can be performed in solution (see, e.g., Houghten, Bio/Techniques 13:412-421 (1992)), on beads (see, e.g., Lam, Nature 354:82-84 (1991)), on chips (see, e.g., Fodor, Nature 364:555-556 (1993)), on bacteria (see, e.g., U.S. Pat. No. 5,223,409), on plasmids (see, e.g., Cull et al., Proc. Natl. Acad. Sci. USA 89:1865-1869 (1992)), or on phage (see, e.g., Scott and Smith, Science 249:386-390 (1990); Devlin, Science 249:404-406 (1990); Cwirla et al., Proc. Natl. Acad. Sci. USA 87:6378-6382 (1990); and Felici, J. Mol. Biol. 222:301-310 (1991)). Molecules that have been identified to specifically bind to a ligand, e.g., FcγRIIA, FcγRIIIA, C1q, can then be assayed for their affinity for the ligand.

An IgG Fc variant domain containing polypeptide can be assayed for specific binding to a molecule such as an antigen (e.g., cancer antigen and cross-reactivity with other antigens) or a ligand (e.g., FcγR) by any method known in the art Immunoassays which can be used to analyze specific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, agglutination assays, complement-fixation assays, fluorescent immunoassays, protein A immunoassays, etc. Such assays are routine and well known in the art. See, e.g., Ausubel et al., eds, 1994, Current Protocols in Molecular Biology, Vol. 1, John Wiley & Sons, Inc., New York.

The binding affinity of an IgG Fc variant domain containing polypeptide to a molecule such as an antigen or a ligand, e.g., FcγR, and the off-rate of the interaction can be determined by competitive binding assays. The kinetic parameters of an IgG Fc variant domain containing polypeptide can also be determined using any surface plasmon resonance (SPR) based assays known in the art (e.g., BIAcore or ProteOn kinetic analysis). See, e.g., Mullet et al. Methods 22: 77-91 (2000); Dong et al. Rev. Mol. Biotech. 82: 303-23 (2002); Fivash et al. Curr. Opin. Biotechnol. 9: 97-101 (1998); Rich et al. Curr. Opin. Biotechnol. 11: 54-61 (2000). Additionally, any of the SPR instruments and SPR based methods for measuring protein-protein interactions described in U.S. Pat. Nos. 6,373,577; 6,289,286; 5,322,798; 5,341,215; 6,268,125 are contemplated in the methods of the present disclosure.

Fluorescence activated cell sorting (FACS), using any of the techniques known to those skilled in the art, can be used for characterizing the binding of an IgG Fc variant domain containing polypeptide to a molecule expressed on the cell surface (e.g., a FcγR).

An IgG Fc variant domain containing polypeptide can assayed for its ability to mediate FcγR-mediated effector cell function. Examples of effector cell functions that can be assayed include, but are not limited to, antibody-dependent cell mediated cytotoxicity (ADCC), C1q binding, and complement dependent cell mediated cytotoxicity (CDC). Any cell-based or cell free assay known to those skilled in the art for determining effector cell function activity can be used (see, e.g., Perussia et al. Methods Mol. Biol. 121: 179-92 (2000); Baggiolini et al. Experientia 44: 841-8 (1998); Lehmann et al. J. Immunol. Methods 243: 229-42 (2000); Brown, Methods Cell Biol. 45: 147-64 (1994); Munn et al. J. Exp. Med. 172: 231-237 (1990); Abdul-Majid et al. Scand. J. Immunol. 55:70-81 (2002); Ding et al. Immunity 8:403-411 (1998)). In particular, an IgG Fc variant domain containing polypeptide can be assayed for FcγR-mediated ADCC activity in effector cells, e.g., natural killer cells, using any of the standard methods known to those skilled in the art (see, e.g., Perussia et al. Methods Mol. Biol. 121: 179-92 (2000)).

Methods to characterize the ability of an IgG Fc variant domain containing polypeptide to bind C1q and mediate complement dependent cytotoxicity (CDC) are well known in the art. For example, to determine C1q binding, a C1q binding ELISA can be performed. To assess complement activation, a complement dependent cytotoxicity (CDC) assay can be performed, e.g., as described in Gazzano-Santoro et al. J. Immunol. Methods 202:163 (1996).

Pharmaceutical Compositions and Methods of Administration

In another aspect, compositions are provided which comprise an IgG Fc variant domain containing polypeptide, a nucleic acid encoding an IgG Fc variant domain containing polypeptide, or combinations thereof formulated together with a carrier. Such compositions can include one or a combination of (e.g., two or more different) antibodies, fusion proteins, or conjugates. In some aspects, such compositions are physiologically tolerable and as such are suitable for therapeutic, prophylactic, or diagnostic administration to a subject.

In another aspect, compositions comprising an IgG Fc variant domain containing polypeptide (e.g., an antibody variant, a fusion protein, or a conjugate) or a nucleic acid encoding an IgG Fc variant domain containing polypeptide can include one or more pharmaceutically acceptable salts.

Examples of suitable aqueous and nonaqueous carriers that can be employed in contemplated compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

In another aspect, compositions comprising an IgG Fc variant domain containing polypeptide (e.g., an antibody variant, a fusion protein, or a conjugate) or a nucleic acid encoding an IgG Fc variant domain containing polypeptide can also contain agents such as preservatives, wetting agents, emulsifying agents and dispersing agents. Prevention of presence of microorganisms can be ensured both by sterilization procedures and by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions is contemplated. Supplementary active compounds can also be incorporated into the compositions. In some aspects, acceptable carriers include excipients approved for or considered to be safe for human and animal administration, i.e., GRAS substances (generally regarded as safe). GRAS substances are listed by the Food and Drug administration in the Code of Federal Regulations (CFR) at 21 CFR 182 and 21 CFR 184, incorporated herein by reference.

Actual dosage levels of the active ingredients in pharmaceutical compositions comprising an IgG Fc variant domain containing polypeptide (e.g., an antibody variant, a fusion protein, or a conjugate) or a nucleic acid encoding an IgG Fc variant domain containing polypeptide can be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A therapeutically effective dosage of an IgG Fc variant domain containing polypeptide, a nucleic acid encoding an IgG Fc variant domain containing polypeptide, or a pharmaceutical composition thereof results in a decrease in severity of disease symptoms, an increase in frequency and duration of disease symptom-free periods, or a prevention of impairment or disability due to the disease affliction. A therapeutically effective dose can also prevent or delays onset of disease. Accordingly, any clinical or biochemical monitoring assay can be used to determine whether a particular treatment is a therapeutically effective dose. One of ordinary skill in the art would be able to determine such amounts based on such factors as the subject's size, the severity of the subject's symptoms, and the particular composition or route of administration selected.

A composition comprising an IgG Fc variant domain containing polypeptide (e.g., an antibody variant, a fusion protein, or a conjugate) or a nucleic acid encoding an IgG Fc variant domain containing polypeptide can be administered via one or more routes of administration using one or more of a variety of methods known in the art. As will be appreciated by the skilled artisan, the route and/or mode of administration will vary depending upon the desired results. Selected routes of administration compositions comprising an IgG Fc variant domain containing polypeptide, a nucleic acid encoding an IgG Fc variant domain containing polypeptide, and pharmaceutical compositions thereof include intravenous, intramuscular, intradermal, intraperitoneal, subcutaneous, spinal or other parenteral routes of administration, for example by injection or infusion. Parenteral administration can represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, compositions comprising an IgG Fc variant domain containing polypeptide, a nucleic acid encoding an IgG Fc variant domain containing polypeptide, and pharmaceutical compositions thereof can be administered via a non-parenteral route, such as a topical, epidermal or mucosal route of administration, for example, intranasally, orally, vaginally, rectally, sublingually or topically.

Methods of Treatment

An IgG Fc variant domain containing polypeptide (e.g., an antibody variant, a fusion protein, or a conjugate) or a nucleic acid encoding an IgG Fc variant domain containing polypeptide can be administered to an animal, in particular a mammal, specifically, a human, for preventing, treating, or ameliorating one or more symptoms associated with a disease, disorder, or infection.

An IgG Fc variant domain containing polypeptide or a nucleic acid encoding an IgG Fc variant domain containing polypeptide can be particularly useful for the treatment or prevention of diseases or disorders where an altered efficacy of effector cell function (e.g., ADCC and/or CDC) is desired.

An IgG Fc variant domain containing polypeptide or a nucleic acid encoding an IgG Fc variant domain containing polypeptide, and compositions thereof can be particularly useful for the treatment or prevention of primary or metastatic neoplastic disease (i.e., cancer), autoimmune disease, and infectious diseases. An IgG Fc variant domain containing polypeptide or a nucleic acid encoding an IgG Fc variant domain containing polypeptide can be provided in pharmaceutically acceptable compositions as known in the art or as described herein. As detailed below, an IgG Fc variant domain containing polypeptide or a nucleic acid encoding an IgG Fc variant domain containing polypeptide can be used in methods of treating or preventing cancer (particularly in passive immunotherapy), autoimmune disease, inflammatory disorders or infectious diseases.

An IgG Fc variant domain containing polypeptide or a nucleic acid encoding an IgG Fc variant domain containing polypeptide, and compositions thereof can also be advantageously utilized in combination with other therapeutic agents known in the art for the treatment or prevention of a cancer, autoimmune disease, inflammatory disorders or infectious diseases. An IgG Fc variant domain containing polypeptide or a nucleic acid encoding an IgG Fc variant domain containing polypeptide, and compositions thereof can also be advantageously utilized in combination with one or more drugs used to treat a disease, disorder, or infection such as, for example anti-cancer agents, anti-inflammatory agents or anti-viral agents.

In some aspects, methods for preventing, treating, or ameliorating one or more symptoms associated with cancer and related conditions by administering an IgG Fc variant domain containing polypeptide or a nucleic acid encoding an IgG Fc variant domain containing polypeptide are provided.

An IgG Fc variant domain containing polypeptide or a nucleic acid encoding an IgG Fc variant domain containing polypeptide can be used for preventing, treating, or managing one or more symptoms associated with an inflammatory disorder in a subject.

The disclosure also encompasses methods for treating or preventing an infectious disease in a subject comprising administering a therapeutically or prophylactically effective amount of an IgG Fc variant domain containing polypeptide. Infectious diseases that can be treated or prevented by an IgG Fc variant domain containing polypeptide are caused by infectious agents including but not limited to viruses, bacteria, fungi, protozae, and viruses.

Kits

Also provided is a pharmaceutical pack or kit comprising one or more containers filled with one or more of the pharmaceutical compositions disclosed herein. Optionally associated with such container(s) can be a notice in the form prescribed by a governmental agency regulating the manufacture, use or sale of pharmaceuticals or biological products, which notice reflects approval by the agency of manufacture, use or sale for human administration. The present disclosure provides kits that can be used in the above methods of treatment and administration. In one aspect, a kit comprises an IgG Fc variant domain containing polypeptide (e.g., an antibody variant, a fusion protein, or a conjugate), preferably in a purified form, in one or more containers.

EXAMPLES

These examples are provided for the purpose of illustration only and should in no way be construed as limiting the claims but rather should be construed to encompass any and all variations which become evident as a result of the teachings provided herein.

Example 1

Variant IgG Fc Domain Generation and Antibody Production and Purification

Mutations were introduced into the Fc region of the heavy chain of the anti-RSV glycoprotein F humanized monoclonal antibody motavizumab (MEDI 532, Numax™; see Wu et al., J. Mol. Biol. 350:126-144 (2005); Wu et al., J. Mol. Biol. 368:652-65 (2007)) (hereinafter referred to as "Ab1"), an anti-IL-4R antibody (see e.g., U.S. Pat. No. 8,092,804) (hereinafter referred to as "Ab2"), the anti-CD20 antibody HB20.3 (see e.g., US 2009/0136516; US 2009/0155275) (hereinafter referred to as "Ab3"), or the anti-C5a antibody 1B8 (hereinafter referred to as "Ab4"). Mutations were introduced by site-directed mutagenesis using PCR by overlap extension (see, e.g., Ho et al., Gene 77:51-59 (1989)). Primers containing the desired mutations were used to amplify regions of the heavy chain gene. These fragments were then combined (if necessary) to generate full length human IgG1 Fc gene fragments with the desired mutation. The final PCR fragments were then individually cloned into heavy chain-encoding mammalian expression vectors. This process resulted in the replacement of the wild type heavy chain constant portion of the antibody by the different Fc-modified counterparts. DNA sequencing used to verify the constructs was performed by Genewiz (South Plainfield, N.J.), All constructs were transiently expressed in HEK293F cells using 293Fectin™ (Invitrogen) as a transfection reagent and grown in Invitrogen's serum-free Freestyle™ medium. The culture medium was collected 10 days after transfection, and all antibody formats were purified by standard protein A affinity chromatography in accordance with the manufacturer's protocol (GE Healthcare, Piscataway, N.J.). Antibodies were subsequently buffer exchanged in 25 mM histidine-HCl (pH 6.0) and the purity of the constructs was analyzed using SDS-PAGE under reducing and non-reducing conditions and with analytical size-exclusion chromatography. Preparative size-exclusion chromatography was used to attain 99 to 100% pure IgG samples.

Example 2

Differential Scanning Calorimetry (DSC) and SYPRO® Orange Differential Scanning Fluorimetry (DSF) Thermal Stability Measurements Instability of IgG domains can correlate with unfavorable Chemistry, Manufacturing, and Control (CMC) properties such as decreased thermal stability and solubility, increased aggregation or fragmentation ultimately leading to increased purity loss, limited formulation/delivery options and other developability challenges.

DSC experiments were carried out using a Microcal VP-DSC differential scanning microcalorimeter (Microcal, Northampton, Mass.). All solutions and samples used for DSC were filtered using a 0.22-μm filter and degassed prior to loading into the calorimeter. Antibodies used for the DSC studies were >95% monomeric as judged by analytical gel filtration chromatography. Prior to DSC analysis all samples were exhaustively dialyzed (at least three buffer exchanges) in 25 mM histidine-HCl (pH 6). Buffer from this dialysis was then used as reference buffer for subsequent DSC experiments. Prior to sample measurement, baseline measurements (buffer-versus-buffer) were obtained to be subtracted from the sample measurement. Dialyzed samples (at a concentration of 1 mg/ml) were added to the sample well and DSC measurements were performed at a 1° C./min scan rate. Data analysis and deconvolution were carried out using the Origin™ DSC software provided by Microcal.

For DSF experiments, SYPRO® Orange was added to antibodies at 0.5 mg/ml concentration in 25 mM histidine-HCl (pH 6) (Goldberg et al., J. Pharm. Sci. 100: 1306-1315 (2011)). Twenty-five microliters of prepared samples was added in duplicate to white-walled PCR plates. A Chromo4 Real Time PCR Detector (Bio-Rad, Hercules, Calif.) was used as a thermal cycler, and the fluorescence emission was detected using the software's custom dye calibration routine. The PCR plate containing the test samples was subjected to a temperature ramp from 20° C. to 90° C. in increments of 0.2° C. with 10 second pauses after each temperature increment. The $T_m$ was calculated by the software using a mathematical second derivative method to calculate the inflection point of the curve. The reported $T_m$ is an average of three measurements.

Mutations were introduced into the Fc region of Ab1 or Ab2. When both FES and YTE mutations were introduced to the Fc domains of Ab1 and Ab2 (see data corresponding to IgG1-FES-YTE on TABLE 1), decreased thermal stability and increased purity loss were observed. Ab1 and Ab2 displayed a 14° C. and 13° C. loss respectively in thermal stability (as measured by DSC). The FES-YTE antibody variants (IgG1-FES-YTE antibodies in TABLE 2) also showed significantly increased purity loss than either their wild-type or YTE counterparts (when measured at 40° C. for a month using an accelerated stability assay).

TABLE 2

DSC and Accelerated Stability Measurements in Ab1 and Ab2 Antibodies

|  | IgG1 WT | IgG1-YTE | IgG1-FES-YTE |
|---|---|---|---|
| Ab1 | | | |
| Lowest $T_m$ (° C.)* | 70 | 63 | 56 |
| % Purity Loss/month at 40° C.* | 1.1 | 1.2 | 2.6 |
| Ab2 | | | |
| Lowest $T_m$ (° C.)* | 68 | 61 | 55 |
| % Purity Loss/month at 40° C.* | 6.0 | 6.8 | 8.4 |

Figure 1:
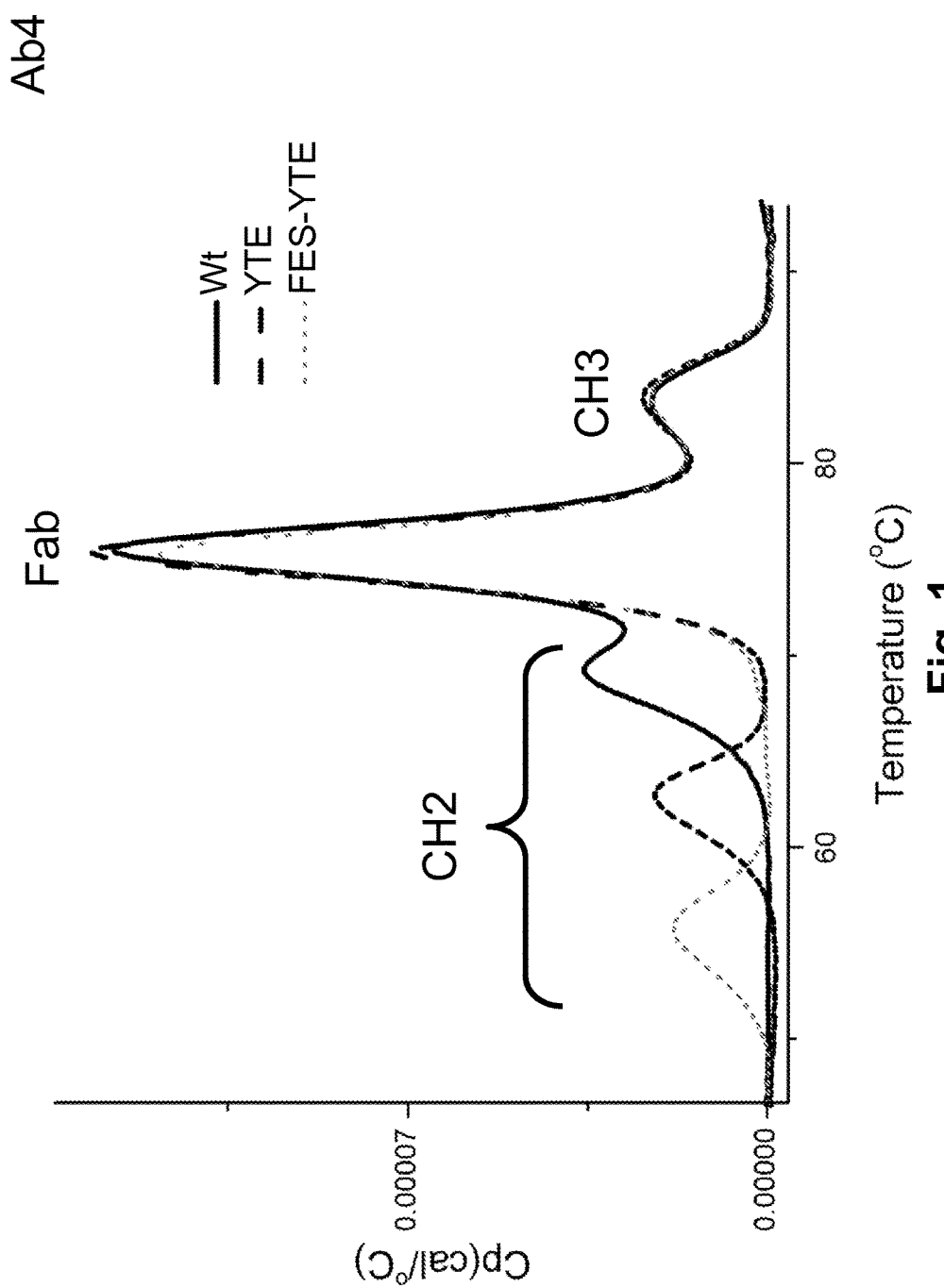
FIG. 1 shows differential scanning calorimetry (DSC) thermograms of Ab4 antibodies comprising wild-type (Wt) Fc domains, and of Ab4 antibodies comprising YTE and FES-YTE variant Fc domains. The locations of the denaturations peaks corresponding to the antibody's Fab region, and CH2 and CH3 regions are indicated.

For 100 mg/ml protein in 25 mM histidine pH 6 buffer
Relative Stability: WT ≅ YTE > FES-YTE
*Lowest antibody $T_m$ corresponds with CH2 domain $T_m$ Thermal instability upon the addition of the YTE set of mutations or the FES-YTE affected the CH2 domain exclusively (FIG. 1). DSC traces of Ab4 showed that the CH2 domain $T_m$ decreased with the addition of the YTE and FES-YTE mutations, but the thermal stability of the Fab and CH3 domains remained unaffected. Although thermal stability decreased with the addition of YTE (see TABLE 1 and FIG. 1), significant increases in purity loss only began when the FES mutations were introduced in combination with the YTE mutations.

To aid in constructing a more thermal stable variant Fc domain with the same biological properties as a variant Fc domain with the FES-YTE mutations, we determined the contribution to thermal stability of each FES mutations via dissection mutagenesis and the results showed that the EU L234F mutation had no effect on thermal stability, whereas the EU L235E mutation and the EU P331S mutation displayed approximately a −2.5 and −3.5° C., respectively, reduction in thermal stability as determined by DSC on Ab3-YTE background (i.e., the EU L234F, EU L235E, and EU P331S mutations were introduced in a Ab3 antibody whose Fc domains already contained the YTE mutations).

Alternate mutations at the L235 and P331 EU positions of the Fc domain were generated and assessed for enhanced thermal stability (TABLE 3). As the EU P331S substitution is primarily included in FES mutants to lower C1q binding, we also chose an alternate site, at EU position K322 (also known to lower C1q binding) to mutagenize as well (Idusogie et al., J. Immunol. 164: 4178-4184 (2000)).

All the antibodies comprising variant Fc domains with the chosen mutations (I, A, N, F, Q, and V) at EU position L235 displayed enhanced thermal stability versus the corresponding antibodies comprising a variant Fc domain with the EU L235E mutation by approximately 2° C. in the L234F YTE Ab3 background.

At EU position P331, alanine and glycine mutations improved thermal stability only modestly (1° C.) when compared to antibodies with Fc domains with the FES-YTE mutations (mutations were introduced in the EU L234F L235E YTE Ab3 background). At EU position K322 (the alternate site to EU position P331) mutations to A, E, N, H, and Q were created and analyzed for thermal stability increases. The EU K322E, K322N and K322H substitutions actually resulted in decreased thermal stability compared to FES-YTE. When these mutations were introduced in the EU L234F L235E YTE Ab3 background the CH2 Tm decreased 0.3, 7, and 2.6° C. respectively. The EU K322A and K322Q mutations in the EU L234F L235E YTE Ab3 background resulted in improvements in thermal stability versus FES-YTE of 1.2 and 2.8° C. respectively.

TABLE 3

Mutations Enhancing Thermal Stability

| EU Position | Mutations | Thermal Stability enhancement* |
|---|---|---|
| L235 | I, A, N, F, Q, V | ~2° C. |
| P331 | A, G† | ~1° C. |
| K322‡ | Q | ~3° C. |

Mutations at EU L235 were generated in the (L234F-YTE) Ab3 Background; Mutations at EU P331 and EU K322 were generated in the (L234F, L235E-YTE) Ab3 Background
*Enhancement over EU L234F/L235E/M252Y/S254T/T256E (FE-YTE) for EU L235; Enhancement over EU L234F/L235E/P331S/M252Y/S254T/T256E (FES-YTE) for EU P331 and EU K322
†More effective at knocking out CDC
‡Mutation at EU K322 replaces mutation at EU P331

We next made constructs that combined the most thermal stable mutations at EU positions L235 and P331 or K322 to assess for thermal stability improvements, improvements in purity loss and biophysical stability as well as maintained desired biological properties (such as enhanced FcRn binding and lack of ADCC and CDC induction).

Figure 2:
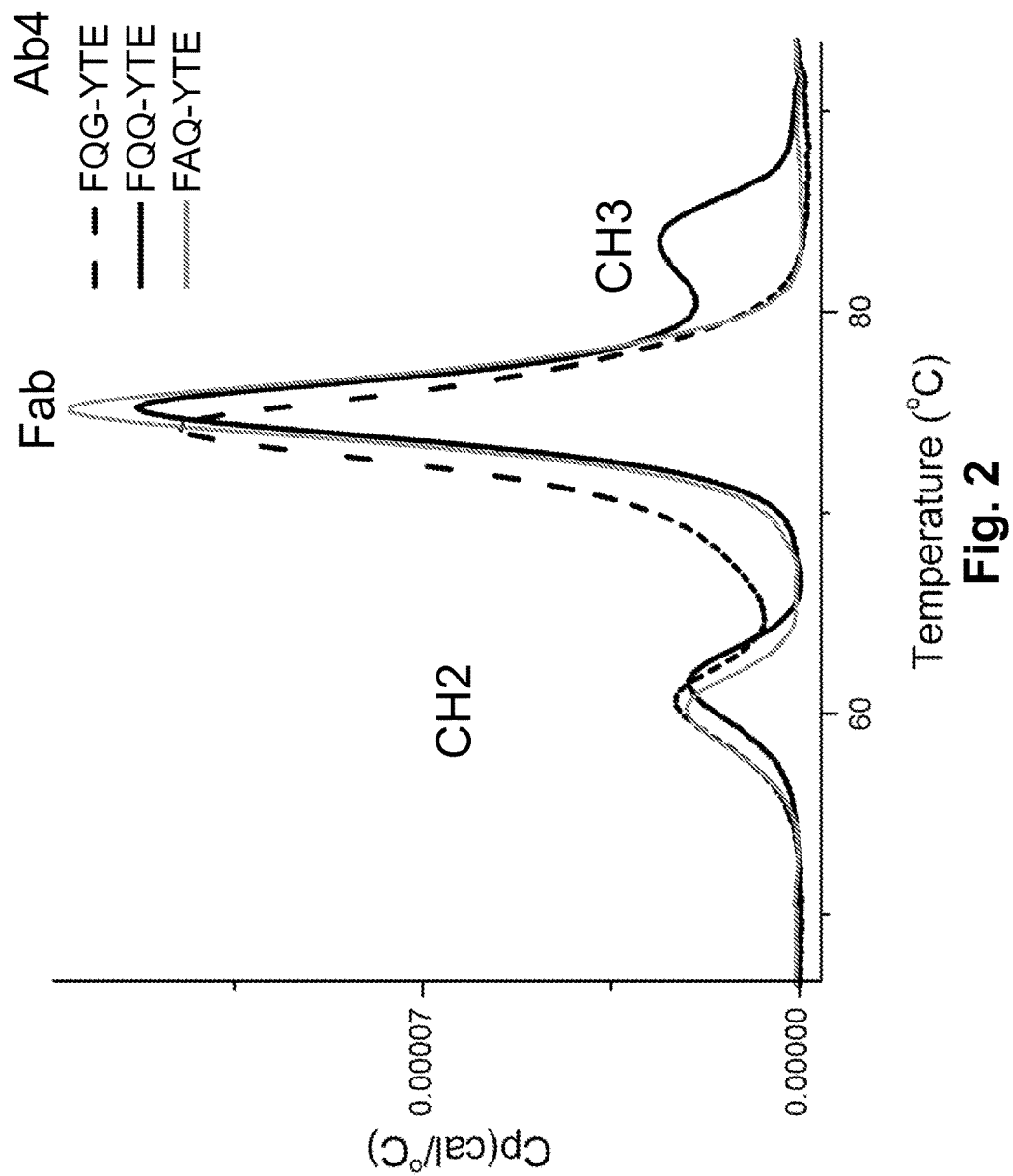
FIG. 2 shows differential scanning calorimetry (DSC) thermograms of Ab4 antibodies comprising FQG-YTE, FQQ-YTE and FAQ-YTE variant Fc domains. The locations of the denaturations peaks corresponding to the antibody's Fab region, and CH2 and CH3 regions are indicated.

FQG-YTE, FQQ-YTE, and FAQ-YTE variant Fc domains were generated in Ab3 and Ab4 backgrounds. Ab3 and Ab4 variants comprising FQG-YTE, FQQ-YTE, and FAQ-YTE variant Fc domains showed significant thermal stability improvement (FIG. 2) versus the Ab3 and Ab4 variants comprising FES-YTE mutations (FIG. 1).

In the Ab3 background, FES-YTE mutants had a CH2 $T_m$ of 55.6° C. In contrast, Ab3 variants with FAQ-YTE, FQG-YTE, and FQQ-YTE mutations had CH2 $T_m$s of 60.6° C., 60.2° C., and 61.6° C., respectively (TABLE 4) indicating that these combinations of Fc domain mutations indeed conferred improved thermal stability to the CH2 domain.

TABLE 4

DSC and DSF results.

| Ab3 | DSC *$T_m1$° C. | SYPRO Orange *$T_m1$° C. |
|---|---|---|
| WT | 69.2 (+13.6) | 65.6 (+12.6) |
| YTE | 62.7 (+7.1) | 59.2 (+6.2) |
| YTE-FES | 55.6 | 53 |
| YTE-FE | 60 (+4.4) | 56.6 (+3.6) |
| YTE-FQQ | 61.6 (+6) | 59 (+6) |
| YTE-FAQ | 60.6 (+5) | 59 (+6) |
| YTE-FQG | 60.2 (+4.6) | 58.9 (+5.9) |

Values in ( ) are $T_m1$ improvement over FES-YTE
*$T_m1$ corresponds with CH2 domain

Example 3

Surface Plasmon Resonance Binding Analysis

Antibodies comprising variant IgG Fc domains with the three combined mutants FQQ, FQF, and FAQ and the YTE mutations were tested for binding to FcγR receptors, C1q and FcRn to confirm that they possessed the same binding profile as antibodies comprising variant IgG Fc domains with the FES-YTE mutations.

Experiments were performed using the ProteOn XPR36 surface plasmon resonance system (Bio Rad). Phosphate buffered saline with 0.005% Tween 20 (PBS/Tween), pH 7.4 was used as running buffer for most experiments with the exception of Human FcRn (extracellular domain) binding in which Phosphate buffered saline with 0.005% Tween 20

(PBS/Tween), pH 6.0 was used. All experiments were performed at 25° C. Antibodies were immobilized on a ProteOn™ GLC Sensor Chip (#176-5011) using EDAC (1-Ethyl-3-[3-dimethylaminopropyl]carbodiimide) and sulfo-NHS (N-hydroxysulfosuccinimide) to an R.U. (response unit) level of 4000-6000. C1q, FcγRI, FcγRIIa, FcγRIIb, FcγRIII(158V), FcγRIII(158F), and FcRn were then flowed over the IgG immobilized surface at various concentrations at a rate of 25 μl/minute for a long enough period of time to achieve steady state, or near steady state. Binding (if any could be determined) was quantified via steady state equilibrium binding analysis using the ProteOn software. Human FcγRI, FcγRIIa, FcγRIIb, FcγRIII(158V), FcγRIII(158F), and FcRn extracellular domains were generated via mammalian expression vectors in house. Human C1q was obtained from Quidel (CA).

Antibodies comprising variant IgG Fc domains with FES-YTE, FAQ-YTE, FQG-YTE, or FQQ-YTE mutations did not show quantifiable binding to FcγRIa, FcγRIIa, FcγRIIb, FcγRIIIa(158V), FcγRIIIa(158F), or C1q via SPR (ProteOn) (TABLES 5 and 6). FcRn binding for antibodies comprising variant IgG Fc domains with FQQ-YTE or FQG-YTE mutations were similar to values obtained for antibodies comprising variant IgG Fc domains with FES-YTE or YTE mutations, indicating that improved FcRn binding at pH 6.0 is maintained (TABLES 5 and 6).

background. A Natural Killer cell line expressing CD16 was used as effector cells with Daudi cells being the target. Daudi and effector cells were washed in PBS and diluted to a density of 800,000 c/ml. Daudi and effector cells were added to white V-welled 96 well plates (50 μl each). Ab3 antibody variants at various concentrations were then added to the wells. Cells and antibodies were incubated for 4 hours at 37° C. Daudi cell death was also monitored by analysis of LDH release using the CytoTox 96 nonradioactive cytotoxicity assay (Promega) per manufacturer's instructions.

In experiments using a cell line derived from Natural Killer (NK) cells as effector cells, and Daudi cells as targets, WT Ab3 antibodies and Ab3 antibodies comprising variant IgG Fc domains with YTE mutations gave a titratable ADCC response. Conversely, Ab3 antibodies comprising variant IgG Fc domains with FAQ-YTE, FQQ-YTE, or FES-YTE mutations elicited no significant cytotoxicity even at concentrations up to 300 μg/ml (FIG. 3).

Example 5

Complement Dependent Cytotoxicity (CDC) Assays

Complement dependent cytotoxicity (CDC) assays were performed with variant IgG Fc domains incorporated into Ab3 (HB20.3 anti-CD20; SEQ ID NOs:5 and 6). Human serum from healthy donors was used as a complement

TABLE 5

FcγR Receptor, C1q, and FcRn Binding to Ab3 Variants Measured by SPR

| Ab3 | FcγRIIIa (158 V) | FcγRIIIa (158 F) | FcγRIIa | FcγRIIb | FcγRIa | C1q | FcRn |
| --- | --- | --- | --- | --- | --- | --- | --- |
| WT | 900 nM | 4.7 μM | 1.2 μM | 6 μM | 78 nM | 103 Nm | 670 nM |
| YTE | 800 nM | 6.1 μM | 2.8 μM | 1.6 μM | 140 nM | 70 nM | 235 nM |
| FES-YTE | - - - | - - - | - - - | - - - | - - - | - - - | n.d. |
| FE-YTE | - - - | - - - | - - - | - - - | - - - | 360 nM | n.d. |
| FQQ-YTE | - - - | - - - | - - - | - - - | - - - | - - - | n.d. |
| FAQ-YTE | - - - | - - - | - - - | - - - | - - - | - - - | n.d. |
| FQG-YTE | - - - | - - - | - - - | - - - | - - - | - - - | n.d. |

- - - indicates binding to low to be determined

TABLE 6

FcγR Receptor, C1q, and FcRn Binding to Ab4 Variants Measured by SPR

| Ab3 | FcγRIIIa (158 V) | FcγRIIIa (158 F) | FcγRIIa | FcγRIIb | FcγRIa | C1q | FcRn |
| --- | --- | --- | --- | --- | --- | --- | --- |
| WT | 380 nM | 1.6 μM | 1 μM | 2.5 μM | 31 nM | 250 nM | 1070 nM |
| YTE | 820 nM | 2.8 μM | 1.9 μM | 3.6 μM | 43 nM | 400 nM | 270 nM |
| FES-YTE | - - - | - - - | - - - | - - - | - - - | - - - | 270 nM |
| FE-YTE | - - - | - - - | - - - | - - - | - - - | * | n.d. |
| FQQ-YTE | - - - | - - - | - - - | - - - | - - - | - - - | 290 nM |
| FAQ-YTE | - - - | - - - | - - - | - - - | - - - | - - - | n.d. |
| FQG-YTE | - - - | - - - | - - - | - - - | - - - | - - - | 350 nM |

- - - indicates binding to low to be determined
* Indicates residual binding

SPR binding experiments thus indicated that antibodies comprising variant IgG Fc domain with FAQ-YTE, FQG-YTE, or FQQ-YTE mutations lacked binding to cellular receptors known to be essential for ADCC and the soluble receptor C1q that can initiate CDC.

Example 4

Antibody Dependent Cellular Cytotoxicity (ADCC) Assays

Antibody Dependent Cellular Cytotoxicity (ADCC) assays were performed with variant IgG Fc domains incorporated into Ab3 (HB20.3 anti-CD20; SEQ ID NOs:5 and 6)

source with Daudi cells as the effector cells. Daudi cells were washed in PBS and diluted to a density of 800,000 c/ml. Cells were then added to a white V bottom plate (50 μl each). Diluted serum was then added (50 μl) at the desired concentration along with antibody variants at various dilutions. Cells were incubated at 37° C. for 4 hours. Then, alamar blue reagent (Life Technologies) was added and Daudi cell death was quantified 12 hours later (per manufacturer's instructions).

Only WT Ab3 antibodies or Ab3 antibodies with Fc domains comprising YTE mutations were shown to elicit robust complement dependent cytotoxicity. In contrast, Ab3 antibodies comprising variant IgG Fc domains with FAQ-YTE, FQG-YTE, FQQ-YTE, FES-YTE mutations failed to elicit complement dependent cytotoxicity (FIG. 4).

Example 6

Accelerated Stability Studies

Antibody variants in the Ab4 antibody (1B8 anti-C5a antibody; SEQ ID NOS: 7 and 8) background were concentrated to 100 mg/ml in 25 mM histidine pH 6.0. Antibodies were placed in glass vials and stored in a (40° C., 75% Relative Humidity) controlled chamber for 6 weeks. Samples were tested at weekly intervals for percent aggregate by high-performance size exclusion chromatography (HPSEC). HPSEC analysis was performed on an Agilent HPLC system with a TSK-Gel G3000 column (Agilent Technologies). The eluted protein was detected using UV absorbance at 280 nm and the results were reported as the area percent of the product monomer peak. Peaks eluting earlier than the monomer were recorded as percent aggregate and peaks eluting after the monomer were recorded as percent fragment/other. Aggregation rates over time were determined by linear regression.

Accelerated stability studies were performed to assess any improvements in aggregation/fragmentation rates for antibodies comprising variant IgG Fc domains with FAQ-YTE, FQG-YTE, FQQ-YTE mutation versus antibodies comprising variant IgG Fc domains with FES-YTE mutations (TABLE 7). The FES-YTE antibody variant (in Ab4 background) had a 1.93% aggregation rate at 40° C. for a month while the Ab4 antibodies with the FQG-YTE and FQQ-YTE mutations showed an improvement to 1.01% and 1.1% respectively.

The Ab4 antibodies with the FES-YTE mutations had an overall monomer loss rate of 3.82% per month, whereas WT Ab4 antibodies and Ab4 antibodies with YTE mutations had an overall monomer loss rate of 2.71% and 2.75% per month, respectively. Ab4 antibodies with FQQ-YTE and FQG-YTE mutations had improved overall monomer loss rates at 40° C. compared to Ab4 antibodies with FES-YTE mutations of 3.28% and 3.36%. Ab4 antibodies with FAQ-YTE mutations had higher than expected monomer loss/month due to a higher fragmentation rate (5.74%).

TABLE 7

Accelerated Stability and DSC Data for Ab4 Antibody Variants

|  | WT | YTE | FES-YTE | FQQ-YTE | FQG-YTE | FAQ-YTE |
|---|---|---|---|---|---|---|
| Tm1 ° C. (DSC) | 69.2 | 62.7 | 55.6 | 61.6 | 60.1 | 60.6 |
| 40° C. % monomer loss/month | 2.71 | 2.75 | 3.82 | 3.28 | 3.36 | 6.43 |
| 40° C. % Aggregate loss/month | 0.61 | 0.75 | 1.93 | 1.1 | 1.01 | 0.69 |
| 40° C. % Fragment loss/month | 2.11 | 2.04 | 1.95 | 2.18 | 2.36 | 5.74 |

Example 7

Isoelectric Focusing (IEF) Gels

Pre-cast ampholine gels (Amersham Biosciences, Uppsala Sweden; pI range 3.5-9.5) were loaded with IgG. Broad range pI marker standards (Amersham Biosciences, pI range 3-10) were used to determine relative pI for the various antibodies or antibody fragments. Electrophoresis was performed at 1500 V, 50 mA for 105 min. Gels were fixed for 45 min using Sigma fixing solution (Sigma, Saint Louis, Mo.). Staining was performed overnight at room temperature using Simply Blue stain (Invitrogen). Destaining was carried out with a solution that consisted of 25% ethanol, 8% acetic acid and 67% purified water.

Analysis by IEF gel showed that the introduction of FAQ-YTE, FQG-YTE, and FQQ-YTE mutations in the Fc domains of Ab4 antibodies (1B8 anti-C5a antibody; SEQ ID NOS: 7 and 8) had a minimal affect on pI with all of the constructs near a pI of >8.3 (FIG. 5).

Example 8

Apparent Solubility by Polyethylene Glycol (PEG) Precipitation

PEG precipitation assays were carried out similarly to Gibson et al., J. Pharm. Sci. 100: 1009-1021 (2011). Addition of increasing amounts of PEG 6000 was used to precipitate the antibody. PEG 6000 solutions ranging from 0% to 40% [w/v] PEG were prepared in 50 mM sodium phosphate buffer pH 7.2. These solutions were added to wells of a 96-well white, polystyrene filter plate. Antibodies were then added to wells with varying levels of PEG to a final protein concentration of 1 mg/mL. The 96-well plate(s) were incubated overnight at room temperature. The plates were then centrifuged and the filtrate was collected in a clear polystyrene 96-well collection plate. After transferring equal volumes of each sample filtrate to a fresh, clear polystyrene 96-well plate, the filtrate was analyzed for protein concentration by measuring absorbance at 280 nm with a nanodrop. Apparent solubility is calculated using the slope of the aggregation transition.

Ab4 antibodies (1B8 anti-C5a antibody; SEQ ID NOS: 7 and 8) comprising variant Fc domains with FAQ-YTE, FQG-YTE, and FQQ-YTE mutations were assessed for improved apparent solubility assessed by PEG precipitation (TABLE 8). Extrapolation of the aggregation transition can give a measure of "apparent solubility." This value is useful for ranking antibody variants only, as absolute values do not indicate actual solubility limits (e.g., values for highly soluble proteins are overestimated).

Ab4 antibodies comprising variant Fc domains with FES-YTE mutations gave the poorest apparent solubility result of all antibodies tested at <10 mg/ml. Ab4 antibodies comprising variant Fc domains with FAQ-YTE, FQG-YTE, FQQ-YTE all had high apparent solubility scores >100 mg/ml indicating improved solubility properties over FES-YTE.

TABLE 8

Apparent solubility ranking of Ab4 antibodies comprising variant IgG Fc domains

| Ab4 | Apparent Solubility mg/ml | Rank |
|---|---|---|
| WT | >100 | 1 |
| FQQ-YTE | >100 | 1 |
| YTE | >100 | 2 |
| FQG-YTE | >100 | 2 |
| FAQ-YTE | >100 | 3 |
| FES-YTE | <10 | 4 |

Example 9

Dynamic Light Scattering (DLS)

Protein size distribution and molecular size were monitored by dynamic light scattering (DLS) using a Zetasizer Nano ZS (Malvern Instruments, Malvern, Pa.). The sample (in 1 mg/ml in 25 mM histidine-HCl pH 6) was illuminated using a 633 nm laser, and the intensity of scattered light was measured at an angle of 173 degrees. Samples analyzed at room temperature were incubated on the laboratory bench top for approximately 90 minutes prior to sampling. Prior to each sample analysis, correction factors were introduced for parameters such as viscosity, refractive index and absorbance.

Variants of the Ab4 antibody (1B8 anti-C5a antibody; SEQ ID NOS: 7 and 8) comprising FAQ-YTE, FQG-YTE, FQQ-YTE mutations in their respective Fc domains, as well as wild type Ab4 and variants comprising FES-YTE and YTE mutations in their respective Fc domains were all found to be monodisperse via dynamic light scattering (DLS) (TABLE 9). Thus, the introduction of the FAQ-YTE, FQG-YTE, FQQ-YTE mutation combinations in the Fc domain of Ab4 antibodies did not cause increased polydispersity.

TABLE 9

Assessment of antibody polydispersity by dynamic light scattering (DLS)

| Variant | Hydrodynamic Size (d · nm) | Polydispersity |
|---|---|---|
| WT | 10.80 | 0.02 |
| YTE | 11.06 | 0.04 |
| FES-YTE | 10.84 | 0.02 |
| FAQ-YTE | 10.84 | 0.03 |
| FQG-YTE | 11.06 | 0.04 |
| FQQ-YTE | 11.04 | 0.03 |

The foregoing description of the specific aspects will so fully reveal the general nature of the disclosure that others can, by applying knowledge within the skill of the art, readily modify and/or adapt for various applications such specific aspects, without undue experimentation, without departing from the general concepts provided. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, or other documents cited in this application are incorporated by reference in their entirety for all purposes to the same extent as if each individual publication, patent, patent application, or other document were individually indicated to be incorporated by reference for all purposes. In addition, U.S. Provisional Patent Application No. 61/640,327, filed Apr. 30, 2012, is incorporated by reference in their entirety for all purposes.

What is claimed is:

1. An isolated polypeptide comprising a human immunoglobulin G class 1 (IgG$_1$) Fc domain, wherein the IgG$_1$ Fc domain comprises:
   (a) a Phenylalanine (F) amino acid at position 234;
   (b) a Glutamine (Q) at position 235; and,
   (c) a Glutamine (Q) amino acid at position 322,
wherein the amino acid numbering is according to the EU index as in Kabat.

2. The polypeptide of claim 1, further comprising a Glycine (G) amino acid at position 331, wherein the amino acid numbering is according to the EU index as in Kabat.

3. The polypeptide of claim 1, further comprising:
   (a) a Tyrosine (Y) amino acid at position 252, or a Serine (S) amino acid at position 252, or a Tryptophan (W) amino acid at position 252 or a Threonine (T) amino acid at position 252; and/or
   (b) a Threonine (T) amino acid at position 254; and/or
   (c) a Glutamic acid (E) amino acid at position 256, or a Serine (S) amino acid at position 256, or a Arginine (R) amino acid at position 256, or a Glutamine (Q) amino acid at position 256, or an Aspartate (D) amino acid at position 256,
wherein the amino acid numbering is according to the EU index as in Kabat.

4. The polypeptide of claim 1, further comprising:
   (a) a Tyrosine (Y) amino acid at position 252; and/or
   (b) a Threonine (T) amino acid at position 254; and/or
   (c) a Glutamic acid (E) amino acid at position 256,
wherein the amino acid numbering is according to the EU index as in Kabat.

5. The polypeptide of claim 1, further comprising:
   (a) a Tyrosine (Y)amino acid at position 252 or a Threonine (T) amino acid at position 252; and
   (b) a Threonine (T) amino acid at position 254,
wherein the amino acid numbering is according to the EU index as in Kabat.

6. The polypeptide of claim 1, further comprising:
   (a) a Threonine (T) amino acid at position 254; and
   (b) a Glutamic acid (E) amino acid at position 256, or a Serine (S) amino acid at position 256, or a Arginine (R) amino acid at position 256, or a Glutamine (Q) amino acid at position 256, or an Aspartate (D) amino acid at position 256,
wherein the amino acid numbering is according to the EU index as in Kabat.

7. The polypeptide of claim 1, further comprising:
   (a) a Tyrosine (Y) amino acid at position 252, or a Serine (S) amino acid at position 252, or a Tryptophan (W) amino acid at position 252 or a Threonine (T) amino acid at position 252; and
   (b) a Glutamic acid (E) amino acid at position 256, or a Serine (S) amino acid at position 256, or a Arginine (R) amino acid at position 256, or a Glutamine (Q) amino acid at position 256, or an Aspartate (D) amino acid at position 256,
wherein the amino acid numbering is according to the EU index as in Kabat.

8. The polypeptide of claim 1, further comprising:
   (a) a Tyrosine (Y) amino acid at position 252, and a Threonine (T) amino acid at position 254; or,
   (b) a Threonine (T) amino acid at position 254 and a Glutamic acid (E) amino acid at position 256; or,
   (c) a Tyrosine (Y) amino acid at position 252 and a Glutamic acid (E) amino acid at position 256
wherein the amino acid numbering is according to the EU index as in Kabat.

9. The polypeptide of claim 1, further comprising a Tyrosine (Y) amino acid at position 252, a Threonine (T) amino acid at position 254, and, a Glutamic acid (E) amino acid at position 256, wherein the amino acid numbering is according to the EU index as in Kabat.

10. The polypeptide of claim 1, comprising:
   (a) a Phenylalanine (F) amino acid at position 234;
   (b) a Glutamine (Q) amino acid at position 235;
   (c) a Glutamine (Q) amino acid at position 322;

(d) a Tyrosine (Y) amino acid at position 252;
(e) a Threonine (T) amino acid at position 254; and,
(f) a Glutamic acid (E) amino acid at position 256,
wherein the amino acid numbering is according to the EU index as in Kabat.

11. The polypeptide of claim 1, further comprising:
(a) a Glycine (G) amino acid at position 331;
(b) a Tyrosine (Y) amino acid at position 252;
(c) a Threonine (T) amino acid at position 254; and,
(d) a Glutamic acid (E) amino acid at position 256,
wherein the amino acid numbering is according to the EU index as in Kabat.

12. The polypeptide of claim 1, wherein the polypeptide has an improved pharmacokinetic (PK) property when compared to the same polypeptide comprising a wild-type $IgG_1$ Fc domain.

13. The polypeptide of claim 12, wherein the PK property is half-life.

14. The polypeptide of claim 1, wherein the polypeptide has improved FcRn binding when compared to the same polypeptide comprising a wild-type $IgG_1$ Fc domain.

15. The polypeptide of claim 1, wherein the polypeptide further comprises an antigen binding domain.

16. The polypeptide of claim 15, wherein the antigen-binding domain is derived from a monoclonal antibody or an antigen-binding fragment thereof.

17. The polypeptide of claim 15, wherein the antigen-binding domain is derived from a human antibody, a humanized antibody, or a chimeric antibody.

18. The polypeptide of claim 15, wherein the antigen-binding domain comprises:
(a) a single chain antibody;
(b) a diabody;
(c) a polypeptide chain of an antibody;
(d) an $F(ab')_2$ fragment; or,
(e) and F(ab) fragment.

19. The polypeptide of claim 1, wherein the polypeptide has reduced Fc-mediated effector function when compared to the same polypeptide comprising a wild-type $IgG_1$ Fc domain.

20. The polypeptide of claim 19, wherein the effector function is antibody-dependent cell-mediated cytotoxicity (ADCC).

21. The polypeptide of claim 19, wherein the effector function is complement-dependent cytotoxicity (CDC).

22. The polypeptide of claim 1, wherein the polypeptide has lower affinity for an Fc gamma receptor (FcγR) when compared to the same polypeptide comprising a wild-type $IgG_1$ Fc domain.

23. The polypeptide of claim 22, wherein the FcγR is a human FcγR.

24. The polypeptide of claim 22, wherein the FcγR is selected from the group consisting of FcγRI, FcγRII, and FcγRIII.

25. The polypeptide of claim 24, wherein the FcγRI is FcγRIa.

26. The polypeptide of claim 24, wherein the FcγRII is FcγRIIa or FcγRIIb.

27. The polypeptide of claim 24, wherein the FcγRIII is FcγRIII (158V) or FcγRIII (158F).

28. The polypeptide of claim 1, wherein the polypeptide binds with improved affinity to FcRn when compared to the same polypeptide comprising a wild-type $IgG_1$ Fc domain.

29. The polypeptide of claim 28, wherein the polypeptide has a higher affinity for FcRn at pH 6.0 than at pH 7.4.

30. The polypeptide of claim 1, wherein the polypeptide binds with reduced affinity to C1q when compared to the same polypeptide comprising a wild-type $IgG_1$ Fc domain.

31. The polypeptide of claim 1, wherein the polypeptide displays an increase in thermal stability when compared to the same polypeptide comprising a Phenylalanine-Glutamic acid-Serine (FES)-YTE $IgG_1$ Fc domain.

32. The polypeptide of claim 31, wherein thermal stability is measured by Differential Scanning Calorimetry (DSC).

33. The polypeptide of claim 32, wherein the increase in thermal stability is at least 4° C.

34. The polypeptide of claim 31, wherein thermal stability is measured by Differential Scanning Fluorimetry (DSF).

35. The polypeptide of claim 34, wherein the DSF fluorescent probe is Sypro Orange.

36. The polypeptide of claim 35, wherein the increase in thermal stability increases is at least 5° C.

37. The polypeptide of claim 1, wherein the polypeptide displays an increase in apparent solubility as measured using a polyethylene glycol (PEG) precipitation assay when compared to the same polypeptide comprising a Phenylalanine-Glutamic acid-Serine (FES)-YTE $IgG_1$ Fc domain.

38. The polypeptide of claim 1, wherein the polypeptide displays an increase in stability as measured using an accelerated stability assay when compared to the same polypeptide comprising a Phenylalanine-Glutamic acid-Serine (FES)-YTE $IgG_1$ Fc domain.

39. The polypeptide of claim 38, wherein the accelerated stability assay comprises: (i) incubation of the polypeptide for an extended time period, and (ii) incubation at high temperature.

40. The polypeptide of claim 39, wherein the accelerated stability assay is performed by incubation at a high concentration.

41. The polypeptide of claim 39, wherein the extended time period is at least one month.

42. The polypeptide of claim 40, wherein the high concentration is at least 25 mg/ml.

43. The polypeptide of claim 39, wherein the high temperature is at least 40° C.

44. The polypeptide of claim 38, wherein the accelerated stability assay is performed using High Performance Size Exclusion Chromatography (HPSEC) or Dynamic Light Scattering (DLS).

45. A composition comprising the polypeptide according to claim 1 and a carrier.

46. A conjugate comprising the polypeptide according to claim 1 and a therapeutic moiety.

47. A kit comprising the polypeptide according to claim 1, or the composition of claim 45.

* * * * *

```
SEQUENCE LISTING

<160> NUMBER OF SEQ ID NOS: 40

<210> SEQ ID NO 1
<211> LENGTH: 330
<212> TYPE: PRT
<213> ORGANISM: homo sapiens

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

```
Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 2
<211> LENGTH: 326
<212> TYPE: PRT
<213> ORGANISM: homo sapiens

<400> SEQUENCE: 2

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Pro Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
```

```
                      165                 170                 175
Ser Thr Phe Arg Val Val Ser Val Leu Thr Val Val His Gln Asp Trp
                180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 3
<211> LENGTH: 377
<212> TYPE: PRT
<213> ORGANISM: homo sapiens

<400> SEQUENCE: 3

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205
```

```
Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 4
<211> LENGTH: 327
<212> TYPE: PRT
<213> ORGANISM: homo sapiens

<400> SEQUENCE: 4

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asn His Lys Pro Ser Asn Thr Lys Val Asp Lys
                85                  90                  95

Lys Val Glu Pro Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205
```

```
Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 5
<211> LENGTH: 214
<212> TYPE: PRT
<213> ORGANISM: artificial
<220> FEATURE:
<223> OTHER INFORMATION: synthetic construct

<400> SEQUENCE: 5

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His Phe Trp Ser Thr Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 6
```

<211> LENGTH: 452
<212> TYPE: PRT
<213> ORGANISM: artificial
<220> FEATURE:
<223> OTHER INFORMATION: synthetic construct

<400> SEQUENCE: 6

```
Gln Val Gln Leu Gln Gln Pro Gly Ala Glu Leu Val Lys Pro Gly Ala
1               5                   10                  15

Ser Val Lys Met Ser Cys Lys Ala Ser Gly Phe Thr Phe Thr Asn Tyr
            20                  25                  30

Asn Met His Trp Leu Lys Gln Thr Pro Gly Gln Gly Leu Glu Trp Ile
        35                  40                  45

Gly Ala Ile Tyr Pro Glu Asn Gly Asp Thr Ser Tyr Asn Gln Lys Phe
    50                  55                  60

Lys Gly Lys Ala Thr Leu Thr Ala Asp Lys Ala Ser Ser Thr Ala Tyr
65                  70                  75                  80

Met His Leu Ser Ser Leu Thr Ser Glu Asp Ser Ala Val Tyr Phe Cys
                85                  90                  95

Ala Arg Phe Tyr Tyr Gly Ser Tyr Tyr Gly Ala Met Asp Tyr Trp
            100                 105                 110

Gly Gln Gly Thr Ser Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380
```

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
        450

<210> SEQ ID NO 7
<211> LENGTH: 215
<212> TYPE: PRT
<213> ORGANISM: artificial
<220> FEATURE:
<223> OTHER INFORMATION: synthetic construct

<400> SEQUENCE: 7

Gln Ser Ala Leu Thr Gln Pro Pro Ser Ala Ser Gly Thr Pro Gly Gln
1               5                   10                  15

Arg Val Thr Ile Ser Cys Ser Gly Thr Asn Ser Asn Ile Gly Ser Asn
            20                  25                  30

Tyr Val Phe Trp Tyr Gln Gln Leu Pro Gly Thr Ala Pro Lys Leu Leu
        35                  40                  45

Ile Phe Glu Ser Asn Arg Arg Pro Ser Gly Val Pro Asp Arg Phe Ser
50                  55                  60

Gly Ser Lys Ser Asp Thr Ser Ala Ser Leu Ala Ile Ser Gly Leu Arg
65                  70                  75                  80

Ser Glu Asp Glu Ala Asp Tyr Tyr Cys Ala Thr Trp Asp Asp Thr Leu
                85                  90                  95

Ile Ala Pro Val Phe Gly Ser Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Ala Glu Cys
    210                 215

<210> SEQ ID NO 8
<211> LENGTH: 450
<212> TYPE: PRT
<213> ORGANISM: artificial
<220> FEATURE:
<223> OTHER INFORMATION: synthetic construct

<400> SEQUENCE: 8

Glu Val Gln Leu Leu Glu Ser Gly Gly Gly Leu Val Gln Pro Gly Gly

```
1               5                   10                  15
Ser Leu Arg Leu Ser Cys Ala Ala Ser Gly Phe Thr Phe Ser Ser Tyr
            20                  25                  30

Val Met Asn Trp Val Arg Gln Ala Pro Gly Lys Gly Leu Glu Trp Val
            35                  40                  45

Ser Ser Ile Ser Pro Ser Gly Gly Arg Thr Trp Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Ser Asp Gly Ser Ala Ala Gly Phe Leu Gly Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
 130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
 210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
 290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
 370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430
```

-continued

Glu Ala Leu His Asn His Tyr Thr Gln Lys Ser Leu Ser Leu Ser Pro
            435                 440                 445

Gly Lys
    450

<210> SEQ ID NO 9
<211> LENGTH: 218
<212> TYPE: PRT
<213> ORGANISM: artificial
<220> FEATURE:
<223> OTHER INFORMATION: synthetic construct

<400> SEQUENCE: 9

Pro Ala Pro Glu Phe Gln Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu
    50                  55                  60

Glu Gln Tyr Asn Ser Thr Tyr Arg Val Val Ser Val Leu Thr Val Leu
65                  70                  75                  80

His Gln Asp Trp Leu Asn Gly Lys Glu Tyr Lys Cys Gln Val Ser Asn
                85                  90                  95

Lys Ala Leu Pro Ala Pro Ile Glu Lys Thr Ile Ser Lys Ala Lys Gly
            100                 105                 110

Gln Pro Arg Glu Pro Gln Val Tyr Thr Leu Pro Pro Ser Arg Asp Glu
        115                 120                 125

Leu Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215

<210> SEQ ID NO 10
<211> LENGTH: 218
<212> TYPE: PRT
<213> ORGANISM: artificial
<220> FEATURE:
<223> OTHER INFORMATION: synthetic construct

<400> SEQUENCE: 10

Pro Ala Pro Glu Phe Gln Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu

```
            50                  55                  60
Glu Gln Tyr Asn Ser Thr Tyr Arg Val Val Ser Val Leu Thr Val Leu
 65                  70                  75                  80

His Gln Asp Trp Leu Asn Gly Lys Glu Tyr Lys Cys Lys Val Ser Asn
                     85                  90                  95

Lys Ala Leu Pro Ala Gly Ile Glu Lys Thr Ile Ser Lys Ala Lys Gly
                100                 105                 110

Gln Pro Arg Glu Pro Gln Val Tyr Thr Leu Pro Pro Ser Arg Asp Glu
            115                 120                 125

Leu Thr Lys Asn Gln Val Ser Leu Thr Cys Leu Val Lys Gly Phe Tyr
        130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215

<210> SEQ ID NO 11
<211> LENGTH: 218
<212> TYPE: PRT
<213> ORGANISM: artificial
<220> FEATURE:
<223> OTHER INFORMATION: synthetic construct

<400> SEQUENCE: 11

Pro Ala Pro Glu Phe Ala Gly Gly Pro Ser Val Phe Leu Phe Pro Pro
  1               5                  10                  15

Lys Pro Lys Asp Thr Leu Met Ile Ser Arg Thr Pro Glu Val Thr Cys
                 20                  25                  30

Val Val Val Asp Val Ser His Glu Asp Pro Glu Val Lys Phe Asn Trp
             35                  40                  45

Tyr Val Asp Gly Val Glu Val His Asn Ala Lys Thr Lys Pro Arg Glu
         50                  55                  60

Glu Gln Tyr Asn Ser Thr Tyr Arg Val Val Ser Val Leu Thr Val Leu
 65                  70                  75                  80

His Gln Asp Trp Leu Asn Gly Lys Glu Tyr Lys Cys Gln Val Ser Asn
                     85                  90                  95

Lys Ala Leu Pro Ala Pro Ile Glu Lys Thr Ile Ser Lys Ala Lys Gly
                100                 105                 110

Gln Pro Arg Glu Pro Gln Val Tyr Thr Leu Pro Pro Ser Arg Asp Glu
            115                 120                 125

Leu Thr Lys Asn Gln Val Ser Leu Thr Cys Leu Val Lys Gly Phe Tyr
        130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
```

```
                    195                 200                 205
Gln Lys Ser Leu Ser Leu Ser Pro Gly Lys
    210                 215

<210> SEQ ID NO 12
<211> LENGTH: 218
<212> TYPE: PRT
<213> ORGANISM: artificial
<220> FEATURE:
<223> OTHER INFORMATION: synthetic construct

<400> SEQUENCE: 12

Pro Ala Pro Glu Phe Gln Gly Gly Pro Ser Val Phe Leu Phe Pro Pro
1               5                   10                  15

Lys Pro Lys Asp Thr Leu Tyr Ile Thr Arg Glu Pro Glu Val Thr Cys
            20                  25                  30

Val Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu
    50                  55                  60

Glu Gln Tyr Asn Ser Thr Tyr Arg Val Val Ser Val Leu Thr Val Leu
65                  70                  75                  80

His Gln Asp Trp Leu Asn Gly Lys Glu Tyr Lys Cys Gln Val Ser Asn
                85                  90                  95

Lys Ala Leu Pro Ala Pro Ile Glu Lys Thr Ile Ser Lys Ala Lys Gly
            100                 105                 110

Gln Pro Arg Glu Pro Gln Val Tyr Thr Leu Pro Pro Ser Arg Asp Glu
        115                 120                 125

Leu Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215

<210> SEQ ID NO 13
<211> LENGTH: 218
<212> TYPE: PRT
<213> ORGANISM: artificial
<220> FEATURE:
<223> OTHER INFORMATION: synthetic construct

<400> SEQUENCE: 13

Pro Ala Pro Glu Phe Gln Gly Gly Pro Ser Val Phe Leu Phe Pro Pro
1               5                   10                  15

Lys Pro Lys Asp Thr Leu Tyr Ile Thr Arg Glu Pro Glu Val Thr Cys
            20                  25                  30

Val Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu
    50                  55                  60
```

Glu Gln Tyr Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Ala Leu Pro Ala Gly Ile Glu Lys Thr Ile Ser Lys Ala Lys Gly
            100                 105                 110

Gln Pro Arg Glu Pro Gln Val Tyr Thr Leu Pro Pro Ser Arg Asp Glu
        115                 120                 125

Leu Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215

<210> SEQ ID NO 14
<211> LENGTH: 218
<212> TYPE: PRT
<213> ORGANISM: artificial
<220> FEATURE:
<223> OTHER INFORMATION: synthetic construct

<400> SEQUENCE: 14

Pro Ala Pro Glu Phe Ala Gly Gly Pro Ser Val Phe Leu Phe Pro Pro
1               5                   10                  15

Lys Pro Lys Asp Thr Leu Tyr Ile Thr Arg Glu Pro Glu Val Thr Cys
            20                  25                  30

Val Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu
    50                  55                  60

Glu Gln Tyr Asn Ser Thr Tyr Arg Val Val Ser Val Leu Thr Val Leu
65                  70                  75                  80

His Gln Asp Trp Leu Asn Gly Lys Glu Tyr Lys Cys Gln Val Ser Asn
                85                  90                  95

Lys Ala Leu Pro Ala Pro Ile Glu Lys Thr Ile Ser Lys Ala Lys Gly
            100                 105                 110

Gln Pro Arg Glu Pro Gln Val Tyr Thr Leu Pro Pro Ser Arg Asp Glu
        115                 120                 125

Leu Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

```
Gln Lys Ser Leu Ser Leu Ser Pro Gly Lys
    210                 215

<210> SEQ ID NO 15
<211> LENGTH: 217
<212> TYPE: PRT
<213> ORGANISM: artificial
<220> FEATURE:
<223> OTHER INFORMATION: synthetic construct

<400> SEQUENCE: 15

Pro Ala Pro Pro Phe Gln Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Phe Arg Val Val Ser Val Leu Thr Val Val His
65                  70                  75                  80

Gln Asp Trp Leu Asn Gly Lys Glu Tyr Lys Cys Gln Val Ser Asn Lys
                85                  90                  95

Gly Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ser Val Glu Trp Glu Ser Asn Gly Gln Pro Glu Asn Asn
145                 150                 155                 160

Tyr Lys Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 16
<211> LENGTH: 217
<212> TYPE: PRT
<213> ORGANISM: artificial
<220> FEATURE:
<223> OTHER INFORMATION: synthetic construct

<400> SEQUENCE: 16

Pro Ala Pro Pro Phe Gln Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Phe Arg Val Val Ser Val Leu Thr Val Val His
65                  70                  75                  80
```

Gln Asp Trp Leu Asn Gly Lys Glu Tyr Lys Cys Lys Val Ser Asn Lys
            85                  90                  95

Gly Leu Pro Ala Gly Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
            115                 120                 125

Thr Lys Asn Gln Val Ser Leu Thr Cys Leu Val Lys Gly Phe Tyr Pro
    130                 135                 140

Ser Asp Ile Ser Val Glu Trp Glu Ser Asn Gly Gln Pro Glu Asn Asn
145                 150                 155                 160

Tyr Lys Thr Thr Pro Pro Met Leu Asp Ser Asp Gly Ser Phe Phe Leu
            165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
    210                 215

<210> SEQ ID NO 17
<211> LENGTH: 217
<212> TYPE: PRT
<213> ORGANISM: artificial
<220> FEATURE:
<223> OTHER INFORMATION: synthetic construct

<400> SEQUENCE: 17

Pro Ala Pro Pro Phe Ala Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Asn Trp Tyr
        35                  40                  45

Val Asp Gly Val Glu Val His Asn Ala Lys Thr Lys Pro Arg Glu Glu
50                  55                  60

Gln Phe Asn Ser Thr Phe Arg Val Val Ser Val Leu Thr Val Val His
65                  70                  75                  80

Gln Asp Trp Leu Asn Gly Lys Glu Tyr Lys Cys Gln Val Ser Asn Lys
            85                  90                  95

Gly Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
            115                 120                 125

Thr Lys Asn Gln Val Ser Leu Thr Cys Leu Val Lys Gly Phe Tyr Pro
    130                 135                 140

Ser Asp Ile Ser Val Glu Trp Glu Ser Asn Gly Gln Pro Glu Asn Asn
145                 150                 155                 160

Tyr Lys Thr Thr Pro Pro Met Leu Asp Ser Asp Gly Ser Phe Phe Leu
            165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
    210                 215

<210> SEQ ID NO 18
<211> LENGTH: 217
<212> TYPE: PRT
<213> ORGANISM: artificial
<220> FEATURE:
<223> OTHER INFORMATION: synthetic construct

<400> SEQUENCE: 18

Pro Ala Pro Pro Phe Gln Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Phe Arg Val Val Ser Val Leu Thr Val Val His
65                  70                  75                  80

Gln Asp Trp Leu Asn Gly Lys Glu Tyr Lys Cys Gln Val Ser Asn Lys
                85                  90                  95

Gly Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ser Val Glu Trp Glu Ser Asn Gly Gln Pro Glu Asn Asn
145                 150                 155                 160

Tyr Lys Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 19
<211> LENGTH: 217
<212> TYPE: PRT
<213> ORGANISM: artificial
<220> FEATURE:
<223> OTHER INFORMATION: synthetic construct

<400> SEQUENCE: 19

Pro Ala Pro Pro Phe Gln Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Phe Arg Val Val Ser Val Leu Thr Val Val His
65                  70                  75                  80

Gln Asp Trp Leu Asn Gly Lys Glu Tyr Lys Cys Lys Val Ser Asn Lys

```
                    85                  90                  95
Gly Leu Pro Ala Gly Ile Glu Lys Thr Ile Ser Lys Thr Lys Gly Gln
            100                 105                 110
Pro Arg Glu Pro Gln Val Tyr Thr Leu Pro Pro Ser Arg Glu Glu Met
            115                 120                 125
Thr Lys Asn Gln Val Ser Leu Thr Cys Leu Val Lys Gly Phe Tyr Pro
    130                 135                 140
Ser Asp Ile Ser Val Glu Trp Glu Ser Asn Gly Gln Pro Glu Asn Asn
145                 150                 155                 160
Tyr Lys Thr Thr Pro Pro Met Leu Asp Ser Asp Gly Ser Phe Phe Leu
                165                 170                 175
Tyr Ser Lys Leu Thr Val Asp Lys Ser Arg Trp Gln Gln Gly Asn Val
            180                 185                 190
Phe Ser Cys Ser Val Met His Glu Ala Leu His Asn His Tyr Thr Gln
            195                 200                 205
Lys Ser Leu Ser Leu Ser Pro Gly Lys
    210                 215

<210> SEQ ID NO 20
<211> LENGTH: 217
<212> TYPE: PRT
<213> ORGANISM: artificial
<220> FEATURE:
<223> OTHER INFORMATION: synthetic construct

<400> SEQUENCE: 20

Pro Ala Pro Pro Phe Ala Gly Pro Ser Val Phe Leu Phe Pro Pro Lys
1               5                   10                  15
Pro Lys Asp Thr Leu Tyr Ile Thr Arg Glu Pro Glu Val Thr Cys Val
            20                  25                  30
Val Val Asp Val Ser His Glu Asp Pro Glu Val Gln Phe Asn Trp Tyr
        35                  40                  45
Val Asp Gly Val Glu Val His Asn Ala Lys Thr Lys Pro Arg Glu Glu
    50                  55                  60
Gln Phe Asn Ser Thr Phe Arg Val Val Ser Val Leu Thr Val Val His
65                  70                  75                  80
Gln Asp Trp Leu Asn Gly Lys Glu Tyr Lys Cys Gln Val Ser Asn Lys
                85                  90                  95
Gly Leu Pro Ala Pro Ile Glu Lys Thr Ile Ser Lys Thr Lys Gly Gln
            100                 105                 110
Pro Arg Glu Pro Gln Val Tyr Thr Leu Pro Pro Ser Arg Glu Glu Met
            115                 120                 125
Thr Lys Asn Gln Val Ser Leu Thr Cys Leu Val Lys Gly Phe Tyr Pro
    130                 135                 140
Ser Asp Ile Ser Val Glu Trp Glu Ser Asn Gly Gln Pro Glu Asn Asn
145                 150                 155                 160
Tyr Lys Thr Thr Pro Pro Met Leu Asp Ser Asp Gly Ser Phe Phe Leu
                165                 170                 175
Tyr Ser Lys Leu Thr Val Asp Lys Ser Arg Trp Gln Gln Gly Asn Val
            180                 185                 190
Phe Ser Cys Ser Val Met His Glu Ala Leu His Asn His Tyr Thr Gln
            195                 200                 205
Lys Ser Leu Ser Leu Ser Pro Gly Lys
    210                 215
```

```
<210> SEQ ID NO 21
<211> LENGTH: 218
<212> TYPE: PRT
<213> ORGANISM: artificial
<220> FEATURE:
<223> OTHER INFORMATION: synthetic construct

<400> SEQUENCE: 21

Pro Ala Pro Glu Phe Gln Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Gln Phe Lys Trp
        35                  40                  45

Tyr Val Asp Gly Val Glu Val His Asn Ala Lys Thr Lys Pro Arg Glu
    50                  55                  60

Glu Gln Tyr Asn Ser Thr Phe Arg Val Val Ser Val Leu Thr Val Leu
65                  70                  75                  80

His Gln Asp Trp Leu Asn Gly Lys Glu Tyr Lys Cys Gln Val Ser Asn
                85                  90                  95

Lys Ala Leu Pro Ala Pro Ile Glu Lys Thr Ile Ser Lys Thr Lys Gly
            100                 105                 110

Gln Pro Arg Glu Pro Gln Val Tyr Thr Leu Pro Pro Ser Arg Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Ser Gly Gln Pro Glu Asn
145                 150                 155                 160

Asn Tyr Asn Thr Thr Pro Pro Met Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Ile Phe Ser Cys Ser Val Met His Glu Ala Leu His Asn Arg Phe Thr
        195                 200                 205

Gln Lys Ser Leu Ser Leu Ser Pro Gly Lys
    210                 215

<210> SEQ ID NO 22
<211> LENGTH: 218
<212> TYPE: PRT
<213> ORGANISM: artificial
<220> FEATURE:
<223> OTHER INFORMATION: synthetic construct

<400> SEQUENCE: 22

Pro Ala Pro Glu Phe Gln Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Gln Phe Lys Trp
        35                  40                  45

Tyr Val Asp Gly Val Glu Val His Asn Ala Lys Thr Lys Pro Arg Glu
    50                  55                  60

Glu Gln Tyr Asn Ser Thr Phe Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95
```

```
Lys Ala Leu Pro Ala Gly Ile Glu Lys Thr Ile Ser Lys Thr Lys Gly
            100                 105                 110

Gln Pro Arg Glu Pro Gln Val Tyr Thr Leu Pro Pro Ser Arg Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Ser Gly Gln Pro Glu Asn
145                 150                 155                 160

Asn Tyr Asn Thr Thr Pro Pro Met Leu Asp Ser Asp Gly Ser Phe Phe
                165                 170                 175

Leu Tyr Ser Lys Leu Thr Val Asp Lys Ser Arg Trp Gln Gln Gly Asn
                180                 185                 190

Ile Phe Ser Cys Ser Val Met His Glu Ala Leu His Asn Arg Phe Thr
                195                 200                 205

Gln Lys Ser Leu Ser Leu Ser Pro Gly Lys
        210                 215
```

<210> SEQ ID NO 23
<211> LENGTH: 218
<212> TYPE: PRT
<213> ORGANISM: artificial
<220> FEATURE:
<223> OTHER INFORMATION: synthetic construct

<400> SEQUENCE: 23

```
Pro Ala Pro Glu Phe Ala Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Gln Phe Lys Trp
        35                  40                  45

Tyr Val Asp Gly Val Glu Val His Asn Ala Lys Thr Lys Pro Arg Glu
    50                  55                  60

Glu Gln Tyr Asn Ser Thr Phe Arg Val Val Ser Val Leu Thr Val Leu
65                  70                  75                  80

His Gln Asp Trp Leu Asn Gly Lys Glu Tyr Lys Cys Gln Val Ser Asn
                85                  90                  95

Lys Ala Leu Pro Ala Pro Ile Glu Lys Thr Ile Ser Lys Thr Lys Gly
            100                 105                 110

Gln Pro Arg Glu Pro Gln Val Tyr Thr Leu Pro Pro Ser Arg Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Ser Gly Gln Pro Glu Asn
145                 150                 155                 160

Asn Tyr Asn Thr Thr Pro Pro Met Leu Asp Ser Asp Gly Ser Phe Phe
                165                 170                 175

Leu Tyr Ser Lys Leu Thr Val Asp Lys Ser Arg Trp Gln Gln Gly Asn
                180                 185                 190

Ile Phe Ser Cys Ser Val Met His Glu Ala Leu His Asn Arg Phe Thr
                195                 200                 205

Gln Lys Ser Leu Ser Leu Ser Pro Gly Lys
        210                 215
```

<210> SEQ ID NO 24
<211> LENGTH: 218

```
<212> TYPE: PRT
<213> ORGANISM: artificial
<220> FEATURE:
<223> OTHER INFORMATION: synthetic construct

<400> SEQUENCE: 24

Pro Ala Pro Glu Phe Gln Gly Gly Pro Ser Val Phe Leu Phe Pro Pro
1               5                   10                  15

Lys Pro Lys Asp Thr Leu Tyr Ile Thr Arg Glu Pro Glu Val Thr Cys
            20                  25                  30

Val Val Val Asp Val Ser His Glu Asp Pro Glu Val Gln Phe Lys Trp
        35                  40                  45

Tyr Val Asp Gly Val Glu Val His Asn Ala Lys Thr Lys Pro Arg Glu
    50                  55                  60

Glu Gln Tyr Asn Ser Thr Phe Arg Val Val Ser Val Leu Thr Val Leu
65                  70                  75                  80

His Gln Asp Trp Leu Asn Gly Lys Glu Tyr Lys Cys Gln Val Ser Asn
                85                  90                  95

Lys Ala Leu Pro Ala Pro Ile Glu Lys Thr Ile Ser Lys Thr Lys Gly
            100                 105                 110

Gln Pro Arg Glu Pro Gln Val Tyr Thr Leu Pro Pro Ser Arg Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Ser Gly Gln Pro Glu Asn
145                 150                 155                 160

Asn Tyr Asn Thr Thr Pro Pro Met Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Ile Phe Ser Cys Ser Val Met His Glu Ala Leu His Asn Arg Phe Thr
        195                 200                 205

Gln Lys Ser Leu Ser Leu Ser Pro Gly Lys
    210                 215

<210> SEQ ID NO 25
<211> LENGTH: 218
<212> TYPE: PRT
<213> ORGANISM: artificial
<220> FEATURE:
<223> OTHER INFORMATION: synthetic construct

<400> SEQUENCE: 25

Pro Ala Pro Glu Phe Gln Gly Gly Pro Ser Val Phe Leu Phe Pro Pro
1               5                   10                  15

Lys Pro Lys Asp Thr Leu Tyr Ile Thr Arg Glu Pro Glu Val Thr Cys
            20                  25                  30

Val Val Val Asp Val Ser His Glu Asp Pro Glu Val Gln Phe Lys Trp
        35                  40                  45

Tyr Val Asp Gly Val Glu Val His Asn Ala Lys Thr Lys Pro Arg Glu
    50                  55                  60

Glu Gln Tyr Asn Ser Thr Phe Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Ala Leu Pro Ala Gly Ile Glu Lys Thr Ile Ser Lys Thr Lys Gly
            100                 105                 110
```

```
Gln Pro Arg Glu Pro Gln Val Tyr Thr Leu Pro Pro Ser Arg Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Ser Gly Gln Pro Glu Asn
145                 150                 155                 160

Asn Tyr Asn Thr Thr Pro Pro Met Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Ile Phe Ser Cys Ser Val Met His Glu Ala Leu His Asn Arg Phe Thr
        195                 200                 205

Gln Lys Ser Leu Ser Leu Ser Pro Gly Lys
    210                 215

<210> SEQ ID NO 26
<211> LENGTH: 218
<212> TYPE: PRT
<213> ORGANISM: artificial
<220> FEATURE:
<223> OTHER INFORMATION: synthetic construct

<400> SEQUENCE: 26

Pro Ala Pro Glu Phe Ala Gly Gly Pro Ser Val Phe Leu Phe Pro Pro
1               5                   10                  15

Lys Pro Lys Asp Thr Leu Tyr Ile Thr Arg Glu Pro Glu Val Thr Cys
            20                  25                  30

Val Val Val Asp Val Ser His Glu Asp Pro Glu Val Gln Phe Lys Trp
        35                  40                  45

Tyr Val Asp Gly Val Glu Val His Asn Ala Lys Thr Lys Pro Arg Glu
    50                  55                  60

Glu Gln Tyr Asn Ser Thr Phe Arg Val Val Ser Val Leu Thr Val Leu
65                  70                  75                  80

His Gln Asp Trp Leu Asn Gly Lys Glu Tyr Lys Cys Gln Val Ser Asn
                85                  90                  95

Lys Ala Leu Pro Ala Pro Ile Glu Lys Thr Ile Ser Lys Thr Lys Gly
            100                 105                 110

Gln Pro Arg Glu Pro Gln Val Tyr Thr Leu Pro Pro Ser Arg Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Ser Gly Gln Pro Glu Asn
145                 150                 155                 160

Asn Tyr Asn Thr Thr Pro Pro Met Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Ile Phe Ser Cys Ser Val Met His Glu Ala Leu His Asn Arg Phe Thr
        195                 200                 205

Gln Lys Ser Leu Ser Leu Ser Pro Gly Lys
    210                 215

<210> SEQ ID NO 27
<211> LENGTH: 218
<212> TYPE: PRT
<213> ORGANISM: artificial
```

<220> FEATURE:
<223> OTHER INFORMATION: synthetic construct

<400> SEQUENCE: 27

Pro Ala Pro Glu Phe Gln Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser Gln Glu Asp Pro Glu Val Gln Phe Asn Trp
        35                  40                  45

Tyr Val Asp Gly Val Glu Val His Asn Ala Lys Thr Lys Pro Arg Glu
    50                  55                  60

Glu Gln Phe Asn Ser Thr Tyr Arg Val Val Ser Val Leu Thr Val Leu
65                  70                  75                  80

His Gln Asp Trp Leu Asn Gly Lys Glu Tyr Lys Cys Gln Val Ser Asn
                85                  90                  95

Lys Gly Leu Pro Ser Ser Ile Glu Lys Thr Ile Ser Lys Ala Lys Gly
            100                 105                 110

Gln Pro Arg Glu Pro Gln Val Tyr Thr Leu Pro Pro Ser Gln Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Arg Leu Thr Val Asp Lys Ser Arg Trp Gln Glu Gly Asn
            180                 185                 190

Val Phe Ser Cys Ser Val Met His Glu Ala Leu His Asn His Tyr Thr
        195                 200                 205

Gln Lys Ser Leu Ser Leu Ser Leu Gly Lys
    210                 215

<210> SEQ ID NO 28
<211> LENGTH: 218
<212> TYPE: PRT
<213> ORGANISM: artificial
<220> FEATURE:
<223> OTHER INFORMATION: synthetic construct

<400> SEQUENCE: 28

Pro Ala Pro Glu Phe Gln Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser Gln Glu Asp Pro Glu Val Gln Phe Asn Trp
        35                  40                  45

Tyr Val Asp Gly Val Glu Val His Asn Ala Lys Thr Lys Pro Arg Glu
    50                  55                  60

Glu Gln Phe Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Gly Leu Pro Ser Gly Ile Glu Lys Thr Ile Ser Lys Ala Lys Gly
            100                 105                 110

Gln Pro Arg Glu Pro Gln Val Tyr Thr Leu Pro Pro Ser Gln Glu Glu

```
                115                 120                 125
Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Arg Leu Thr Val Asp Lys Ser Arg Trp Gln Glu Gly Asn
                180                 185                 190

Val Phe Ser Cys Ser Val Met His Glu Ala Leu His Asn His Tyr Thr
                195                 200                 205

Gln Lys Ser Leu Ser Leu Ser Leu Gly Lys
    210                 215

<210> SEQ ID NO 29
<211> LENGTH: 218
<212> TYPE: PRT
<213> ORGANISM: artificial
<220> FEATURE:
<223> OTHER INFORMATION: synthetic construct

<400> SEQUENCE: 29

Pro Ala Pro Glu Phe Ala Gly Gly Pro Ser Val Phe Leu Phe Pro Pro
1               5                   10                  15

Lys Pro Lys Asp Thr Leu Met Ile Ser Arg Thr Pro Glu Val Thr Cys
                20                  25                  30

Val Val Val Asp Val Ser Gln Glu Asp Pro Glu Val Gln Phe Asn Trp
            35                  40                  45

Tyr Val Asp Gly Val Glu Val His Asn Ala Lys Thr Lys Pro Arg Glu
    50                  55                  60

Glu Gln Phe Asn Ser Thr Tyr Arg Val Val Ser Val Leu Thr Val Leu
65                  70                  75                  80

His Gln Asp Trp Leu Asn Gly Lys Glu Tyr Lys Cys Gln Val Ser Asn
                85                  90                  95

Lys Gly Leu Pro Ser Ser Ile Glu Lys Thr Ile Ser Lys Ala Lys Gly
                100                 105                 110

Gln Pro Arg Glu Pro Gln Val Tyr Thr Leu Pro Pro Ser Gln Glu Glu
            115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Arg Leu Thr Val Asp Lys Ser Arg Trp Gln Glu Gly Asn
                180                 185                 190

Val Phe Ser Cys Ser Val Met His Glu Ala Leu His Asn His Tyr Thr
                195                 200                 205

Gln Lys Ser Leu Ser Leu Ser Leu Gly Lys
    210                 215

<210> SEQ ID NO 30
<211> LENGTH: 218
<212> TYPE: PRT
<213> ORGANISM: artificial
<220> FEATURE:
<223> OTHER INFORMATION: synthetic construct
```

<400> SEQUENCE: 30

Pro Ala Pro Glu Phe Gln Gly Gly Pro Ser Val Phe Leu Phe Pro Pro
1               5                   10                  15

Lys Pro Lys Asp Thr Leu Tyr Ile Thr Arg Glu Pro Glu Val Thr Cys
            20                  25                  30

Val Val Val Asp Val Ser Gln Glu Asp Pro Glu Val Gln Phe Asn Trp
        35                  40                  45

Tyr Val Asp Gly Val Glu Val His Asn Ala Lys Thr Lys Pro Arg Glu
    50                  55                  60

Glu Gln Phe Asn Ser Thr Tyr Arg Val Val Ser Val Leu Thr Val Leu
65                  70                  75                  80

His Gln Asp Trp Leu Asn Gly Lys Glu Tyr Lys Cys Gln Val Ser Asn
                85                  90                  95

Lys Gly Leu Pro Ser Ser Ile Glu Lys Thr Ile Ser Lys Ala Lys Gly
            100                 105                 110

Gln Pro Arg Glu Pro Gln Val Tyr Thr Leu Pro Pro Ser Gln Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Arg Leu Thr Val Asp Lys Ser Arg Trp Gln Glu Gly Asn
            180                 185                 190

Val Phe Ser Cys Ser Val Met His Glu Ala Leu His Asn His Tyr Thr
        195                 200                 205

Gln Lys Ser Leu Ser Leu Ser Leu Gly Lys
    210                 215

<210> SEQ ID NO 31
<211> LENGTH: 218
<212> TYPE: PRT
<213> ORGANISM: artificial
<220> FEATURE:
<223> OTHER INFORMATION: synthetic construct

<400> SEQUENCE: 31

Pro Ala Pro Glu Phe Gln Gly Gly Pro Ser Val Phe Leu Phe Pro Pro
1               5                   10                  15

Lys Pro Lys Asp Thr Leu Tyr Ile Thr Arg Glu Pro Glu Val Thr Cys
            20                  25                  30

Val Val Val Asp Val Ser Gln Glu Asp Pro Glu Val Gln Phe Asn Trp
        35                  40                  45

Tyr Val Asp Gly Val Glu Val His Asn Ala Lys Thr Lys Pro Arg Glu
    50                  55                  60

Glu Gln Phe Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Gly Leu Pro Ser Gly Ile Glu Lys Thr Ile Ser Lys Ala Lys Gly
            100                 105                 110

Gln Pro Arg Glu Pro Gln Val Tyr Thr Leu Pro Pro Ser Gln Glu Glu
        115                 120                 125

Met Thr Lys Asn Gln Val Ser Leu Thr Cys Leu Val Lys Gly Phe Tyr
            130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Arg Leu Thr Val Asp Lys Ser Arg Trp Gln Glu Gly Asn
            180                 185                 190

Val Phe Ser Cys Ser Val Met His Glu Ala Leu His Asn His Tyr Thr
            195                 200                 205

Gln Lys Ser Leu Ser Leu Ser Leu Gly Lys
            210                 215

<210> SEQ ID NO 32
<211> LENGTH: 218
<212> TYPE: PRT
<213> ORGANISM: artificial
<220> FEATURE:
<223> OTHER INFORMATION: synthetic construct

<400> SEQUENCE: 32

Pro Ala Pro Glu Phe Ala Gly Gly Pro Ser Val Phe Leu Phe Pro Pro
1               5                   10                  15

Lys Pro Lys Asp Thr Leu Tyr Ile Thr Arg Glu Pro Glu Val Thr Cys
            20                  25                  30

Val Val Val Asp Val Ser Gln Glu Asp Pro Glu Val Gln Phe Asn Trp
        35                  40                  45

Tyr Val Asp Gly Val Glu Val His Asn Ala Lys Thr Lys Pro Arg Glu
    50                  55                  60

Glu Gln Phe Asn Ser Thr Tyr Arg Val Val Ser Val Leu Thr Val Leu
65                  70                  75                  80

His Gln Asp Trp Leu Asn Gly Lys Glu Tyr Lys Cys Gln Val Ser Asn
            85                  90                  95

Lys Gly Leu Pro Ser Ser Ile Glu Lys Thr Ile Ser Lys Ala Lys Gly
            100                 105                 110

Gln Pro Arg Glu Pro Gln Val Tyr Thr Leu Pro Pro Ser Gln Glu Glu
        115                 120                 125

Met Thr Lys Asn Gln Val Ser Leu Thr Cys Leu Val Lys Gly Phe Tyr
            130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Arg Leu Thr Val Asp Lys Ser Arg Trp Gln Glu Gly Asn
            180                 185                 190

Val Phe Ser Cys Ser Val Met His Glu Ala Leu His Asn His Tyr Thr
            195                 200                 205

Gln Lys Ser Leu Ser Leu Ser Leu Gly Lys
            210                 215

<210> SEQ ID NO 33
<211> LENGTH: 450
<212> TYPE: PRT
<213> ORGANISM: artificial
<220> FEATURE:
<223> OTHER INFORMATION: synthetic construct

<400> SEQUENCE: 33

-continued

```
Gln Val Thr Leu Arg Glu Ser Gly Pro Ala Leu Val Lys Pro Thr Gln
1               5                  10                 15

Thr Leu Thr Leu Thr Cys Thr Phe Ser Gly Phe Ser Leu Ser Thr Pro
                20                 25                 30

Gly Met Ser Val Gly Trp Ile Arg Gln Pro Pro Gly Lys Ala Leu Glu
        35                  40                 45

Trp Leu Ala Asp Ile Trp Trp Asp Asp Lys Lys His Tyr Asn Pro Ser
    50                  55                 60

Leu Lys Asp Arg Leu Thr Ile Ser Lys Asp Thr Ser Lys Asn Gln Val
65                  70                 75                 80

Val Leu Lys Val Thr Asn Met Asp Pro Ala Asp Thr Ala Thr Tyr Tyr
                85                 90                 95

Cys Ala Arg Ala Met Ile Phe Asn Phe Tyr Phe Asp Val Trp Gly Gln
            100                105                110

Gly Thr Thr Val Thr Val Ser Ser Ala Ser Thr Lys Gly Pro Ser Val
            115                120                125

Phe Pro Leu Ala Pro Ser Ser Lys Ser Thr Ser Gly Gly Thr Ala Ala
    130                135                140

Leu Gly Cys Leu Val Lys Asp Tyr Phe Pro Glu Pro Val Thr Val Ser
145                 150                155                160

Trp Asn Ser Gly Ala Leu Thr Ser Gly Val His Thr Phe Pro Ala Val
                165                170                175

Leu Gln Ser Ser Gly Leu Tyr Ser Leu Ser Ser Val Val Thr Val Pro
            180                185                190

Ser Ser Ser Leu Gly Thr Gln Thr Tyr Ile Cys Asn Val Asn His Lys
            195                200                205

Pro Ser Asn Thr Lys Val Asp Lys Arg Val Glu Pro Lys Ser Cys Asp
210                 215                220

Lys Thr His Thr Cys Pro Pro Cys Pro Ala Pro Glu Leu Leu Gly Gly
225                 230                235                240

Pro Ser Val Phe Leu Phe Pro Pro Lys Pro Lys Asp Thr Leu Tyr Ile
                245                250                255

Thr Arg Glu Pro Glu Val Thr Cys Val Val Val Asp Val Ser His Glu
            260                265                270

Asp Pro Glu Val Lys Phe Asn Trp Tyr Val Asp Gly Val Glu Val His
            275                280                285

Asn Ala Lys Thr Lys Pro Arg Glu Glu Gln Tyr Asn Ser Thr Tyr Arg
    290                295                300

Val Val Ser Val Leu Thr Val Leu His Gln Asp Trp Leu Asn Gly Lys
305                 310                315                320

Glu Tyr Lys Cys Lys Val Ser Asn Lys Ala Leu Pro Ala Pro Ile Glu
                325                330                335

Lys Thr Ile Ser Lys Ala Lys Gly Gln Pro Arg Glu Pro Gln Val Tyr
            340                345                350

Thr Leu Pro Pro Ser Arg Glu Glu Met Thr Lys Asn Gln Val Ser Leu
            355                360                365

Thr Cys Leu Val Lys Gly Phe Tyr Pro Ser Asp Ile Ala Val Glu Trp
    370                375                380

Glu Ser Asn Gly Gln Pro Glu Asn Asn Tyr Lys Thr Pro Pro Val
385                 390                395                400

Leu Asp Ser Asp Gly Ser Phe Phe Leu Tyr Ser Lys Leu Thr Val Asp
                405                410                415
```

-continued

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 34
<211> LENGTH: 214
<212> TYPE: PRT
<213> ORGANISM: artificial
<220> FEATURE:
<223> OTHER INFORMATION: synthetic construct

<400> SEQUENCE: 34

Asp Ile Gln Met Thr Gln Ser Pro Ser Ser Leu Ser Ala Ser Val Gly
1               5                   10                  15

Asp Arg Val Thr Val Thr Cys Arg Ala Ser Gln Arg Ile Ser Thr Tyr
            20                  25                  30

Leu Asn Trp Tyr Gln Gln Lys Pro Gly Lys Ala Pro Lys Leu Leu Ile
        35                  40                  45

Ser Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Glu Ser Tyr Asn Thr Pro Arg
                85                  90                  95

Thr Phe Gly Gln Gly Thr Lys Val Glu Ile Arg Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 35
<211> LENGTH: 443
<212> TYPE: PRT
<213> ORGANISM: artificial
<220> FEATURE:
<223> OTHER INFORMATION: synthetic construct

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Tyr
            20                  25                  30

Tyr Met His Trp Val Arg Gln Ala Pro Gly Gln Gly Leu Glu Trp Met
        35                  40                  45
```

Gly Ile Ile Asn Pro Arg Gly Ser Thr Ser Tyr Ala Gln Lys Phe
        50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Ala Arg Gly Lys Tyr Trp Met Tyr Asp Trp Gly Lys Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
        435                 440

<210> SEQ ID NO 36
<211> LENGTH: 217

<212> TYPE: PRT
<213> ORGANISM: artificial
<220> FEATURE:
<223> OTHER INFORMATION: synthetic construct

<400> SEQUENCE: 36

Gln Ser Val Leu Thr Gln Pro Pro Ser Val Ser Ala Ala Pro Gly Gln
1               5                   10                  15

Lys Val Thr Ile Ser Cys Ser Gly Gly Ser Ser Ile Gly Asn Ser
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Thr Ser Pro
                85                  90                  95

Val Trp Glu Trp Pro Phe Gly Thr Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
210                 215

<210> SEQ ID NO 37
<211> LENGTH: 218
<212> TYPE: PRT
<213> ORGANISM: artificial
<220> FEATURE:
<223> OTHER INFORMATION: synthetic construct
<220> FEATURE:
<221> NAME/KEY: MISC_FEATURE
<222> LOCATION: (5)..(5)
<223> OTHER INFORMATION: Xaa is Leu or Phe
<220> FEATURE:
<221> NAME/KEY: MISC_FEATURE
<222> LOCATION: (6)..(6)
<223> OTHER INFORMATION: Xaa is selected from Leu, Ala, Asn, Phe, Gln
    and Val
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: MISC_FEATURE
<222> LOCATION: (25)..(25)
<223> OTHER INFORMATION: Xaa is Met or Tyr
<220> FEATURE:
<221> NAME/KEY: MISC_FEATURE
<222> LOCATION: (27)..(27)
<223> OTHER INFORMATION: Xaa is Ser or Thr
<220> FEATURE:
<221> NAME/KEY: MISC_FEATURE
<222> LOCATION: (29)..(29)
<223> OTHER INFORMATION: Xaa is Thr or Glu
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid
<220> FEATURE:
<221> NAME/KEY: MISC_FEATURE
<222> LOCATION: (112)..(112)
<223> OTHER INFORMATION: Xaa is selected from Lys, Ala, Asp, Glu, His, Asn and Gln
<220> FEATURE:
<221> NAME/KEY: MISC_FEATURE
<222> LOCATION: (122)..(122)
<223> OTHER INFORMATION: Xaa is selected from Pro, Ala and Gly

<400> SEQUENCE: 37

Pro Ala Pro Glu Xaa Xaa Gly Gly Pro Ser Val Phe Leu Phe Pro Pro
1               5                  10                  15

Lys Pro Lys Asp Thr Leu Xaa Ile Xaa Arg Xaa Pro Glu Val Thr Cys
            20                  25                  30

Val Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu
    50                  55                  60

Glu Gln Tyr Asn Ser Thr Tyr Arg Val Val Ser Val Leu Thr Val Leu
65                  70                  75                  80

His Gln Asp Trp Leu Asn Gly Lys Glu Tyr Lys Cys Xaa Val Ser Asn
                85                  90                  95

Lys Ala Leu Pro Ala Xaa Ile Glu Lys Thr Ile Ser Lys Ala Lys Gly
            100                 105                 110

Gln Pro Arg Glu Pro Gln Val Tyr Thr Leu Pro Pro Ser Arg Asp Glu
        115                 120                 125

Leu Thr Lys Asn Gln Val Ser Leu Thr Cys Leu Val Lys Gly Phe Tyr
130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215

<210> SEQ ID NO 38
<211> LENGTH: 217
<212> TYPE: PRT
<213> ORGANISM: artificial
<220> FEATURE:
<223> OTHER INFORMATION: synthetic construct
<220> FEATURE:
<221> NAME/KEY: MISC_FEATURE
<222> LOCATION: (5)..(5)
<223> OTHER INFORMATION: Xaa is Val or Phe
<220> FEATURE:
<221> NAME/KEY: MISC_FEATURE
<222> LOCATION: (6)..(6)
<223> OTHER INFORMATION: Xaa is selected from Ala, Asn, Phe, Gln and Val

```
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: MISC_FEATURE
<222> LOCATION: (24)..(24)
<223> OTHER INFORMATION: Xaa is Met or Tyr
<220> FEATURE:
<221> NAME/KEY: MISC_FEATURE
<222> LOCATION: (26)..(26)
<223> OTHER INFORMATION: Xaa is Ser or Thr
<220> FEATURE:
<221> NAME/KEY: MISC_FEATURE
<222> LOCATION: (28)..(28)
<223> OTHER INFORMATION: Xaa is Thr  or Glu
<220> FEATURE:
<221> NAME/KEY: misc_feature
<222> LOCATION: (92)..(92)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid
<220> FEATURE:
<221> NAME/KEY: MISC_FEATURE
<222> LOCATION: (111)..(112)
<223> OTHER INFORMATION: Xaa is selected from Lys, Ala, Asp, Glu, His,
    Asn and Gln
<220> FEATURE:
<221> NAME/KEY: MISC_FEATURE
<222> LOCATION: (121)..(121)
<223> OTHER INFORMATION: Xaa is selected from Pro, Ala and Gly

<400> SEQUENCE: 38

Pro Ala Pro Pro Xaa Xaa Gly Pro Ser Val Phe Leu Phe Pro Pro Lys
1               5                   10                  15

Pro Lys Asp Thr Leu Xaa Ile Xaa Arg Xaa Pro Glu Val Thr Cys Val
            20                  25                  30

Val Val Asp Val Ser His Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Phe Arg Val Val Ser Val Leu Thr Val Val His
65                  70                  75                  80

Gln Asp Trp Leu Asn Gly Lys Glu Tyr Lys Cys Xaa Val Ser Asn Lys
                85                  90                  95

Gly Leu Pro Ala Xaa Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ser Val Glu Trp Glu Ser Asn Gly Gln Pro Glu Asn Asn
145                 150                 155                 160

Tyr Lys Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

```
<210> SEQ ID NO 39
<211> LENGTH: 218
<212> TYPE: PRT
<213> ORGANISM: artificial
<220> FEATURE:
<223> OTHER INFORMATION: synthetic construct
<220> FEATURE:
<221> NAME/KEY: MISC_FEATURE
<222> LOCATION: (5)..(5)
<223> OTHER INFORMATION: Xaa is Leu or Phe
<220> FEATURE:
<221> NAME/KEY: MISC_FEATURE
<222> LOCATION: (6)..(6)
<223> OTHER INFORMATION: Xaa is selected from Leu, Ala, Asn, Phe, Gln
      and Val
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: MISC_FEATURE
<222> LOCATION: (25)..(25)
<223> OTHER INFORMATION: Xaa is Met or Tyr
<220> FEATURE:
<221> NAME/KEY: MISC_FEATURE
<222> LOCATION: (27)..(27)
<223> OTHER INFORMATION: Xaa is Ser or Thr
<220> FEATURE:
<221> NAME/KEY: MISC_FEATURE
<222> LOCATION: (29)..(29)
<223> OTHER INFORMATION: Xaa is Thr or Glu
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid
<220> FEATURE:
<221> NAME/KEY: MISC_FEATURE
<222> LOCATION: (112)..(112)
<223> OTHER INFORMATION: Xaa is selected from Lys, Ala, Asp, Glu, His,
      Asn and Gln
<220> FEATURE:
<221> NAME/KEY: MISC_FEATURE
<222> LOCATION: (122)..(122)
<223> OTHER INFORMATION: Xaa is selected from absent (no amino acid
      residue), Ala and Gly

<400> SEQUENCE: 39

Pro Ala Pro Glu Xaa Xaa Gly Gly Pro Ser Val Phe Leu Phe Pro Pro
1               5                   10                  15

Lys Pro Lys Asp Thr Leu Xaa Ile Xaa Arg Xaa Pro Glu Val Thr Cys
            20                  25                  30

Val Val Val Asp Val Ser His Glu Asp Pro Glu Val Gln Phe Lys Trp
        35                  40                  45

Tyr Val Asp Gly Val Glu Val His Asn Ala Lys Thr Lys Pro Arg Glu
    50                  55                  60

Glu Gln Tyr Asn Ser Thr Phe Arg Val Val Ser Val Leu Thr Val Leu
65                  70                  75                  80

His Gln Asp Trp Leu Asn Gly Lys Glu Tyr Lys Cys Xaa Val Ser Asn
                85                  90                  95

Lys Ala Leu Pro Ala Xaa Ile Glu Lys Thr Ile Ser Lys Thr Lys Gly
            100                 105                 110

Gln Pro Arg Glu Pro Gln Val Tyr Thr Leu Pro Pro Ser Arg Glu Glu
        115                 120                 125

Met Thr Lys Asn Gln Val Ser Leu Thr Cys Leu Val Lys Gly Phe Tyr
    130                 135                 140
```

```
Pro Ser Asp Ile Ala Val Glu Trp Glu Ser Ser Gly Gln Pro Glu Asn
145                 150                 155                 160

Asn Tyr Asn Thr Thr Pro Pro Met Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Ile Phe Ser Cys Ser Val Met His Glu Ala Leu His Asn Arg Phe Thr
        195                 200                 205

Gln Lys Ser Leu Ser Leu Ser Pro Gly Lys
    210                 215
```

<210> SEQ ID NO 40
<211> LENGTH: 218
<212> TYPE: PRT
<213> ORGANISM: artificial
<220> FEATURE:
<223> OTHER INFORMATION: synthetic construct
<220> FEATURE:
<221> NAME/KEY: MISC_FEATURE
<222> LOCATION: (5)..(5)
<223> OTHER INFORMATION: Xaa is Phe
<220> FEATURE:
<221> NAME/KEY: MISC_FEATURE
<222> LOCATION: (6)..(6)
<223> OTHER INFORMATION: Xaa is selected from Leu, Ala, Asn, Phe, Gln
    and Val
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: MISC_FEATURE
<222> LOCATION: (25)..(25)
<223> OTHER INFORMATION: Xaa is Met or Tyr
<220> FEATURE:
<221> NAME/KEY: MISC_FEATURE
<222> LOCATION: (27)..(27)
<223> OTHER INFORMATION: Xaa is Ser or Thr
<220> FEATURE:
<221> NAME/KEY: MISC_FEATURE
<222> LOCATION: (29)..(29)
<223> OTHER INFORMATION: Xaa is Thr or Glu
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid
<220> FEATURE:
<221> NAME/KEY: MISC_FEATURE
<222> LOCATION: (112)..(112)
<223> OTHER INFORMATION: Xaa is selected from Lys, Ala, Asp, Glu, His,
    Asn and Gln
<220> FEATURE:
<221> NAME/KEY: MISC_FEATURE
<222> LOCATION: (122)..(122)
<223> OTHER INFORMATION: Xaa is selected from Ser, Ala and Gly

<400> SEQUENCE: 40

```
Pro Ala Pro Glu Xaa Xaa Gly Gly Pro Ser Val Phe Leu Phe Pro Pro
1               5                   10                  15

Lys Pro Lys Asp Thr Leu Xaa Ile Xaa Arg Xaa Pro Glu Val Thr Cys
                20                  25                  30

Val Val Val Asp Val Ser Gln Glu Asp Pro Glu Val Gln Phe Asn Trp
                35                  40                  45

Tyr Val Asp Gly Val Glu Val His Asn Ala Lys Thr Lys Pro Arg Glu
    50                  55                  60
```

-continued

```
Glu Gln Phe Asn Ser Thr Tyr Arg Val Val Ser Val Leu Thr Val Leu
65              70                  75                  80

His Gln Asp Trp Leu Asn Gly Lys Glu Tyr Lys Cys Xaa Val Ser Asn
                85                  90                  95

Lys Gly Leu Pro Ser Xaa Ile Glu Lys Thr Ile Ser Lys Ala Lys Gly
                100                 105                 110

Gln Pro Arg Glu Pro Gln Val Tyr Thr Leu Pro Pro Ser Gln Glu Glu
        115                 120                 125

Met Thr Lys Asn Gln Val Ser Leu Thr Cys Leu Val Lys Gly Phe Tyr
        130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Arg Leu Thr Val Asp Lys Ser Arg Trp Gln Glu Gly Asn
            180                 185                 190

Val Phe Ser Cys Ser Val Met His Glu Ala Leu His Asn His Tyr Thr
            195                 200                 205

Gln Lys Ser Leu Ser Leu Ser Leu Gly Lys
        210                 215
```